(12) United States Patent
Zwart et al.

(10) Patent No.: US 10,675,487 B2
(45) Date of Patent: Jun. 9, 2020

(54) ENERGY DEGRADER ENABLING HIGH-SPEED ENERGY SWITCHING

(71) Applicant: Mevion Medical Systems, Inc., Littleton, MA (US)

(72) Inventors: Gerrit Townsend Zwart, Durham, NH (US); Mark R. Jones, Reading, MA (US); James Cooley, Littleton, MA (US); Adam Molzahn, Littleton, MA (US)

(73) Assignee: Mevion Medical Systems, Inc., Littleton, MA (US)

( * ) Notice: Subject to any disclaimer, the term of this patent is extended or adjusted under 35 U.S.C. 154(b) by 0 days.

(21) Appl. No.: 15/399,250

(22) Filed: Jan. 5, 2017

(65) Prior Publication Data

US 2017/0182338 A1 Jun. 29, 2017

Related U.S. Application Data

(63) Continuation-in-part of application No. 14/137,854, filed on Dec. 20, 2013, now Pat. No. 9,962,560.

(51) Int. Cl.
*A61N 5/10* (2006.01)
*H05H 7/04* (2006.01)
(Continued)

(52) U.S. Cl.
CPC ......... *A61N 5/1077* (2013.01); *A61N 5/1042* (2013.01); *A61N 5/1043* (2013.01);
(Continued)

(58) Field of Classification Search
None
See application file for complete search history.

(56) References Cited

U.S. PATENT DOCUMENTS 463,291 A 11/1891 Dodson
773,508 A 10/1904 Leblanc
(Continued)

FOREIGN PATENT DOCUMENTS

CA 2629333 A1 5/2007
CN 1377521 A 10/2002
(Continued)

OTHER PUBLICATIONS

Communication pursuant to Article 94(3) EPC for EP14830919.8, 6 pages (dated May 12, 2017).
(Continued)

*Primary Examiner* — Michael J Logie
(74) *Attorney, Agent, or Firm* — Burns & Levinson LLP

(57) ABSTRACT

An example particle therapy system may include: a synchrocyclotron to produce a particle beam; a scanner to move the particle beam in one or more dimensions relative to an irradiation target; and an energy degrader that is between the scanner and the irradiation target. The energy degrader may include multiple plates that are movable relative to a path of the particle beam, with the multiple plates each being controllable to move while in the path of the particle beam and during movement of the particle beam. An aperture may be between the energy degrader and the irradiation target. The aperture being may be to trim the particle beam prior to the particle beam reaching the irradiation target.

23 Claims, 48 Drawing Sheets

(51) Int. Cl.
  *H05H 7/00*  (2006.01)
  *H05H 13/02*  (2006.01)
  *G21K 1/10*  (2006.01)
  *G21K 1/04*  (2006.01)
  *H05H 7/12*  (2006.01)

(52) U.S. Cl.
  CPC ......... *A61N 5/1045* (2013.01); *A61N 5/1048* (2013.01); *A61N 5/1081* (2013.01); *A61N 5/1083* (2013.01); *G21K 1/046* (2013.01); *G21K 1/10* (2013.01); *H05H 7/001* (2013.01); *H05H 7/04* (2013.01); *H05H 13/02* (2013.01); *A61N 2005/1087* (2013.01); *A61N 2005/1095* (2013.01); *H05H 2007/002* (2013.01); *H05H 2007/004* (2013.01); *H05H 2007/007* (2013.01); *H05H 2007/046* (2013.01); *H05H 2007/122* (2013.01)

(56) References Cited

U.S. PATENT DOCUMENTS

| | | |
|---|---|---|
| 2,280,606 A | 4/1942 | Roberts |
| 2,492,324 A | 12/1949 | Salisbury |
| 2,615,129 A | 10/1952 | Mcmillan |
| 2,616,042 A | 10/1952 | Weeks |
| 2,659,000 A | 11/1953 | Salisbury |
| 2,701,304 A | 2/1955 | Dickinson |
| 2,789,222 A | 4/1957 | Martin et al. |
| 2,958,327 A | 11/1960 | Geissmann |
| 3,024,379 A | 3/1962 | Verster |
| 3,175,131 A | 3/1965 | Burleigh et al. |
| 3,432,721 A | 3/1969 | Naydan et al. |
| 3,582,650 A | 6/1971 | Avery |
| 3,679,899 A | 7/1972 | Dimeff |
| 3,689,847 A | 9/1972 | Verster |
| 3,757,118 A | 9/1973 | Hodge et al. |
| 3,868,522 A | 2/1975 | Bigham et al. |
| 3,886,367 A | 5/1975 | Castle, Jr. |
| 3,925,676 A | 12/1975 | Bigham et al. |
| 3,955,089 A | 5/1976 | McIntyre et al. |
| 3,958,327 A | 5/1976 | Marancik et al. |
| 3,992,625 A | 11/1976 | Schmidt et al. |
| 4,038,622 A | 7/1977 | Purcell |
| 4,047,068 A | 9/1977 | Ress et al. |
| 4,112,306 A | 9/1978 | Nunan |
| 4,129,784 A | 12/1978 | Tschunt et al. |
| 4,139,777 A | 2/1979 | Rautenbach |
| 4,197,510 A | 4/1980 | Szu |
| 4,220,866 A | 9/1980 | Taumann et al. |
| 4,230,129 A | 10/1980 | LeVeen |
| 4,256,966 A | 3/1981 | Heinz |
| 4,293,772 A | 10/1981 | Stieber |
| 4,336,505 A | 6/1982 | Meyer |
| 4,342,060 A | 7/1982 | Gibson |
| 4,345,210 A | 8/1982 | Tran |
| 4,353,033 A | 10/1982 | Karasawa |
| 4,425,506 A | 1/1984 | Brown et al. |
| 4,490,616 A | 12/1984 | Cipollina et al. |
| 4,507,614 A | 3/1985 | Prono et al. |
| 4,507,616 A | 3/1985 | Blosser et al. |
| 4,589,126 A | 5/1986 | Augustsson et al. |
| 4,598,208 A | 7/1986 | Brunelli et al. |
| 4,628,523 A | 12/1986 | Heflin |
| 4,633,125 A | 12/1986 | Blosser et al. |
| 4,641,057 A | 2/1987 | Blosser et al. |
| 4,641,104 A | 2/1987 | Blosser et al. |
| 4,651,007 A | 3/1987 | Perusek et al. |
| 4,680,565 A | 7/1987 | Jahnke |
| 4,705,955 A | 11/1987 | Mileikowsky |
| 4,710,722 A | 12/1987 | Jahnke |
| 4,726,046 A | 2/1988 | Nunan |
| 4,734,653 A | 3/1988 | Jahnke |
| 4,736,106 A | 4/1988 | Kashy et al. |
| 4,736,173 A | 4/1988 | Basil, Jr. et al. |
| 4,737,727 A | 4/1988 | Yamada et al. |
| 4,739,173 A | 4/1988 | Blosser et al. |
| 4,745,367 A | 5/1988 | Dustmann et al. |
| 4,754,147 A | 6/1988 | Maughan et al. |
| 4,763,483 A | 8/1988 | Olsen |
| 4,767,930 A | 8/1988 | Stieber et al. |
| 4,769,623 A | 9/1988 | Marsing et al. |
| 4,771,208 A | 9/1988 | Jongen et al. |
| 4,783,634 A | 11/1988 | Yamamoto et al. |
| 4,808,941 A | 2/1989 | Marsing |
| 4,812,658 A | 3/1989 | Koehler |
| 4,843,333 A | 6/1989 | Marsing et al. |
| 4,845,371 A | 7/1989 | Stieber |
| 4,865,284 A | 9/1989 | Gosis et al. |
| 4,868,843 A | 9/1989 | Nunan |
| 4,868,844 A | 9/1989 | Nunan |
| 4,870,287 A | 9/1989 | Cole et al. |
| 4,880,985 A | 11/1989 | Jones |
| 4,894,541 A | 1/1990 | Ono |
| 4,896,206 A | 1/1990 | Denham |
| 4,902,993 A | 2/1990 | Krevet |
| 4,904,949 A | 2/1990 | Wilson |
| 4,905,267 A | 2/1990 | Miller et al. |
| 4,917,344 A | 4/1990 | Prechter et al. |
| 4,943,781 A | 7/1990 | Wilson et al. |
| 4,945,478 A | 7/1990 | Merickel et al. |
| 4,968,915 A | 11/1990 | Wilson et al. |
| 4,987,309 A | 1/1991 | Klasen et al. |
| 4,992,744 A | 2/1991 | Fujita et al. |
| 4,996,496 A | 2/1991 | Kitamura et al. |
| 5,006,759 A | 4/1991 | Krispel |
| 5,010,562 A | 4/1991 | Hernandez et al. |
| 5,012,111 A | 4/1991 | Ueda |
| 5,017,789 A | 5/1991 | Young et al. |
| 5,017,882 A | 5/1991 | Finlan |
| 5,036,290 A | 7/1991 | Sonobe et al. |
| 5,039,057 A | 8/1991 | Prechter et al. |
| 5,039,867 A | 8/1991 | Nishihara et al. |
| 5,046,078 A | 9/1991 | Hernandez et al. |
| 5,072,123 A | 12/1991 | Johnsen |
| 5,111,042 A | 5/1992 | Sullivan et al. |
| 5,111,173 A | 5/1992 | Matsuda et al. |
| 5,117,194 A | 5/1992 | Nakanishi et al. |
| 5,117,212 A | 5/1992 | Yamamoto et al. |
| 5,117,829 A | 6/1992 | Miller et al. |
| 5,144,647 A | 9/1992 | Kikuchi |
| 5,148,032 A | 9/1992 | Hernandez |
| 5,166,531 A | 11/1992 | Huntzinger |
| 5,189,687 A | 2/1993 | Bova et al. |
| 5,191,706 A | 3/1993 | Cosden |
| 5,240,218 A | 8/1993 | Dye |
| 5,260,579 A | 11/1993 | Yasuda et al. |
| 5,260,581 A | 11/1993 | Lesyna et al. |
| 5,278,533 A | 1/1994 | Kawaguchi |
| 5,285,166 A | 2/1994 | Hiramoto et al. |
| 5,317,164 A | 5/1994 | Kurokawa |
| 5,336,891 A | 8/1994 | Crewe |
| 5,341,104 A | 8/1994 | Anton et al. |
| 5,349,198 A | 9/1994 | Takanaka |
| 5,365,742 A | 11/1994 | Boffito et al. |
| 5,374,913 A | 12/1994 | Pissantezky et al. |
| 5,382,914 A | 1/1995 | Hamm et al. |
| 5,401,973 A | 3/1995 | McKeown et al. |
| 5,405,235 A | 4/1995 | Lebre et al. |
| 5,434,420 A | 7/1995 | McKeown et al. |
| 5,440,133 A | 8/1995 | Moyers et al. |
| 5,451,794 A | 9/1995 | McKeown et al. |
| 5,461,773 A | 10/1995 | Kawaguchi |
| 5,463,291 A | 10/1995 | Carroll et al. |
| 5,464,411 A | 11/1995 | Schulte et al. |
| 5,492,922 A | 2/1996 | Palkowitz |
| 5,511,549 A | 4/1996 | Legg et al. |
| 5,521,469 A | 5/1996 | Laisne |
| 5,538,942 A | 7/1996 | Koyama et al. |
| 5,549,616 A | 8/1996 | Schulte et al. |
| 5,561,697 A | 10/1996 | Takafuji et al. |
| 5,585,642 A | 12/1996 | Britton et al. |
| 5,633,747 A | 5/1997 | Nikoonahad |
| 5,635,721 A | 6/1997 | Bardi et al. |

(56) References Cited

U.S. PATENT DOCUMENTS

| | | | |
|---|---|---|---|
| 5,668,371 A * | 9/1997 | Deasy | A61N 5/1042 250/505.1 |
| 5,672,878 A | 9/1997 | Yao | |
| 5,691,679 A | 11/1997 | Ackermann et al. | |
| 5,726,448 A | 3/1998 | Smith et al. | |
| 5,727,554 A | 3/1998 | Kalend et al. | |
| 5,730,745 A | 3/1998 | Schulte et al. | |
| 5,748,703 A | 5/1998 | Cosman | |
| 5,751,781 A | 5/1998 | Brown et al. | |
| 5,764,723 A | 6/1998 | Weinberger et al. | |
| 5,778,047 A | 7/1998 | Mansfield et al. | |
| 5,783,914 A | 7/1998 | Hiramoto et al. | |
| 5,784,431 A | 7/1998 | Kalend et al. | |
| 5,797,924 A | 8/1998 | Schulte et al. | |
| 5,811,944 A | 9/1998 | Sampayan et al. | |
| 5,818,058 A | 10/1998 | Nakanishi et al. | |
| 5,821,705 A | 10/1998 | Caporaso et al. | |
| 5,825,845 A | 10/1998 | Blair et al. | |
| 5,841,237 A | 11/1998 | Alton | |
| 5,846,043 A | 12/1998 | Spath | |
| 5,851,182 A | 12/1998 | Sahadevan | |
| 5,866,912 A | 2/1999 | Slater et al. | |
| 5,874,811 A | 2/1999 | Finlan et al. | |
| 5,895,926 A | 4/1999 | Britton et al. | |
| 5,920,601 A | 7/1999 | Nigg et al. | |
| 5,929,458 A | 7/1999 | Nemezawa et al. | |
| 5,963,615 A | 10/1999 | Egley et al. | |
| 5,986,274 A | 11/1999 | Akiyama et al. | |
| 5,993,373 A | 11/1999 | Nonaka et al. | |
| 6,008,499 A | 12/1999 | Hiramoto et al. | |
| 6,034,377 A | 3/2000 | Pu | |
| 6,057,655 A | 5/2000 | Jongen | |
| 6,061,426 A | 5/2000 | Linders et al. | |
| 6,064,807 A | 5/2000 | Arai et al. | |
| 6,066,851 A | 5/2000 | Madono et al. | |
| 6,080,992 A | 6/2000 | Nonaka et al. | |
| 6,087,670 A | 7/2000 | Hiramoto et al. | |
| 6,087,672 A | 7/2000 | Matsuda et al. | |
| 6,094,760 A | 8/2000 | Nonaka et al. | |
| 6,118,848 A | 9/2000 | Reiffel | |
| 6,140,021 A | 10/2000 | Nakasuji et al. | |
| 6,144,875 A | 11/2000 | Schweikard et al. | |
| 6,158,708 A | 12/2000 | Egley et al. | |
| 6,207,952 B1 | 3/2001 | Kan et al. | |
| 6,219,403 B1 | 4/2001 | Nishihara | |
| 6,222,905 B1 | 4/2001 | Yoda et al. | |
| 6,241,671 B1 | 6/2001 | Ritter et al. | |
| 6,246,066 B1 | 6/2001 | Yuehu | |
| 6,256,591 B1 | 7/2001 | Yoda et al. | |
| 6,265,837 B1 | 7/2001 | Akiyama et al. | |
| 6,268,610 B1 | 7/2001 | Pu | |
| 6,278,239 B1 | 8/2001 | Caporaso et al. | |
| 6,279,579 B1 | 8/2001 | Riaziat et al. | |
| 6,307,914 B1 | 10/2001 | Kunieda et al. | |
| 6,316,776 B1 | 11/2001 | Hiramoto et al. | |
| 6,366,021 B1 | 4/2002 | Meddaugh et al. | |
| 6,369,585 B2 | 4/2002 | Yao | |
| 6,380,545 B1 | 4/2002 | Yan | |
| 6,407,505 B1 | 6/2002 | Bertsche | |
| 6,417,634 B1 | 7/2002 | Bergstrom | |
| 6,433,336 B1 | 8/2002 | Jongen et al. | |
| 6,433,349 B2 | 8/2002 | Akiyama et al. | |
| 6,433,494 B1 | 8/2002 | Kulish et al. | |
| 6,441,569 B1 | 8/2002 | Janzow | |
| 6,443,349 B1 | 9/2002 | Van Der Burg | |
| 6,459,769 B1 | 10/2002 | Cosman | |
| 6,465,957 B1 | 10/2002 | Whitham et al. | |
| 6,472,834 B2 | 10/2002 | Hiramoto et al. | |
| 6,476,403 B1 | 11/2002 | Dolinskii et al. | |
| 6,492,922 B1 | 12/2002 | New | |
| 6,493,424 B2 | 12/2002 | Whitham | |
| 6,498,444 B1 | 12/2002 | Hanna et al. | |
| 6,501,981 B1 | 12/2002 | Schweikard et al. | |
| 6,519,316 B1 | 2/2003 | Collins | |
| 6,593,696 B2 | 7/2003 | Ding et al. | |
| 6,594,336 B2 | 7/2003 | Nishizawa et al. | |
| 6,600,164 B1 | 7/2003 | Badura et al. | |
| 6,617,598 B1 | 9/2003 | Matsuda | |
| 6,621,889 B1 | 9/2003 | Mostafavi | |
| 6,630,675 B2 | 10/2003 | Ghelmansarai | |
| 6,639,234 B1 | 10/2003 | Badura et al. | |
| 6,646,383 B2 | 11/2003 | Bertsche et al. | |
| 6,670,618 B1 | 12/2003 | Hartmann et al. | |
| 6,683,162 B2 | 1/2004 | Scheinberg et al. | |
| 6,683,318 B1 | 1/2004 | Haberer et al. | |
| 6,683,426 B1 | 1/2004 | Kleeven | |
| 6,693,283 B2 | 2/2004 | Eickhoff et al. | |
| 6,710,362 B2 | 3/2004 | Kraft et al. | |
| 6,713,773 B1 | 3/2004 | Lyons et al. | |
| 6,713,976 B1 | 3/2004 | Zumoto et al. | |
| 6,714,620 B2 | 3/2004 | Caflisch et al. | |
| 6,717,162 B1 | 4/2004 | Jongen | |
| 6,745,072 B1 | 6/2004 | Badura et al. | |
| 6,757,355 B1 | 6/2004 | Siochi | |
| 6,769,806 B2 | 8/2004 | Moyers | |
| 6,774,383 B2 | 8/2004 | Norimine et al. | |
| 6,777,689 B2 | 8/2004 | Nelson | |
| 6,777,700 B2 | 8/2004 | Yanagisawa et al. | |
| 6,780,149 B1 | 8/2004 | Schulte | |
| 6,792,078 B2 | 9/2004 | Kato et al. | |
| 6,799,068 B1 | 9/2004 | Hartmann et al. | |
| 6,800,866 B2 | 10/2004 | Amemiya et al. | |
| 6,803,591 B2 | 10/2004 | Muramatsu et al. | |
| 6,813,336 B1 | 11/2004 | Siochi | |
| 6,814,694 B1 | 11/2004 | Pedroni | |
| 6,819,743 B2 | 11/2004 | Kato et al. | |
| 6,822,244 B2 | 11/2004 | Beloussov et al. | |
| 6,823,045 B2 | 11/2004 | Kato et al. | |
| 6,853,142 B2 | 2/2005 | Chistyakov | |
| 6,853,703 B2 | 2/2005 | Svatos et al. | |
| 6,864,770 B2 | 3/2005 | Nemoto et al. | |
| 6,865,254 B2 | 3/2005 | Nafstadius | |
| 6,873,123 B2 | 3/2005 | Marchand et al. | |
| 6,878,951 B2 | 4/2005 | Ma | |
| 6,891,177 B1 | 5/2005 | Kraft et al. | |
| 6,891,924 B1 | 5/2005 | Yoda et al. | |
| 6,894,300 B2 | 5/2005 | Reimoser et al. | |
| 6,897,451 B2 | 5/2005 | Kaercher et al. | |
| 6,907,105 B2 | 6/2005 | Otto | |
| 6,914,396 B1 | 7/2005 | Symons et al. | |
| 6,931,100 B2 | 8/2005 | Kato et al. | |
| 6,936,832 B2 | 8/2005 | Norimine et al. | |
| 6,953,943 B2 | 10/2005 | Yanagisawa et al. | |
| 6,965,116 B1 | 11/2005 | Wagner et al. | |
| 6,969,194 B1 | 11/2005 | Nafstadius | |
| 6,979,832 B2 | 12/2005 | Yanagisawa et al. | |
| 6,984,835 B2 | 1/2006 | Harada | |
| 6,992,312 B2 | 1/2006 | Yanagisawa et al. | |
| 6,993,112 B2 | 1/2006 | Hesse | |
| 6,998,604 B2 | 2/2006 | Nishizawa et al. | |
| 7,008,105 B2 | 3/2006 | Amann et al. | |
| 7,011,447 B2 | 3/2006 | Moyers | |
| 7,012,267 B2 | 3/2006 | Moriyama et al. | |
| 7,014,361 B1 | 3/2006 | Ein-Gal | |
| 7,026,636 B2 | 4/2006 | Yanagisawa et al. | |
| 7,038,403 B2 | 5/2006 | Mastrangeli et al. | |
| 7,041,479 B2 | 5/2006 | Swartz et al. | |
| 7,045,781 B2 | 5/2006 | Adamec et al. | |
| 7,049,613 B2 | 5/2006 | Yanagisawa et al. | |
| 7,053,389 B2 | 5/2006 | Yanagisawa et al. | |
| 7,054,801 B2 | 5/2006 | Sakamoto et al. | |
| 7,060,997 B2 | 6/2006 | Norimine et al. | |
| 7,071,479 B2 | 7/2006 | Yanagisawa et al. | |
| 7,073,508 B2 | 7/2006 | Moyers | |
| 7,081,619 B2 | 7/2006 | Bashkirov et al. | |
| 7,084,410 B2 | 8/2006 | Beloussov et al. | |
| 7,091,478 B2 | 8/2006 | Haberer | |
| 7,095,823 B2 | 8/2006 | Topolnjak et al. | |
| 7,102,144 B2 | 9/2006 | Matsuda et al. | |
| 7,122,811 B2 | 10/2006 | Matsuda et al. | |
| 7,122,966 B2 | 10/2006 | Norling et al. | |
| 7,122,978 B2 | 10/2006 | Nakanishi et al. | |
| 7,135,678 B2 | 11/2006 | Wang et al. | |
| 7,138,771 B2 | 11/2006 | Bechthold et al. | |

(56) References Cited

U.S. PATENT DOCUMENTS

| | | |
|---|---|---|
| 7,154,107 B2 | 12/2006 | Yanagisawa et al. |
| 7,154,108 B2 | 12/2006 | Tadokoro et al. |
| 7,154,991 B2 | 12/2006 | Earnst et al. |
| 7,162,005 B2 | 1/2007 | Bjorkholm |
| 7,173,264 B2 | 2/2007 | Moriyama et al. |
| 7,173,265 B2 | 2/2007 | Miller et al. |
| 7,173,385 B2 | 2/2007 | Caporaso et al. |
| 7,186,991 B2 | 3/2007 | Kato et al. |
| 7,193,227 B2 | 3/2007 | Hiramoto et al. |
| 7,199,382 B2 | 4/2007 | Rigney et al. |
| 7,208,748 B2 | 4/2007 | Sliski et al. |
| 7,212,608 B2 | 5/2007 | Nagamine et al. |
| 7,212,609 B2 | 5/2007 | Nagamine et al. |
| 7,221,733 B1 | 5/2007 | Takai et al. |
| 7,227,161 B2 | 6/2007 | Matsuda et al. |
| 7,247,869 B2 | 7/2007 | Tadokoro et al. |
| 7,257,191 B2 | 8/2007 | Sommer |
| 7,259,529 B2 | 8/2007 | Tanaka |
| 7,262,424 B2 | 8/2007 | Moriyama et al. |
| 7,262,565 B2 | 8/2007 | Fujisawa |
| 7,268,358 B2 | 9/2007 | Ma et al. |
| 7,274,018 B2 | 9/2007 | Adamec et al. |
| 7,280,633 B2 | 10/2007 | Cheng et al. |
| 7,295,649 B2 | 11/2007 | Johnsen |
| 7,297,967 B2 | 11/2007 | Yanagisawa et al. |
| 7,301,162 B2 | 11/2007 | Matsuda et al. |
| 7,307,264 B2 | 12/2007 | Brusasco et al. |
| 7,317,192 B2 | 1/2008 | Ma |
| 7,318,805 B2 | 1/2008 | Schweikard et al. |
| 7,319,231 B2 | 1/2008 | Moriyama et al. |
| 7,319,336 B2 | 1/2008 | Baur et al. |
| 7,331,713 B2 | 2/2008 | Moyers |
| 7,332,880 B2 | 2/2008 | Ina et al. |
| 7,345,291 B2 | 3/2008 | Kats |
| 7,345,292 B2 | 3/2008 | Moriyama et al. |
| 7,348,557 B2 | 3/2008 | Armit |
| 7,348,579 B2 | 3/2008 | Pedroni |
| 7,351,988 B2 | 4/2008 | Naumann et al. |
| 7,355,189 B2 | 4/2008 | Yanagisawa et al. |
| 7,368,740 B2 | 5/2008 | Beloussov et al. |
| 7,372,053 B2 | 5/2008 | Yamashita et al. |
| 7,378,672 B2 | 5/2008 | Harada |
| 7,381,979 B2 | 6/2008 | Yamashita et al. |
| 7,386,099 B1 | 6/2008 | Kasper et al. |
| 7,397,054 B2 | 7/2008 | Natori et al. |
| 7,397,901 B1 | 7/2008 | Johnsen |
| 7,398,309 B2 | 7/2008 | Baumann et al. |
| 7,402,822 B2 | 7/2008 | Guertin et al. |
| 7,402,823 B2 | 7/2008 | Guertin et al. |
| 7,402,824 B2 | 7/2008 | Guertin et al. |
| 7,402,963 B2 | 7/2008 | Sliski et al. |
| 7,405,407 B2 | 7/2008 | Hiramoto et al. |
| 7,425,717 B2 | 9/2008 | Matsuda et al. |
| 7,432,516 B2 | 10/2008 | Peggs et al. |
| 7,439,528 B2 | 10/2008 | Nishiuchi et al. |
| 7,446,328 B2 | 11/2008 | Rigney et al. |
| 7,446,490 B2 | 11/2008 | Jongen et al. |
| 7,449,701 B2 | 11/2008 | Fujimaki et al. |
| 7,453,076 B2 | 11/2008 | Welch et al. |
| 7,465,944 B2 | 12/2008 | Ueno et al. |
| 7,466,085 B2 | 12/2008 | Nutt |
| 7,468,506 B2 | 12/2008 | Rogers et al. |
| 7,473,913 B2 | 1/2009 | Hermann et al. |
| 7,476,867 B2 | 1/2009 | Fritsch et al. |
| 7,476,883 B2 | 1/2009 | Nutt |
| 7,482,606 B2 | 1/2009 | Groezinger et al. |
| 7,492,556 B2 | 2/2009 | Atkins et al. |
| 7,507,975 B2 | 3/2009 | Mohr |
| 7,525,104 B2 | 4/2009 | Harada |
| 7,531,818 B2 | 5/2009 | Brahme |
| 7,541,905 B2 | 6/2009 | Antaya |
| 7,547,901 B2 | 6/2009 | Guertin et al. |
| 7,554,096 B2 | 6/2009 | Ward et al. |
| 7,554,097 B2 | 6/2009 | Ward et al. |
| 7,554,275 B2 | 6/2009 | Amaldi |
| 7,555,103 B2 | 6/2009 | Johnsen |
| 7,557,358 B2 | 7/2009 | Ward et al. |
| 7,557,359 B2 | 7/2009 | Ward et al. |
| 7,557,360 B2 | 7/2009 | Ward et al. |
| 7,557,361 B2 | 7/2009 | Ward et al. |
| 7,560,698 B2 | 7/2009 | Rietzel |
| 7,560,715 B2 | 7/2009 | Pedroni |
| 7,560,717 B2 | 7/2009 | Matsuda et al. |
| 7,567,694 B2 | 7/2009 | Lu et al. |
| 7,574,251 B2 | 8/2009 | Lu et al. |
| 7,576,499 B2 | 8/2009 | Caporaso et al. |
| 7,579,603 B2 | 8/2009 | Birgy et al. |
| 7,579,610 B2 | 8/2009 | Grozinger et al. |
| 7,582,866 B2 | 9/2009 | Furuhashi et al. |
| 7,582,885 B2 | 9/2009 | Katagiri et al. |
| 7,582,886 B2 | 9/2009 | Trbojevic |
| 7,586,112 B2 | 9/2009 | Chiba et al. |
| 7,598,497 B2 | 10/2009 | Yamamoto et al. |
| 7,609,009 B2 | 10/2009 | Tanaka et al. |
| 7,609,809 B2 | 10/2009 | Kapatoes et al. |
| 7,609,811 B1 | 10/2009 | Siljamaki et al. |
| 7,615,942 B2 | 11/2009 | Sanders et al. |
| 7,626,347 B2 | 12/2009 | Sliski et al. |
| 7,629,598 B2 | 12/2009 | Harada |
| 7,629,599 B2 | 12/2009 | Hashimoto |
| 7,639,853 B2 | 12/2009 | Olivera et al. |
| 7,639,854 B2 | 12/2009 | Schnarr et al. |
| 7,643,661 B2 | 1/2010 | Ruchala et al. |
| 7,656,258 B1 | 2/2010 | Antaya et al. |
| 7,659,521 B2 | 2/2010 | Pedroni |
| 7,659,528 B2 | 2/2010 | Uematsu |
| 7,668,291 B2 | 2/2010 | Nord et al. |
| 7,672,429 B2 | 3/2010 | Urano et al. |
| 7,679,049 B2 | 3/2010 | Rietzel |
| 7,679,073 B2 | 3/2010 | Urano et al. |
| 7,682,078 B2 | 3/2010 | Rietzel |
| 7,692,166 B2 | 4/2010 | Muraki et al. |
| 7,692,168 B2 | 4/2010 | Moriyama et al. |
| 7,696,499 B2 | 4/2010 | Miller et al. |
| 7,696,847 B2 | 4/2010 | Antaya |
| 7,701,677 B2 | 4/2010 | Schultz et al. |
| 7,709,818 B2 | 5/2010 | Matsuda et al. |
| 7,710,051 B2 | 5/2010 | Caporaso et al. |
| 7,718,982 B2 | 5/2010 | Sliski et al. |
| 7,723,036 B2 | 5/2010 | Racila et al. |
| 7,728,311 B2 | 6/2010 | Gall |
| 7,746,978 B2 | 6/2010 | Cheng et al. |
| 7,755,068 B2 | 7/2010 | Ma et al. |
| 7,755,305 B2 | 7/2010 | Umezawa et al. |
| 7,759,642 B2 | 7/2010 | Nir |
| 7,763,867 B2 | 7/2010 | Birgy et al. |
| 7,763,873 B2 | 7/2010 | Flynn et al. |
| 7,767,988 B2 | 8/2010 | Kaiser et al. |
| 7,770,231 B2 | 8/2010 | Prater et al. |
| 7,772,577 B2 | 8/2010 | Saito et al. |
| 7,773,723 B2 | 8/2010 | Nord et al. |
| 7,773,788 B2 | 8/2010 | Lu et al. |
| 7,778,488 B2 | 8/2010 | Nord et al. |
| 7,783,010 B2 | 8/2010 | Clayton |
| 7,784,124 B2 | 8/2010 | Long et al. |
| 7,784,127 B2 | 8/2010 | Kuro et al. |
| 7,786,433 B2 | 8/2010 | Gunzert-Marx et al. |
| 7,786,451 B2 | 8/2010 | Ward et al. |
| 7,786,452 B2 | 8/2010 | Ward et al. |
| 7,789,560 B2 | 9/2010 | Moyers |
| 7,791,051 B2 | 9/2010 | Beloussov et al. |
| 7,796,731 B2 | 9/2010 | Nord et al. |
| 7,801,269 B2 | 9/2010 | Cravens et al. |
| 7,801,270 B2 | 9/2010 | Nord et al. |
| 7,801,988 B2 | 9/2010 | Baumann et al. |
| 7,807,982 B2 | 10/2010 | Nishiuchi et al. |
| 7,809,107 B2 | 10/2010 | Nord et al. |
| 7,812,319 B2 | 10/2010 | Diehl et al. |
| 7,812,326 B2 | 10/2010 | Grozinger et al. |
| 7,816,657 B2 | 10/2010 | Hansmann et al. |
| 7,817,778 B2 | 10/2010 | Nord et al. |
| 7,817,836 B2 | 10/2010 | Chao et al. |
| 7,818,045 B2 | 10/2010 | Rietzel |
| 7,825,388 B2 | 11/2010 | Nihongi et al. |

(56) References Cited

U.S. PATENT DOCUMENTS

| | | |
|---|---|---|
| 7,826,593 B2 | 11/2010 | Svensson et al. |
| 7,834,334 B2 | 11/2010 | Grozinger et al. |
| 7,834,336 B2 | 11/2010 | Boeh et al. |
| 7,835,494 B2 | 11/2010 | Nord et al. |
| 7,835,502 B2 | 11/2010 | Spence et al. |
| 7,839,972 B2 | 11/2010 | Ruchala et al. |
| 7,839,973 B2 | 11/2010 | Nord et al. |
| 7,848,488 B2 | 12/2010 | Mansfield |
| 7,857,756 B2 | 12/2010 | Warren et al. |
| 7,858,592 B2 | 12/2010 | Shames et al. |
| 7,860,216 B2 | 12/2010 | Jongen et al. |
| 7,860,550 B2 | 12/2010 | Saracen et al. |
| 7,868,301 B2 | 1/2011 | Diehl |
| 7,875,846 B2 | 1/2011 | Gunzert-Marx et al. |
| 7,875,861 B2 | 1/2011 | Huttenberger et al. |
| 7,875,868 B2 | 1/2011 | Moriyama et al. |
| 7,881,431 B2 | 2/2011 | Aoi et al. |
| 7,894,574 B1 | 2/2011 | Nord et al. |
| 7,903,781 B2 | 3/2011 | Foland et al. |
| 7,906,769 B2 | 3/2011 | Blasche et al. |
| 7,907,987 B2 | 3/2011 | Dempsey |
| 7,914,734 B2 | 3/2011 | Livingston |
| 7,919,765 B2 | 4/2011 | Timmer |
| 7,920,040 B2 | 4/2011 | Antaya et al. |
| 7,920,675 B2 | 4/2011 | Lomax et al. |
| 7,928,415 B2 | 4/2011 | Bert et al. |
| 7,934,869 B2 | 5/2011 | Ivanov et al. |
| 7,939,809 B2 | 5/2011 | Balakin |
| 7,940,881 B2 | 5/2011 | Jongen et al. |
| 7,940,894 B2 | 5/2011 | Balakin |
| 7,943,913 B2 | 5/2011 | Balakin |
| 7,947,969 B2 | 5/2011 | Pu |
| 7,949,096 B2 | 5/2011 | Cheng et al. |
| 7,950,587 B2 | 5/2011 | Henson et al. |
| 7,953,205 B2 | 5/2011 | Balakin |
| 7,957,508 B2 | 6/2011 | Brooks et al. |
| 7,960,710 B2 | 6/2011 | Kruip et al. |
| 7,961,844 B2 | 6/2011 | Takeda et al. |
| 7,977,648 B2 | 7/2011 | Westerly et al. |
| 7,977,656 B2 | 7/2011 | Fujimaki et al. |
| 7,977,657 B2 | 7/2011 | Flynn et al. |
| 7,982,198 B2 | 7/2011 | Nishiuchi et al. |
| 7,982,416 B2 | 7/2011 | Tanaka et al. |
| 7,984,715 B2 | 7/2011 | Moyers |
| 7,986,768 B2 | 7/2011 | Nord et al. |
| 7,987,053 B2 | 7/2011 | Schaffner |
| 7,989,785 B2 | 8/2011 | Emhofer et al. |
| 7,990,524 B2 | 8/2011 | Jureller et al. |
| 7,997,553 B2 | 8/2011 | Sloan et al. |
| 8,002,466 B2 | 8/2011 | Von Neubeck et al. |
| 8,003,964 B2 | 8/2011 | Stark et al. |
| 8,009,803 B2 | 8/2011 | Nord et al. |
| 8,009,804 B2 | 8/2011 | Siljamaki et al. |
| 8,016,336 B2 | 9/2011 | Messinger et al. |
| 8,039,822 B2 | 10/2011 | Rietzel |
| 8,041,006 B2 | 10/2011 | Boyden et al. |
| 8,044,364 B2 | 10/2011 | Yamamoto |
| 8,045,679 B2 | 10/2011 | Balakin |
| 8,049,187 B2 | 11/2011 | Tachikawa |
| 8,053,508 B2 | 11/2011 | Korkut et al. |
| 8,053,739 B2 | 11/2011 | Rietzel |
| 8,053,745 B2 | 11/2011 | Moore |
| 8,053,746 B2 | 11/2011 | Timmer et al. |
| 8,063,381 B2 | 11/2011 | Tsoupas et al. |
| 8,067,748 B2 | 11/2011 | Balakin |
| 8,069,675 B2 | 12/2011 | Radovinsky et al. |
| 8,071,966 B2 | 12/2011 | Kaiser et al. |
| 8,080,801 B2 | 12/2011 | Safai |
| 8,085,899 B2 | 12/2011 | Nord et al. |
| 8,089,054 B2 | 1/2012 | Balakin |
| 8,090,074 B2 | 1/2012 | Filiberti et al. |
| 8,093,564 B2 | 1/2012 | Balakin |
| 8,093,568 B2 | 1/2012 | Mackie et al. |
| 8,111,125 B2 | 2/2012 | Antaya et al. |
| 8,129,694 B2 | 3/2012 | Balakin |
| 8,129,699 B2 | 3/2012 | Balakin |
| 8,144,832 B2 | 3/2012 | Balakin |
| 8,153,989 B2 | 4/2012 | Tachikawa et al. |
| 8,154,001 B2 | 4/2012 | Flynn et al. |
| 8,163,709 B2 | 4/2012 | Kodym et al. |
| 8,173,981 B2 | 5/2012 | Trbojevic |
| 8,178,859 B2 | 5/2012 | Balakin |
| 8,183,541 B2 | 5/2012 | Wilkens et al. |
| 8,188,688 B2 | 5/2012 | Balakin |
| 8,189,889 B2 | 5/2012 | Pearlstein et al. |
| 8,190,233 B2 | 5/2012 | Dempsey |
| 8,198,607 B2 | 6/2012 | Balakin |
| 8,207,656 B2 | 6/2012 | Baumgartner et al. |
| 8,222,613 B2 | 7/2012 | Tajiri et al. |
| 8,227,768 B2 | 7/2012 | Smick et al. |
| 8,229,072 B2 | 7/2012 | Balakin |
| 8,232,536 B2 | 7/2012 | Harada |
| 8,238,513 B2 | 8/2012 | Ma |
| 8,253,121 B2 | 8/2012 | Gnutzmann et al. |
| 8,254,521 B2 | 8/2012 | Brooks et al. |
| 8,263,954 B2 | 9/2012 | Iwata |
| 8,283,645 B2 | 10/2012 | Guneysel |
| 8,288,742 B2 | 10/2012 | Balakin |
| 8,291,717 B2 | 10/2012 | Radovinsky et al. |
| 8,294,127 B2 | 10/2012 | Tachibana |
| 8,304,725 B2 | 11/2012 | Komuro et al. |
| 8,304,750 B2 | 11/2012 | Preikszas et al. |
| 8,309,941 B2 | 11/2012 | Balakin |
| 8,330,132 B2 | 12/2012 | Guertin et al. |
| 8,334,520 B2 | 12/2012 | Otaka et al. |
| 8,335,397 B2 | 12/2012 | Takane et al. |
| 8,344,340 B2 | 1/2013 | Gall et al. |
| 8,350,214 B2 | 1/2013 | Otaki et al. |
| 8,351,571 B2 | 1/2013 | Brinks et al. |
| 8,354,656 B2 | 1/2013 | Beloussov et al. |
| 8,368,038 B2 | 2/2013 | Balakin |
| 8,368,043 B2 | 2/2013 | Havelange et al. |
| 8,373,143 B2 | 2/2013 | Balakin |
| 8,373,145 B2 | 2/2013 | Balakin |
| 8,373,146 B2 | 2/2013 | Balakin |
| 8,374,314 B2 | 2/2013 | Balakin |
| 8,378,299 B2 | 2/2013 | Frosien |
| 8,378,311 B2 | 2/2013 | Balakin |
| 8,378,312 B1 | 2/2013 | Gordon et al. |
| 8,378,321 B2 | 2/2013 | Balakin |
| 8,382,943 B2 | 2/2013 | Clark |
| 8,384,053 B2 | 2/2013 | Balakin |
| 8,389,949 B2 | 3/2013 | Harada et al. |
| 8,399,866 B2 | 3/2013 | Balakin |
| 8,405,042 B2 | 3/2013 | Honda et al. |
| 8,405,056 B2 | 3/2013 | Amaldi et al. |
| 8,415,643 B2 | 4/2013 | Balakin |
| 8,416,918 B2 | 4/2013 | Nord et al. |
| 8,421,041 B2 | 4/2013 | Balakin |
| 8,426,833 B2 | 4/2013 | Trbojevic |
| 8,436,323 B2 | 5/2013 | Iseki et al. |
| 8,436,325 B2 | 5/2013 | Noda et al. |
| 8,436,327 B2 | 5/2013 | Balakin |
| 8,440,987 B2 | 5/2013 | Stephani et al. |
| 8,445,872 B2 | 5/2013 | Behrens et al. |
| 8,459,714 B2 | 6/2013 | Pomper et al. |
| 8,461,559 B2 | 6/2013 | Lomax |
| 8,466,441 B2 | 6/2013 | Iwata et al. |
| 8,472,583 B2 | 6/2013 | Star-Lack et al. |
| 8,481,951 B2 | 7/2013 | Jongen et al. |
| 8,483,357 B2 | 7/2013 | Siljamaki et al. |
| 8,487,278 B2 | 7/2013 | Balakin |
| 8,487,282 B2 | 7/2013 | Iseki et al. |
| 8,507,195 B2 | 8/2013 | Richer et al. |
| 8,519,365 B2 | 8/2013 | Balakin |
| 8,525,419 B2 | 9/2013 | Smith et al. |
| 8,525,447 B2 | 9/2013 | Antaya |
| 8,525,448 B2 | 9/2013 | Tanaka et al. |
| 8,536,548 B2 | 9/2013 | Otani et al. |
| 8,541,762 B2 | 9/2013 | Claereboudt et al. |
| 8,546,769 B2 | 10/2013 | Uno |
| 8,552,406 B2 | 10/2013 | Phaneuf et al. |
| 8,552,408 B2 | 10/2013 | Hanawa et al. |
| 8,558,461 B2 | 10/2013 | Poehlmann-Martins et al. |

(56) References Cited

U.S. PATENT DOCUMENTS

| | | |
|---|---|---|
| 8,558,485 B2 | 10/2013 | Antaya |
| 8,565,377 B2 | 10/2013 | Robar et al. |
| 8,569,717 B2 | 10/2013 | Balakin |
| 8,575,563 B2 | 11/2013 | Cameron et al. |
| 8,575,564 B2 | 11/2013 | Iwata |
| 8,575,579 B2 | 11/2013 | Moskvin et al. |
| 8,581,215 B2 | 11/2013 | Balakin |
| 8,581,218 B2 | 11/2013 | Fujimoto et al. |
| 8,581,523 B2 | 11/2013 | Gall et al. |
| 8,581,525 B2 | 11/2013 | Antaya et al. |
| 8,586,948 B2 | 11/2013 | Pu et al. |
| 8,598,543 B2 | 12/2013 | Balakin |
| 8,601,116 B2 | 12/2013 | Baumann et al. |
| 8,604,454 B2 | 12/2013 | Guertin et al. |
| 8,613,694 B2 | 12/2013 | Walsh |
| 8,614,554 B2 | 12/2013 | Balakin |
| 8,614,612 B2 | 12/2013 | Antaya et al. |
| 8,618,519 B2 | 12/2013 | Ueda |
| 8,618,521 B2 | 12/2013 | Loo et al. |
| 8,619,242 B2 | 12/2013 | Suzuki |
| 8,624,528 B2 | 1/2014 | Balakin |
| 8,625,739 B2 | 1/2014 | Balakin |
| 8,627,822 B2 | 1/2014 | Balakin |
| 8,632,448 B1 | 1/2014 | Schulte et al. |
| 8,633,160 B2 | 1/2014 | Belmares et al. |
| 8,637,818 B2 | 1/2014 | Balakin |
| 8,637,839 B2 | 1/2014 | Brauer |
| 8,642,978 B2 | 2/2014 | Balakin |
| 8,643,314 B2 | 2/2014 | Touchi |
| 8,644,571 B1 | 2/2014 | Schulte et al. |
| 8,653,314 B2 | 2/2014 | Pelati et al. |
| 8,653,473 B2 | 2/2014 | Yajima |
| 8,657,354 B2 | 2/2014 | Pomper et al. |
| 8,657,743 B2 | 2/2014 | Rietzel et al. |
| 8,688,197 B2 | 4/2014 | Balakin |
| 8,702,578 B2 | 4/2014 | Fahrig et al. |
| 8,710,462 B2 | 4/2014 | Balakin |
| 8,712,011 B2 | 4/2014 | Robar et al. |
| 8,716,663 B2 | 5/2014 | Brusasco et al. |
| 8,718,231 B2 | 5/2014 | Balakin |
| 8,735,848 B2 | 5/2014 | Asaba |
| 8,748,852 B2 | 6/2014 | Jongen |
| 8,750,453 B2 | 6/2014 | Cheng et al. |
| 8,754,386 B2 | 6/2014 | Iwata |
| 8,766,217 B2 | 7/2014 | Balakin |
| 8,766,218 B2 | 7/2014 | Jongen |
| 8,771,754 B2 | 7/2014 | Hallahan |
| 8,791,435 B2 | 7/2014 | Balakin |
| 8,791,656 B1 | 7/2014 | Zwart et al. |
| 8,796,648 B2 | 8/2014 | Fujimoto et al. |
| 8,822,965 B2 | 9/2014 | Asaba |
| 8,835,885 B2 | 9/2014 | Ogasawara |
| 8,847,179 B2 | 9/2014 | Fujitaka et al. |
| 8,859,264 B2 | 10/2014 | Bert et al. |
| 8,866,109 B2 | 10/2014 | Sasai |
| 8,890,097 B2 | 11/2014 | Iwata |
| 8,896,239 B2 | 11/2014 | Balakin |
| 8,897,857 B2 | 11/2014 | Tome et al. |
| 8,901,509 B2 | 12/2014 | Balakin |
| 8,901,520 B2 | 12/2014 | Tachibana et al. |
| 8,907,309 B2 | 12/2014 | Spotts |
| 8,907,311 B2 | 12/2014 | Gall et al. |
| 8,907,594 B2 | 12/2014 | Begg et al. |
| 8,916,838 B2 | 12/2014 | Claereboudt et al. |
| 8,916,841 B2 | 12/2014 | Totake et al. |
| 8,916,843 B2 | 12/2014 | Gall et al. |
| 8,927,946 B2 | 1/2015 | Behrens et al. |
| 8,927,950 B2 | 1/2015 | Gall et al. |
| 8,933,650 B2 | 1/2015 | O'Neal, III et al. |
| 8,941,083 B2 | 1/2015 | Stark et al. |
| 8,941,084 B2 | 1/2015 | Balakin |
| 8,941,086 B2 | 1/2015 | Yajima |
| 8,947,021 B2 | 2/2015 | Tsutsui |
| 8,948,341 B2 | 2/2015 | Beckman |
| 8,952,343 B2 | 2/2015 | Stephani et al. |
| 8,952,634 B2 | 2/2015 | Sliski et al. |
| 8,957,396 B2 | 2/2015 | Balakin |
| 8,963,111 B2 | 2/2015 | Claereboudt et al. |
| 8,963,112 B1 | 2/2015 | Balakin |
| 8,964,936 B2 | 2/2015 | Brooks et al. |
| 8,969,834 B2 | 3/2015 | Balakin |
| 8,970,137 B2 | 3/2015 | Gall et al. |
| 8,971,363 B2 | 3/2015 | Levecq et al. |
| 8,975,600 B2 | 3/2015 | Balakin |
| 8,975,602 B2 | 3/2015 | Huber et al. |
| 8,975,836 B2 | 3/2015 | Bromberg et al. |
| 8,986,186 B2 | 3/2015 | Zhang et al. |
| 8,993,522 B2 | 3/2015 | Vidyasagar et al. |
| 9,006,693 B2 | 4/2015 | Sasai |
| 9,007,740 B2 | 4/2015 | Touchi |
| 9,012,832 B2 | 4/2015 | Bert et al. |
| 9,012,866 B2 | 4/2015 | Benna et al. |
| 9,012,873 B2 | 4/2015 | Fujimoto et al. |
| 9,018,601 B2 | 4/2015 | Balakin |
| 9,018,603 B2 | 4/2015 | Loo et al. |
| 9,024,256 B2 | 5/2015 | Ruan et al. |
| 9,029,760 B2 | 5/2015 | Beddar et al. |
| 9,044,600 B2 | 6/2015 | Balakin |
| 9,056,199 B2 | 6/2015 | Balakin |
| 9,058,910 B2 | 6/2015 | Balakin |
| 9,060,998 B2 | 6/2015 | Stockfleth |
| 9,061,142 B2 | 6/2015 | Vilsmeier |
| 9,061,143 B2 | 6/2015 | Sasai et al. |
| 9,084,887 B2 | 7/2015 | Schulte et al. |
| 9,084,890 B2 | 7/2015 | Iwata |
| 9,089,696 B2 | 7/2015 | Verhaegen et al. |
| 9,093,209 B2 | 7/2015 | Jongen |
| 9,095,040 B2 | 7/2015 | Balakin |
| 9,108,050 B2 | 8/2015 | Bula et al. |
| 9,114,253 B2 | 8/2015 | Dempsey |
| 9,142,385 B1 | 9/2015 | Iwanaga |
| 9,155,186 B2 | 10/2015 | Zwart et al. |
| 9,155,908 B2 | 10/2015 | Meltsner et al. |
| 9,185,789 B2 | 11/2015 | Zwart et al. |
| 9,186,525 B2 | 11/2015 | Prieels et al. |
| 9,188,685 B2 | 11/2015 | Takayanagi et al. |
| 9,196,082 B2 | 11/2015 | Pearlstein et al. |
| 9,220,920 B2 | 12/2015 | Schulte et al. |
| 9,220,923 B2 | 12/2015 | Yajima et al. |
| 9,237,640 B2 | 1/2016 | Abs et al. |
| 9,237,642 B2 | 1/2016 | Kleeven |
| 9,245,336 B2 | 1/2016 | Mallya et al. |
| 9,254,396 B2 | 2/2016 | Mihaylov |
| 9,259,155 B2 | 2/2016 | Bharat et al. |
| 9,271,385 B2 | 2/2016 | Verbruggen et al. |
| 9,283,406 B2 | 3/2016 | Prieels |
| 9,283,407 B2 | 3/2016 | Benna et al. |
| 9,289,140 B2 | 3/2016 | Ross et al. |
| 9,289,624 B2 | 3/2016 | Jongen |
| 9,297,912 B2 | 3/2016 | Campbell et al. |
| 9,301,384 B2 | 3/2016 | Zwart et al. |
| 9,302,121 B2 | 4/2016 | Totake et al. |
| 9,305,742 B2 | 4/2016 | Aptaker et al. |
| 9,324,468 B2 | 4/2016 | Mansfield et al. |
| 9,355,784 B2 | 5/2016 | Abs |
| 9,364,688 B2 | 6/2016 | Pausch et al. |
| 9,370,089 B2 | 6/2016 | Ungaro et al. |
| 9,381,379 B2 | 7/2016 | Beckman |
| 9,393,443 B2 | 7/2016 | Fujimoto et al. |
| 9,417,302 B2 | 8/2016 | Kuhn |
| 9,451,688 B2 | 9/2016 | Jongen |
| 9,451,689 B2 | 9/2016 | Tsutsui |
| 9,452,300 B2 | 9/2016 | Anferov |
| 9,452,301 B2 | 9/2016 | Gall et al. |
| 9,468,608 B2 | 10/2016 | Lin et al. |
| 9,492,684 B2 | 11/2016 | Takayanagi et al. |
| 9,776,017 B2 | 10/2017 | Flynn et al. |
| 9,999,787 B1 | 6/2018 | Ruohonen et al. |
| 10,258,810 B2 | 4/2019 | Zwart et al. |
| 2001/0022502 A1 | 9/2001 | Akiyama et al. |
| 2002/0058007 A1 | 5/2002 | Scheinberg et al. |
| 2002/0101959 A1 | 8/2002 | Kato et al. |
| 2002/0172317 A1 | 11/2002 | Maksimchuk et al. |
| 2003/0048080 A1 | 3/2003 | Amemiya et al. |

(56) References Cited

U.S. PATENT DOCUMENTS

| | | |
|---|---|---|
| 2003/0125622 A1 | 7/2003 | Schweikard et al. |
| 2003/0136924 A1 | 7/2003 | Kraft et al. |
| 2003/0152197 A1 | 8/2003 | Moyers |
| 2003/0163015 A1 | 8/2003 | Yanagisawa et al. |
| 2003/0183779 A1 | 10/2003 | Norimine et al. |
| 2003/0234369 A1 | 12/2003 | Glukhoy |
| 2004/0000650 A1* | 1/2004 | Yanagisawa ......... A61N 5/1042 250/492.3 |
| 2004/0017888 A1 | 1/2004 | Seppi et al. |
| 2004/0056212 A1 | 3/2004 | Yanagisawa et al. |
| 2004/0061077 A1 | 4/2004 | Muramatsu et al. |
| 2004/0061078 A1 | 4/2004 | Muramatsu et al. |
| 2004/0085023 A1 | 5/2004 | Chistyakov |
| 2004/0098445 A1 | 5/2004 | Baumann et al. |
| 2004/0111134 A1 | 6/2004 | Muramatsu et al. |
| 2004/0118081 A1 | 6/2004 | Reimoser et al. |
| 2004/0149934 A1 | 8/2004 | Yanagisawa et al. |
| 2004/0155206 A1 | 8/2004 | Marchand et al. |
| 2004/0159795 A1 | 8/2004 | Kaercher et al. |
| 2004/0164254 A1 | 8/2004 | Beloussov et al. |
| 2004/0173763 A1 | 9/2004 | Moriyama et al. |
| 2004/0174958 A1 | 9/2004 | Moriyama et al. |
| 2004/0183033 A1 | 9/2004 | Moriyama et al. |
| 2004/0183035 A1 | 9/2004 | Yanagisawa et al. |
| 2004/0190680 A1 | 9/2004 | Chang |
| 2004/0200982 A1 | 10/2004 | Moriyama et al. |
| 2004/0200983 A1 | 10/2004 | Fujimaki et al. |
| 2004/0213381 A1 | 10/2004 | Harada |
| 2004/0227104 A1 | 11/2004 | Matsuda et al. |
| 2004/0232356 A1 | 11/2004 | Norimine et al. |
| 2004/0240626 A1 | 12/2004 | Moyers |
| 2005/0029472 A1 | 2/2005 | Ueno et al. |
| 2005/0051740 A1 | 3/2005 | Yanagisawa et al. |
| 2005/0058245 A1 | 3/2005 | Ein-Gal |
| 2005/0072940 A1 | 4/2005 | Beloussov et al. |
| 2005/0079235 A1 | 4/2005 | Stockfleth |
| 2005/0087700 A1 | 4/2005 | Tadokoro et al. |
| 2005/0089141 A1 | 4/2005 | Brown |
| 2005/0099145 A1 | 5/2005 | Nishiuchi et al. |
| 2005/0113327 A1 | 5/2005 | Roiz et al. |
| 2005/0127306 A1 | 6/2005 | Yanagisawa et al. |
| 2005/0139787 A1 | 6/2005 | Chiba et al. |
| 2005/0161618 A1 | 7/2005 | Pedroni |
| 2005/0167616 A1 | 8/2005 | Yanagisawa et al. |
| 2005/0184686 A1 | 8/2005 | Caporaso et al. |
| 2005/0186179 A1 | 8/2005 | Harats et al. |
| 2005/0205806 A1 | 9/2005 | Tadokoro et al. |
| 2005/0228255 A1 | 10/2005 | Saracen et al. |
| 2005/0231138 A1* | 10/2005 | Nakanishi ................ G21K 5/04 315/500 |
| 2005/0234327 A1 | 10/2005 | Saracen et al. |
| 2005/0247890 A1 | 11/2005 | Norimine et al. |
| 2005/0259779 A1 | 11/2005 | Abraham-Fuchs et al. |
| 2006/0017015 A1 | 1/2006 | Sliski et al. |
| 2006/0033042 A1* | 2/2006 | Groezinger .......... A61N 5/1043 250/492.1 |
| 2006/0067468 A1 | 3/2006 | Rietzel |
| 2006/0126792 A1 | 6/2006 | Li |
| 2006/0127879 A1 | 6/2006 | Fuccione |
| 2006/0145088 A1 | 7/2006 | Ma |
| 2006/0175991 A1 | 8/2006 | Fujisawa |
| 2006/0192146 A1 | 8/2006 | Yanagisawa et al. |
| 2006/0204478 A1 | 9/2006 | Harats et al. |
| 2006/0219948 A1 | 10/2006 | Ueno et al. |
| 2006/0284562 A1 | 12/2006 | Hruby et al. |
| 2007/0001128 A1 | 1/2007 | Sliski et al. |
| 2007/0013273 A1 | 1/2007 | Albert et al. |
| 2007/0014654 A1 | 1/2007 | Haverfield et al. |
| 2007/0018120 A1 | 1/2007 | Beloussov et al. |
| 2007/0023699 A1 | 2/2007 | Yamashita et al. |
| 2007/0029510 A1 | 2/2007 | Hermann et al. |
| 2007/0031337 A1 | 2/2007 | Schulte |
| 2007/0034812 A1 | 2/2007 | Ma et al. |
| 2007/0051904 A1 | 3/2007 | Kaiser et al. |
| 2007/0053484 A1 | 3/2007 | Chiba et al. |
| 2007/0059387 A1 | 3/2007 | Stockfleth |
| 2007/0075273 A1 | 4/2007 | Birgy et al. |
| 2007/0083101 A1 | 4/2007 | Rietzel |
| 2007/0092812 A1 | 4/2007 | Caporaso et al. |
| 2007/0108922 A1 | 5/2007 | Amaldi |
| 2007/0114464 A1 | 5/2007 | Birgy et al. |
| 2007/0114471 A1 | 5/2007 | Birgy et al. |
| 2007/0114945 A1 | 5/2007 | Mattaboni et al. |
| 2007/0145916 A1 | 6/2007 | Caporaso et al. |
| 2007/0171015 A1 | 7/2007 | Antaya |
| 2007/0181519 A1 | 8/2007 | Khoshnevis |
| 2007/0217575 A1 | 9/2007 | Kaiser et al. |
| 2007/0262269 A1 | 11/2007 | Trbojevic |
| 2007/0284548 A1 | 12/2007 | Kaiser et al. |
| 2008/0023644 A1* | 1/2008 | Pedroni ................... A61N 5/10 250/400 |
| 2008/0029706 A1 | 2/2008 | Kaiser et al. |
| 2008/0031414 A1 | 2/2008 | Coppens |
| 2008/0061241 A1 | 3/2008 | Rietzel |
| 2008/0063147 A1 | 3/2008 | Juschka et al. |
| 2008/0073591 A1 | 3/2008 | Mohr |
| 2008/0078942 A1 | 4/2008 | Rietzel |
| 2008/0093567 A1 | 4/2008 | Gall |
| 2008/0123816 A1 | 5/2008 | Mori et al. |
| 2008/0131419 A1 | 6/2008 | Roiz et al. |
| 2008/0159478 A1 | 7/2008 | Keall et al. |
| 2008/0179544 A1 | 7/2008 | Kaiser et al. |
| 2008/0191142 A1 | 8/2008 | Pedroni |
| 2008/0191152 A1 | 8/2008 | Grozinger et al. |
| 2008/0205599 A1 | 8/2008 | Hashimoto |
| 2008/0218102 A1 | 9/2008 | Sliski et al. |
| 2008/0219407 A1 | 9/2008 | Kaiser et al. |
| 2008/0219410 A1 | 9/2008 | Gunzert-Marx et al. |
| 2008/0219411 A1 | 9/2008 | Gunzert-Marx et al. |
| 2008/0237494 A1 | 10/2008 | Beloussov et al. |
| 2008/0237495 A1 | 10/2008 | Grozinger et al. |
| 2008/0267349 A1 | 10/2008 | Rietzel |
| 2008/0270517 A1 | 10/2008 | Baumann et al. |
| 2008/0272284 A1 | 11/2008 | Rietzel |
| 2008/0290299 A1 | 11/2008 | Hansmann et al. |
| 2008/0298550 A1 | 12/2008 | Otto |
| 2008/0301872 A1 | 12/2008 | Fahrig et al. |
| 2008/0315111 A1 | 12/2008 | Sommer |
| 2009/0008575 A1* | 1/2009 | Okazaki .................. A61N 5/10 250/492.1 |
| 2009/0032742 A1 | 2/2009 | Kaiser et al. |
| 2009/0050819 A1 | 2/2009 | Ma et al. |
| 2009/0060130 A1 | 3/2009 | Wilkens et al. |
| 2009/0065717 A1 | 3/2009 | Kaiser et al. |
| 2009/0069640 A1 | 3/2009 | Rietzel et al. |
| 2009/0077209 A1 | 3/2009 | Schneider |
| 2009/0096179 A1 | 4/2009 | Stark et al. |
| 2009/0098145 A1 | 4/2009 | Mata et al. |
| 2009/0101833 A1 | 4/2009 | Emhofer et al. |
| 2009/0114847 A1 | 5/2009 | Grozinger et al. |
| 2009/0140671 A1 | 6/2009 | O'Neal, III et al. |
| 2009/0140672 A1 | 6/2009 | Gall et al. |
| 2009/0175414 A1 | 7/2009 | Messinger et al. |
| 2009/0189095 A1 | 7/2009 | Flynn et al. |
| 2009/0200483 A1 | 8/2009 | Gall et al. |
| 2009/0230327 A1 | 9/2009 | Rietzel |
| 2009/0234237 A1 | 9/2009 | Ross et al. |
| 2009/0242789 A1 | 10/2009 | Tachikawa |
| 2009/0261275 A1 | 10/2009 | Rietzel |
| 2009/0274269 A1 | 11/2009 | Foland et al. |
| 2009/0296885 A1 | 12/2009 | Boeh et al. |
| 2009/0309046 A1 | 12/2009 | Balakin |
| 2009/0309047 A1 | 12/2009 | Gunzert-Marx et al. |
| 2009/0309520 A1 | 12/2009 | Balakin |
| 2009/0314960 A1 | 12/2009 | Balakin |
| 2009/0314961 A1 | 12/2009 | Balakin |
| 2009/0321656 A1 | 12/2009 | Rietzel et al. |
| 2010/0006106 A1 | 1/2010 | Balakin |
| 2010/0006770 A1 | 1/2010 | Balakin |
| 2010/0008466 A1 | 1/2010 | Balakin |
| 2010/0014639 A1 | 1/2010 | Balakin |
| 2010/0014640 A1 | 1/2010 | Balakin |
| 2010/0020932 A1 | 1/2010 | Yi et al. |
| 2010/0027745 A1 | 2/2010 | Balakin |

(56) References Cited

U.S. PATENT DOCUMENTS

| | | |
|---|---|---|
| 2010/0034357 A1 | 2/2010 | Svesson et al. |
| 2010/0038552 A1 | 2/2010 | Trbojevic |
| 2010/0045213 A1 | 2/2010 | Sliski et al. |
| 2010/0046697 A1 | 2/2010 | Balakin |
| 2010/0046713 A1 | 2/2010 | Nord et al. |
| 2010/0060209 A1 | 3/2010 | Balakin |
| 2010/0090122 A1 | 4/2010 | Balakin |
| 2010/0091948 A1 | 4/2010 | Balakin |
| 2010/0126964 A1 | 5/2010 | Smith et al. |
| 2010/0127184 A1 | 5/2010 | Balakin |
| 2010/0128846 A1 | 5/2010 | Balakin |
| 2010/0133444 A1 | 6/2010 | Balakin |
| 2010/0133446 A1 | 6/2010 | Balakin |
| 2010/0141183 A1 | 6/2010 | Balakin |
| 2010/0166150 A1 | 7/2010 | Perkins et al. |
| 2010/0171045 A1 | 7/2010 | Guneysel |
| 2010/0171447 A1 | 7/2010 | Balakin |
| 2010/0176309 A1* | 7/2010 | Mackie .................. A61N 5/10 250/492.3 |
| 2010/0207552 A1 | 8/2010 | Balakin |
| 2010/0230617 A1 | 9/2010 | Gall |
| 2010/0230620 A1 | 9/2010 | Tsoupas et al. |
| 2010/0243911 A1* | 9/2010 | Fujii .................. A61N 5/1044 250/400 |
| 2010/0252754 A1 | 10/2010 | Brown et al. |
| 2010/0264327 A1 | 10/2010 | Bonig et al. |
| 2010/0266100 A1 | 10/2010 | Balakin |
| 2010/0288945 A1 | 11/2010 | Gnutzmann et al. |
| 2010/0296534 A1 | 11/2010 | Levecq et al. |
| 2010/0301235 A1* | 12/2010 | Bert .................. A61N 5/103 250/492.3 |
| 2010/0308235 A1 | 12/2010 | Sliski et al. |
| 2010/0320404 A1 | 12/2010 | Tanke |
| 2010/0327187 A1 | 12/2010 | Beloussov et al. |
| 2011/0006214 A1 | 1/2011 | Bonig |
| 2011/0009736 A1 | 1/2011 | Maltz et al. |
| 2011/0011729 A1 | 1/2011 | Poehlmann-Martins et al. |
| 2011/0027853 A1 | 2/2011 | Bert et al. |
| 2011/0047469 A1 | 2/2011 | Baumann et al. |
| 2011/0049396 A1 | 3/2011 | Furth et al. |
| 2011/0051891 A1 | 3/2011 | O'Connor et al. |
| 2011/0101236 A1 | 5/2011 | Cameron et al. |
| 2011/0118529 A1 | 5/2011 | Balakin |
| 2011/0118531 A1 | 5/2011 | Balakin |
| 2011/0124976 A1 | 5/2011 | Sabczynski et al. |
| 2011/0127443 A1 | 6/2011 | Comer et al. |
| 2011/0147608 A1 | 6/2011 | Balakin |
| 2011/0150180 A1 | 6/2011 | Balakin |
| 2011/0166219 A1 | 7/2011 | Stockfleth |
| 2011/0180720 A1 | 7/2011 | Balakin |
| 2011/0180731 A1 | 7/2011 | Welsh |
| 2011/0182410 A1 | 7/2011 | Balakin |
| 2011/0186720 A1 | 8/2011 | Jongen et al. |
| 2011/0196223 A1 | 8/2011 | Balakin |
| 2011/0200170 A1 | 8/2011 | Nord et al. |
| 2011/0204262 A1* | 8/2011 | Pu .................. A61N 5/1048 250/492.1 |
| 2011/0214588 A1 | 9/2011 | Grubling et al. |
| 2011/0218430 A1 | 9/2011 | Balakin |
| 2011/0220794 A1 | 9/2011 | Censor et al. |
| 2011/0220798 A1 | 9/2011 | Bauricher et al. |
| 2011/0231147 A1* | 9/2011 | Takayanagi .............. G01T 1/29 702/150 |
| 2011/0233423 A1 | 9/2011 | Balakin |
| 2011/0238440 A1 | 9/2011 | Leuschner |
| 2011/0248188 A1 | 10/2011 | Brusasco et al. |
| 2011/0278477 A1 | 11/2011 | Balakin |
| 2011/0284757 A1 | 11/2011 | Butuceanu et al. |
| 2011/0284760 A1 | 11/2011 | Balakin |
| 2011/0285327 A1 | 11/2011 | Begg et al. |
| 2011/0297850 A1 | 12/2011 | Claereboudt et al. |
| 2011/0299657 A1 | 12/2011 | Havelange et al. |
| 2011/0299919 A1 | 12/2011 | Stark et al. |
| 2011/0303858 A1* | 12/2011 | Bert .................. A61N 5/1043 250/492.1 |
| 2011/0306870 A1 | 12/2011 | Kuhn |
| 2011/0313232 A1 | 12/2011 | Balakin |
| 2012/0001085 A1 | 1/2012 | Fujimoto et al. |
| 2012/0043481 A1 | 2/2012 | Mansfield et al. |
| 2012/0043482 A1 | 2/2012 | Prince et al. |
| 2012/0056099 A1 | 3/2012 | Behrens et al. |
| 2012/0056109 A1 | 3/2012 | Lomax |
| 2012/0069961 A1 | 3/2012 | Pomper et al. |
| 2012/0077748 A1 | 3/2012 | Vidyasagar et al. |
| 2012/0099704 A1 | 4/2012 | Ruan et al. |
| 2012/0112092 A1 | 5/2012 | Pomper et al. |
| 2012/0119114 A1 | 5/2012 | Brauer |
| 2012/0136194 A1 | 5/2012 | Zhang et al. |
| 2012/0143051 A1 | 6/2012 | Balakin |
| 2012/0205551 A1 | 8/2012 | Balakin |
| 2012/0207276 A1 | 8/2012 | Pomper et al. |
| 2012/0209109 A1 | 8/2012 | Balakin |
| 2012/0223246 A1 | 9/2012 | Stephani et al. |
| 2012/0224667 A1 | 9/2012 | Cheng et al. |
| 2012/0242257 A1 | 9/2012 | Balakin |
| 2012/0248325 A1 | 10/2012 | Balakin |
| 2012/0256103 A1 | 10/2012 | Luzzara |
| 2012/0264998 A1 | 10/2012 | Fujitaka et al. |
| 2012/0267543 A1 | 10/2012 | Noda et al. |
| 2012/0267544 A1* | 10/2012 | Ueda .................. A61N 5/1043 250/396 R |
| 2012/0273665 A1* | 11/2012 | Schulte .................. G01N 23/04 250/252.1 |
| 2012/0273666 A1* | 11/2012 | Bert .................. A61N 5/1048 250/252.1 |
| 2012/0280150 A1 | 11/2012 | Jongen |
| 2012/0303384 A1 | 11/2012 | Stepaniak et al. |
| 2012/0305796 A1* | 12/2012 | Iseki .................. G01T 1/2935 250/396 R |
| 2012/0313003 A1 | 12/2012 | Trbojevic |
| 2012/0326722 A1 | 12/2012 | Weinberg et al. |
| 2013/0001432 A1 | 1/2013 | Jongen |
| 2013/0043403 A1 | 2/2013 | Gordon et al. |
| 2013/0053616 A1 | 2/2013 | Gall et al. |
| 2013/0053617 A1 | 2/2013 | Pu et al. |
| 2013/0068938 A1 | 3/2013 | Heese |
| 2013/0072743 A1 | 3/2013 | Fieres et al. |
| 2013/0072744 A1 | 3/2013 | Moskvin et al. |
| 2013/0086500 A1 | 4/2013 | Kane et al. |
| 2013/0090549 A1 | 4/2013 | Meltsner et al. |
| 2013/0108014 A1 | 5/2013 | Tome et al. |
| 2013/0127375 A1 | 5/2013 | Sliski et al. |
| 2013/0131424 A1 | 5/2013 | Sliski et al. |
| 2013/0131433 A1 | 5/2013 | Katscher et al. |
| 2013/0150647 A1 | 6/2013 | Chen et al. |
| 2013/0163723 A1 | 6/2013 | Tacke |
| 2013/0187060 A1 | 7/2013 | Jongen |
| 2013/0208867 A1 | 8/2013 | Beckman |
| 2013/0209450 A1 | 8/2013 | Cohen et al. |
| 2013/0211482 A1 | 8/2013 | Piipponen |
| 2013/0217946 A1 | 8/2013 | Balakin |
| 2013/0217948 A1 | 8/2013 | Mihaylov |
| 2013/0217950 A1 | 8/2013 | Partanen et al. |
| 2013/0218009 A1 | 8/2013 | Balakin |
| 2013/0221213 A1* | 8/2013 | Takayanagi .......... A61N 5/1048 250/252.1 |
| 2013/0237425 A1 | 9/2013 | Leigh et al. |
| 2013/0237822 A1 | 9/2013 | Gross et al. |
| 2013/0243722 A1 | 9/2013 | Basile et al. |
| 2013/0245113 A1 | 9/2013 | Stockfleth |
| 2013/0259335 A1 | 10/2013 | Mallya et al. |
| 2013/0261430 A1 | 10/2013 | Uhlemann |
| 2013/0267756 A1 | 10/2013 | Totake et al. |
| 2013/0277569 A1 | 10/2013 | Behrens et al. |
| 2013/0299721 A1* | 11/2013 | Sasai .................. A61N 5/1043 250/492.3 |
| 2013/0303824 A1 | 11/2013 | Stephani et al. |
| 2013/0324479 A1 | 12/2013 | Zhang et al. |
| 2013/0345489 A1 | 12/2013 | Beloussov et al. |
| 2014/0005463 A1 | 1/2014 | Jongen |
| 2014/0005464 A1 | 1/2014 | Bharat et al. |
| 2014/0014851 A1 | 1/2014 | Asaba |

(56) References Cited

U.S. PATENT DOCUMENTS

| | | |
|---|---|---|
| 2014/0028220 A1 | 1/2014 | Bromberg et al. |
| 2014/0042934 A1 | 2/2014 | Tsutsui |
| 2014/0046113 A1 | 2/2014 | Fujimoto et al. |
| 2014/0061493 A1 | 3/2014 | Prieels et al. |
| 2014/0066755 A1 | 3/2014 | Matteo et al. |
| 2014/0077699 A1 | 3/2014 | Boswell et al. |
| 2014/0091238 A1* | 4/2014 | Miyashita ................ G21K 1/10 250/492.3 |
| 2014/0091734 A1 | 4/2014 | Gall et al. |
| 2014/0094371 A1 | 4/2014 | Zwart et al. |
| 2014/0094637 A1 | 4/2014 | Zwart et al. |
| 2014/0094638 A1 | 4/2014 | Gall et al. |
| 2014/0094639 A1 | 4/2014 | Zwart et al. |
| 2014/0094640 A1 | 4/2014 | Gall et al. |
| 2014/0094641 A1 | 4/2014 | Gall et al. |
| 2014/0094643 A1 | 4/2014 | Gall et al. |
| 2014/0097920 A1 | 4/2014 | Goldie et al. |
| 2014/0107390 A1 | 4/2014 | Brown et al. |
| 2014/0112453 A1 | 4/2014 | Prince et al. |
| 2014/0113388 A1 | 4/2014 | Bitter et al. |
| 2014/0121441 A1 | 5/2014 | Huber et al. |
| 2014/0128719 A1 | 5/2014 | Longfield |
| 2014/0145090 A9 | 5/2014 | Jongen |
| 2014/0193058 A1 | 7/2014 | Bharat et al. |
| 2014/0200448 A1 | 7/2014 | Schulte et al. |
| 2014/0203186 A1* | 7/2014 | Iwamoto ................ H05H 7/12 250/397 |
| 2014/0221816 A1 | 8/2014 | Franke et al. |
| 2014/0257011 A1 | 9/2014 | Spotts |
| 2014/0257099 A1 | 9/2014 | Balakin |
| 2014/0275699 A1 | 9/2014 | Benna et al. |
| 2014/0308202 A1 | 10/2014 | Matusik et al. |
| 2014/0316184 A1 | 10/2014 | Fujimoto et al. |
| 2014/0330063 A1 | 11/2014 | Balakin |
| 2014/0332691 A1 | 11/2014 | Campbell et al. |
| 2014/0336438 A1 | 11/2014 | Bharat et al. |
| 2014/0350322 A1 | 11/2014 | Schulte et al. |
| 2014/0369958 A1 | 12/2014 | Basile |
| 2014/0371076 A1 | 12/2014 | Jongen |
| 2014/0371511 A1 | 12/2014 | Zwart et al. |
| 2015/0015167 A1 | 1/2015 | Ungaro et al. |
| 2015/0030223 A1 | 1/2015 | Pearlstein et al. |
| 2015/0031933 A1* | 1/2015 | Yamamoto ............ A61N 5/1043 600/1 |
| 2015/0041665 A1 | 2/2015 | Hollebeek et al. |
| 2015/0076370 A1 | 3/2015 | Totake et al. |
| 2015/0080633 A1 | 3/2015 | Anferov |
| 2015/0080634 A1 | 3/2015 | Huber et al. |
| 2015/0087883 A1 | 3/2015 | Boudreau et al. |
| 2015/0087885 A1 | 3/2015 | Boisseau et al. |
| 2015/0087887 A1 | 3/2015 | Iwata |
| 2015/0087960 A1 | 3/2015 | Treffert |
| 2015/0090894 A1 | 4/2015 | Zwart et al. |
| 2015/0099917 A1 | 4/2015 | Bula et al. |
| 2015/0099918 A1* | 4/2015 | Takayanagi ................ G01T 1/29 600/1 |
| 2015/0126797 A1 | 5/2015 | Aptaker et al. |
| 2015/0133714 A1* | 5/2015 | Inaniwa ................ G21K 5/04 600/1 |
| 2015/0146856 A1 | 5/2015 | Beckman |
| 2015/0148584 A1 | 5/2015 | Gall et al. |
| 2015/0174429 A1 | 6/2015 | Zwart et al. |
| 2015/0196534 A1 | 7/2015 | Vidyasagar et al. |
| 2015/0196779 A1 | 7/2015 | Tonner |
| 2015/0209601 A1 | 7/2015 | Benna et al. |
| 2015/0217138 A1 | 8/2015 | Fujimoto et al. |
| 2015/0217140 A1 | 8/2015 | Balakin |
| 2015/0231411 A1 | 8/2015 | O'Neal, III et al. |
| 2015/0273239 A1 | 10/2015 | Hsu et al. |
| 2015/0321025 A1 | 11/2015 | Freud et al. |
| 2015/0328483 A1 | 11/2015 | Odawara et al. |
| 2015/0335463 A1 | 11/2015 | De Gruytere |
| 2015/0335919 A1 | 11/2015 | Behar et al. |
| 2015/0337393 A1 | 11/2015 | Keller et al. |
| 2015/0343238 A1 | 12/2015 | Balakin |
| 2015/0352372 A1 | 12/2015 | Takayanagi et al. |
| 2015/0352374 A1 | 12/2015 | Gattiker et al. |
| 2015/0374324 A1 | 12/2015 | Nishimura et al. |
| 2016/0000387 A1 | 1/2016 | Buchsbaum et al. |
| 2016/0008631 A1 | 1/2016 | Harada et al. |
| 2016/0016010 A1 | 1/2016 | Schulte et al. |
| 2016/0048981 A1 | 2/2016 | Pearlstein et al. |
| 2016/0059039 A1 | 3/2016 | Liu |
| 2016/0067316 A1 | 3/2016 | Sunavala-Dossabhoy |
| 2016/0071623 A1 | 3/2016 | Schewiola et al. |
| 2016/0074675 A1 | 3/2016 | Moskvin et al. |
| 2016/0113884 A1 | 4/2016 | Lin et al. |
| 2016/0136457 A1 | 5/2016 | Jung et al. |
| 2016/0144201 A1 | 5/2016 | Schulte |
| 2016/0172066 A1 | 6/2016 | Claereboudt |
| 2016/0172067 A1 | 6/2016 | Claereboudt et al. |
| 2016/0175052 A1 | 6/2016 | Kumar et al. |
| 2016/0175617 A1 | 6/2016 | Spatola et al. |
| 2016/0199667 A1* | 7/2016 | Flynn ................ A61N 5/1043 600/1 |
| 2016/0199670 A1* | 7/2016 | Michaud ............ A61N 5/1077 600/1 |
| 2016/0199671 A1 | 7/2016 | Jongen |
| 2016/0220846 A1 | 8/2016 | Matteo et al. |
| 2016/0220847 A1 | 8/2016 | Benna et al. |
| 2016/0243232 A1 | 8/2016 | Pickett |
| 2016/0250501 A1 | 9/2016 | Balakin |
| 2016/0250503 A1 | 9/2016 | Balakin et al. |
| 2016/0256712 A1 | 9/2016 | Vahala et al. |
| 2016/0263404 A1 | 9/2016 | Mougenot |
| 2016/0270203 A1 | 9/2016 | Ungaro et al. |
| 2016/0271424 A1 | 9/2016 | Lee et al. |
| 2016/0287899 A1 | 10/2016 | Park et al. |
| 2016/0296766 A1 | 10/2016 | El Fakhri et al. |
| 2016/0303399 A1 | 10/2016 | Balakin |
| 2016/0331999 A1 | 11/2016 | Hartman et al. |
| 2017/0128746 A1 | 5/2017 | Zwart et al. |
| 2017/0157422 A1 | 6/2017 | Zwart et al. |
| 2017/0157424 A1 | 6/2017 | Zwart et al. |
| 2017/0157425 A1 | 6/2017 | Zwart et al. |

FOREIGN PATENT DOCUMENTS

| | | |
|---|---|---|
| CN | 1537657 | 10/2004 |
| CN | 1537657 A | 10/2004 |
| CN | 1816243 A | 8/2006 |
| CN | 101061759 A | 10/2007 |
| CN | 101145409 A | 3/2008 |
| CN | 101361156 A | 2/2009 |
| CN | 101932361 A | 12/2010 |
| CN | 101933405 A | 12/2010 |
| CN | 101933406 A | 12/2010 |
| CN | 102905761 A | 1/2013 |
| DE | 2753397 A1 | 6/1978 |
| DE | 3148100 A1 | 6/1983 |
| DE | 3530446 A1 | 3/1986 |
| DE | 3711245 A1 | 10/1988 |
| DE | 4101094 C1 | 5/1992 |
| DE | 4411171 A1 | 10/1995 |
| DE | 19907098 A1 | 8/2000 |
| DE | 102011089235 A1 | 8/2012 |
| EP | 0194728 A1 | 9/1986 |
| EP | 0208163 A1 | 1/1987 |
| EP | 0221987 A1 | 5/1987 |
| EP | 0222786 A1 | 5/1987 |
| EP | 0277521 A2 | 8/1988 |
| EP | 0306966 A2 | 3/1989 |
| EP | 0388123 A2 | 9/1990 |
| EP | 0465597 A1 | 1/1992 |
| EP | 0499253 A2 | 8/1992 |
| EP | 0751532 A1 | 1/1997 |
| EP | 0776595 A1 | 6/1997 |
| EP | 0864337 A1 | 9/1998 |
| EP | 0911064 A2 | 4/1999 |
| EP | 1069809 A1 | 1/2001 |
| EP | 1153398 A1 | 11/2001 |
| EP | 1294445 A2 | 3/2003 |
| EP | 1348465 A1 | 10/2003 |

(56) References Cited

FOREIGN PATENT DOCUMENTS

| | | |
|---|---|---|
| EP | 1358908 A1 | 11/2003 |
| EP | 1371390 A1 | 12/2003 |
| EP | 1402923 A1 | 3/2004 |
| EP | 1430932 A1 | 6/2004 |
| EP | 1454653 A1 | 9/2004 |
| EP | 1454654 A2 | 9/2004 |
| EP | 1454655 A2 | 9/2004 |
| EP | 1454656 A2 | 9/2004 |
| EP | 1454657 A2 | 9/2004 |
| EP | 1477206 A1 | 11/2004 |
| EP | 1605742 A1 | 12/2005 |
| EP | 1738798 A2 | 1/2007 |
| EP | 1826778 A2 | 8/2007 |
| EP | 1949404 A2 | 7/2008 |
| EP | 2114529 B1 | 11/2009 |
| EP | 2183753 A1 | 5/2010 |
| EP | 2227295 A1 | 9/2010 |
| EP | 2232961 A1 | 9/2010 |
| EP | 2232962 A2 | 9/2010 |
| EP | 2363170 A1 | 9/2011 |
| EP | 2363171 A1 | 9/2011 |
| EP | 2394498 A2 | 12/2011 |
| EP | 2514482 A1 | 10/2012 |
| EP | 2524718 A1 | 11/2012 |
| EP | 3035776 A1 | 6/2016 |
| EP | 3088048 A1 | 11/2016 |
| FR | 2560421 A1 | 8/1985 |
| FR | 2911843 A1 | 8/2008 |
| GB | 0957342 A | 5/1964 |
| GB | 2015821 A | 9/1979 |
| GB | 2361523 A | 10/2001 |
| JP | S47-028762 U | 12/1972 |
| JP | S48-108098 | 12/1973 |
| JP | U48-108098 | 12/1973 |
| JP | 57-162527 | 10/1982 |
| JP | 58-141000 | 8/1983 |
| JP | 61-80800 | 4/1986 |
| JP | S61-80800 A | 4/1986 |
| JP | 61-225798 | 10/1986 |
| JP | 62-150804 | 7/1987 |
| JP | 62-186500 | 8/1987 |
| JP | 63-149344 | 6/1988 |
| JP | 63-218200 | 9/1988 |
| JP | 63-226899 | 9/1988 |
| JP | 64-89621 | 4/1989 |
| JP | 01-276797 | 11/1989 |
| JP | 01-302700 | 12/1989 |
| JP | 4-94198 | 3/1992 |
| JP | H06-036893 A | 2/1994 |
| JP | 06-036893 | 8/1994 |
| JP | 06-233831 | 8/1994 |
| JP | H06-233831 A | 8/1994 |
| JP | 06-036893 | 10/1994 |
| JP | 07-260939 | 10/1995 |
| JP | 07-263196 | 10/1995 |
| JP | 08-173890 | 7/1996 |
| JP | 08-264298 | 10/1996 |
| JP | 09-162585 | 6/1997 |
| JP | 10-071213 | 3/1998 |
| JP | 11-47287 | 2/1999 |
| JP | H1128252 A | 2/1999 |
| JP | 11-102800 | 4/1999 |
| JP | 11-243295 | 9/1999 |
| JP | 2000-243309 A | 9/2000 |
| JP | 2000-294399 A | 10/2000 |
| JP | 2001-6900 | 1/2001 |
| JP | 2001-009050 A | 1/2001 |
| JP | 2001-129103 A | 5/2001 |
| JP | 2001-276238 A | 10/2001 |
| JP | 2001-346893 A | 12/2001 |
| JP | 2002-164686 A | 6/2002 |
| JP | 2003-504628 A | 2/2003 |
| JP | 2003-517755 A | 5/2003 |
| JP | 2004-031115 A | 1/2004 |
| JP | 2005-526578 A | 9/2005 |
| JP | 2006-032282 A | 2/2006 |
| JP | 2006341010 A | 12/2006 |
| JP | 2007307223 A | * 11/2007 ............... A61N 5/10 |
| JP | 2008-068092 A | 3/2008 |
| JP | 2008-507826 A | 3/2008 |
| JP | 04-128717 B2 | 7/2008 |
| JP | 04-129768 B2 | 8/2008 |
| JP | 61-80800 | 1/2009 |
| JP | 2009-515671 A | 4/2009 |
| JP | 2009-516905 A | 4/2009 |
| JP | 04-273409 B2 | 6/2009 |
| JP | 04-337300 B2 | 9/2009 |
| JP | 43-23267 B2 | 9/2009 |
| JP | 2010-536130 A | 11/2010 |
| JP | 2011-505191 A | 2/2011 |
| JP | 2011-505670 A | 2/2011 |
| JP | 2011-507151 A | 3/2011 |
| JP | 05-046928 B2 | 10/2012 |
| JP | 2012-223259 A | 11/2012 |
| JP | 2013-106981 A | 6/2013 |
| JP | 05-341352 B2 | 11/2013 |
| SU | 300137 | 6/1969 |
| SU | 569635 A1 | 8/1977 |
| TW | 200930160 A | 7/2009 |
| TW | 200934682 A | 8/2009 |
| TW | 200939908 A | 9/2009 |
| TW | 200940120 A | 10/2009 |
| WO | WO-1986/07229 A1 | 12/1986 |
| WO | WO-1990/012413 A1 | 10/1990 |
| WO | WO-1992/03028 A1 | 2/1992 |
| WO | WO-1993/02536 A1 | 2/1993 |
| WO | WO-1998/17342 A2 | 4/1998 |
| WO | WO-1999/39385 A1 | 8/1999 |
| WO | WO-2000/40064 A2 | 7/2000 |
| WO | WO-2000/49624 A1 | 8/2000 |
| WO | WO-01/126569 | 4/2001 |
| WO | WO-2001/026230 A1 | 4/2001 |
| WO | WO-02/07817 | 1/2002 |
| WO | WO-2003/039212 A1 | 5/2003 |
| WO | WO-2003/092812 A1 | 11/2003 |
| WO | WO-2004/026401 A1 | 4/2004 |
| WO | WO-2004/101070 A1 | 11/2004 |
| WO | WO-2006-012467 A2 | 2/2006 |
| WO | WO-2007/061937 A2 | 5/2007 |
| WO | WO-2007/084701 A1 | 7/2007 |
| WO | WO-2007/130164 A2 | 11/2007 |
| WO | WO-2007/145906 A2 | 12/2007 |
| WO | WO-2008/030911 A2 | 3/2008 |
| WO | WO-2008/081480 A1 | 7/2008 |
| WO | WO-2009/048745 A2 | 4/2009 |
| WO | WO-2009/070173 A1 | 6/2009 |
| WO | WO-2009/070588 A1 | 6/2009 |
| WO | WO-2009/073480 A2 | 6/2009 |
| WO | WO-2014/018706 A1 | 1/2014 |
| WO | WO-2014/018876 A1 | 1/2014 |
| WO | WO-2015/003111 A1 | 1/2015 |
| WO | WO-2015/095678 A2 | 6/2015 |
| WO | WO-2015/107660 A1 | 7/2015 |
| WO | WO-2017/082984 A1 | 5/2017 |
| WO | WO-2018/128822 A1 | 7/2018 |

OTHER PUBLICATIONS

18th Japan Conference on Radiation and Radioisotopes [Japanese], Nov. 25-27, 1987, 9 pages.
510(k) Summary: Ion Beam Applications S.A., FDA, Jul. 12, 2001, 5 pages.
510(k) Summary: Optivus Proton Beam Therapy System, Jul. 21, 2000, 5 pages.
Abrosimov et al., 1000MeV Proton Beam Therapy facility at Petersburg Nuclear Physics Institute Synchrocyclotron, Medical Radiology (Moscow) 32, 10 (1987) revised in Journal of Physics, Conference Series 41, 2006, pp. 424-432, Institute of Physics Publishing Limited.
Abrosimov et al., Neutron Time-of-flight Spectrometer Gneis at the Gatchina 1 GeV Protron Syncrhocyclotron, Mar. 9, 1985 and revised form Jul. 31, 1985, Lemingrad Nuclear Physics Institute, Gatchina, 188350, USSR (15 pages).

(56) References Cited

OTHER PUBLICATIONS

Adachi et al., A 150MeV FFAG Synchrotron with Return-Yoke Free Magent, Proceedings of the 2001 Particle Accelerator Conference, Chicago, 2001, 3 pages.
Ageyev et al., The IHEP Accelerating and Storage Complex (UNK) Status Report, 11th International Conference on High-Energy Accelerators, 1980, pp. 60-70.
Agosteo et al., Maze Design of a gantry room for proton therapy, Nuclear Instruments & Methods in Physics Research, 1996, Section A, 382, pp. 573-582.
Alexeev et al., R4 Design of Superconducting Magents for Proton Synchrotrons, Proceedings of the Fifth International Cryogenic Engineering Conference, 197 4, pp. 531-533.
Allardyce et al., Performance and Prospects of the Reconstructed CERN 600 MeV Synchrocyclotron, IEEE Transactions on Nuclear Science USA, Jun. 1977, ns-24:(3) 1631-1633.
Alonso, Magnetically Scanned Ion Beams for Radiation Therapy, Accelerator & Fusion Research Division, Lawrence Berkeley Laboratory, Berkeley, CA, Oct. 1988, 13 pages.
Amaldi et al., The Italian project for a hadrontherapy centre Nuclear Instruments and Methods in Physics Research A, 1995, 360, pp. 297-301.
Amaldi, Overview of the world landscape of Hadrontherapy and the projects of the TERA foundation, Physica Medica, An International journal Devoted to the Applications of Physics to Medicine and Biology, Jul. 1998, vol. XIV, Supplement 1, 6th Workshop on Heavy Charged Particles in Biology and Medicine, Instituto Scientific Europeo (ISE), Sep. 29-Oct. 1, 1977, Baveno, pp. 76-85.
An Accelerated Collaboration Meets with Beaming Success, Lawrence Livermore National Laboratory, Apr. 12, 2006, S&TR, Livermore, California, pp. 1-3, http://www.llnl.gov/str/April06/Caporaso.html.
Anferov et al., Status of the Midwest Proton Radiotherapy Institute, Proceedings of the 2003 Particle Accelerator Conference, 2003, pp. 699-701.
Anferov et al., The Indiana University Midwest Proton Radiation Institute, Proceedings of the 2001 Particle Accelerator Conference, 2001, Chicago, pp. 645-647.
Appun, Various problems of magnet fabrication for high-energy accelerators, Journal for All Engineers Interested in the Nuclear Field, 1967, 11 pp. 10-16 (1967) [Lang.: German], English bibliographic information (httn://www.osti.1mv/enernvcitations/nroduct.biblio.isn?ostiid=4442292).
Arduini et al. Physical specifications of clinical proton beams from a synchrotron, Med. Phys, Jun. 1996, 23 ( 6): 939-951.
Badano et al., Proton-Ion Medical Machine Study (PIMMS) Part I, PIMMS, Jan. 1999, 238 pages.
Beam Delivery and Properties, Journal of the ICRU, 2007, 7(2):20 pages.
Beeckman et al., Preliminary design of a reduced cost proton therapy facility using a compact, high field isochronous cyclotron, Nuclear Instruments and Methods in Physics Research B56/57, 1991, pp. 1201-1204.
Bellomo et al., The Superconducting Cyclotron Program at Michigan State University, Bulletin of the American Physical Society, Sep. 1980, 25(7):767.
Benedikt and Carli, Matching to Gantries for Medical Synchrotrons IEEE Proceedings of the 1997 Particle Accelerator Conference, 1997, pp. 13 79-13 81.
Bieth et al., A Very Compact Protontherapy Facility Based on an Extensive Use of High Temperature Superconductors (HTS) Cyclotrons and their Applications 1998, Proceedings of the Fifteenth International Conference on Cyclotrons and their Applications, Caen, Jun. 14-19, 1998, pp. 669-672.
Bigham, Magnetic Trim Rods for Superconducting Cyclotrons, Nuclear Instruments and Methods (North-Holland Publishing Co.), 1975, 141:223-228.
Bimbot, First Studies of the External Beam from the Orsay S.C. 200 MeV, Institut de Physique Nucleaire, BP 1, Orsay, France, IEEE, 1979, pp. 1923-1926.

Blackmore et al., Operation of the Triumf Proton Therapy Facility, IEEE Proceedings of the 1997 Particle Accelerator Conference, May 12-16, 1997, 3:3831-3833.
Bloch, The Midwest Proton Therapy Center, Application of Accelerators in Research and Industry, Proceedings of the Fourteenth Int'l. Conf, Part Two, Nov. 1996, pp. 1253-1255.
Blosser et al., A Compact Superconducting Cyclotron for the Production of High Intensity Protons, Proceedings of the 1997 Particle Accelerator Conference, May 12-16, 1997, 1:1054-1056.
Blosser et al., Advances in Superconducting Cyclotrons at Michigan State University, Proceedings of the 11th International Conference on Cyclotrons and their Applications, Oct. 1986, pp. 157-167, Tokyo.
Blosser et al., Characteristics of a 400 (Q2/A) MeV Super-Conducting Heavy-Ion Cyclotron, Bulletin of the American Physical Society, Oct. 1974, p. 1026.
Blosser et al., Medical Accelerator Projects at Michigan State Univ. IEEE Proceedings of the 1989 Particle Accelerator Conference, Mar. 20-23, 1989, 2:742-746.
Blosser et al., Problems and Accomplishments of Superconducting Cyclotrons, Proceedings of the 14th International Conference, Cyclotrons and Their Applications, Oct. 1995, pp. 674-684.
Blosser et al., Progress toward an experiment to study the effect of RF grounding in an internal ion source on axial oscillations of the beam in a cyclotron, National Superconducting Cyclotron Laboratory, Michigan State University, Report MSUCL-760, CP600, Cyclotrons and their Applications 2011, Sixteenth International Conference, 2001, pp. 274-276.
Blosser et al., Superconducting Cyclotron for Medical Application, IEEE Transactions on Magnetics, Mar. 1989, 25(2): 1746-1754.
Blosser et al., Superconducting Cyclotrons, Seventh International Conference on Cyclotrons and their Applications, Aug. 19-22, 1975, pp. 584-594.
Blosser, Application of Superconductivity in Cyclotron Construction, Ninth International Conference on Cyclotrons and their Applications, Sep. 1981, pp. 147-157.
Blosser, Applications of Superconducting Cyclotrons, Twelfth International Conference on Cyclotrons and Their Applications, May 8-12, 1989, pp. 137-144.
Blosser, Future Cyclotrons, AIP, The Sixth International Cyclotron Conference, 1972, pp. 16-32.
Blosser, H., Present and Future Superconducting Cyclotrons, Bulletin of the American Physical Society, Feb. 1987, 32(2):171 Particle Accelerator Conference, Washington, D.C.
Blosser, H.G., Superconducting Cyclotrons at Michigan State University, Nuclear Instruments & Methods in Physics Research, 1987,vol. B 24/25, part II, pp. 752-756.
Blosser, Medical Cyclotrons, Physics Today, Special Issue Physical Review Centenary, Oct. 1993, pp. 70-73.
Blosser, Preliminary Design Study Exploring Building Features Required for a Proton Therapy Facility for the Ontario Cancer Institute, Mar. 1991, MSUCL-760a, 53 pages.
Blosser, Progress on the Coupled Superconducting Cyclotron Project, Bulletin of the American Physical Society, 1993 (p. 3).
Blosser, Synchrocyclotron Improvement Programs, IEEE Transactions on Nuclear Science USA, Jun. 1969, 16(3):Part I, pp. 405-414.
Blosser, The Michigan State University Superconducting Cyclotron Program, Nuclear Science, Apr. 1979, NS-26(2):2040-2047.
Botha et al., A New Multidisciplinary Separated-Sector Cyclotron Facility, IEEE Transactions on Nuclear Science, 1977, NS-24(3): 1118-1120.
Boyer, A. et al., Basic Applications of Multi-leaf Collimators: Report of Task Group No. 50—Radiation Therapy Committee, AAPM Report No. 72, American Association of Physicists in Medicine by Medical Physics Publishing, 62 pages (2001).
Bues, M. et al., Therapeutic Step and Shoot Proton Beam Spot-Scanning With a Multi-Leaf Collimator: A Monte Carlo Study, Radiation Protection Dosimetry, 115(1-4):164-169 (2005).
Chichili et al., Fabrication of Nb3Sn Shell-Type Coils with Pre-Preg Ceramic Insulation, American Institute of Physics Conference Proceedings, AIP USA, No. 711, (XP-002436709, ISSN: 0094-243X), 2004, pp. 450-457.

(56) References Cited

OTHER PUBLICATIONS

Chong et al., Radiology Clinic North American 7, 3319, 1969, 27 pages.
Chu et al., Instrumentation for Treatment of Cancer Using Proton and Light-ion Beams, Review of Scientific Instruments, Aug. 1993, 64 (8):2055-2122.
Chu et al., Performance Specifications for Proton Medical Facility, Lawrence Berkeley Laboratory, University of California, Mar. 1993, 128 pages.
Chu, Instrumentation in Medical Systems, Accelerator and Fusion Research Division, Lawrence Berkeley Laboratory, University of California, Berkeley, CA, May 1995, 9 pages.
Cole et al., Design and Application of a Proton Therapy Accelerator, Fermi National Accelerator Laboratory, IEEE, 1985, 5 pages.
Collins, et al., The Indiana University Proton Therapy System, Proceedings of EPAC 2006, Edinburgh, Scotland, 2006, 3 pages.
Communication pursuant to Rules 161(1) and 162 EPC in EP14830919.8, 2 pages (Sep. 2, 2016).
Conradi et al., Proposed New Facilities for Proton Therapy at iThemba Labs, Proceedings of EPAC, 2002, pp. 560-562.
C/E Source of Ions for Use in Sychro-Cyclotrons Search, Jan. 31, 2005, 9 pages.
Cosgrove et al., Microdosimetric Studies on the Orsay Proton Synchrocyclotron at 73 and 200 MeV, Radiation Protection Dosimetry, 1997, 70(1-4):493-496.
Coupland, High-field (5 T) pulsed superconducting dipole magnet, Proceedings of the Institution of Electrical EnRineers, Jul. 1974, 121(7):771-778.
Coutrakon et al. Proton Synchrotrons for Cancer Therapy, Application of Accelerators in Research and Industry—Sixteenth International Conf., American Institute of Physics, Nov. 1-5, 2000, vol. 576, pp. 861-864.
Coutrakon et al., A prototype beam delivery system for the proton medical accelerator at Loma Linda, Medical Physics, Nov./Dec. 1991, 18(6):1093-1099.
CPAC Highlights Its Proton Therapy Program at ESTRO Annual Meeting, TomoTherapy Incorporated, Sep. 18, 2008, Madison, Wisconsin, pp. 1-2.
Cuttone, Applications of a Particle Accelerators in Medical Physics, Istituto Nazionale di Fisica Nucleare-Laboratori Nazionali del Sud, V.S. Sofia, 44 Cantania, Italy, Jan. 2010, 17 pages.
Daartz, J. et al., Characterization of a mini-multileaf collimator in a proton beamline, Med. Phys., 36(5):9 pages (2009).
Dahl P, Superconducting Magnet System, American Institute of Physics, AIP Conference Proceedings, 1987-1988, 2: 1329-1376.
Dialog Search, Jan. 31, 2005, 17 pages.
Dugan et al., Tevatron Status IEEE, Particle Accelerator Conference, Accelerator Science & Technology, 1989, pp. 426-430.
Eickhoff et al., The Proposed Accelerator Facility for Light Ion Cancer Therapy in Heidelberg, Proceedings of the 1999 Particle Accelerator Conference, New York, 1999, pp. 2513-2515.
Enchevich et al., Minimizing Phase Losses in the 680 MeV Synchrocyclotron by Correcting the Accelerating Voltage Amplitude, Atomnaya Energiya, 1969, 26:(3):315-316.
Endo et al., Compact Proton and Carbon Ion Synchrotrons for Radiation Therapy, Proceedings of EPAC 2002, Paris France, 2002, pp. 2733-2735.
File History of U.S. Appl. No. 13/303,110.
File History of U.S. Appl. No. 61/843,092, 84 pages (downloaded Oct. 14, 2016).
File History of U.S. Appl. No. 61/900,455, 43 pages (downloaded Oct. 14, 2016).
File History of U.S. Appl. No. 61/946,074, 137 pages (downloaded Oct. 14, 2016).
Final Office Action for U.S. Appl. No. 14/137,854, 29 pages (dated Sep. 19, 2016).
Flanz et al., Large Medical Gantries, Particle Accelerator Conference, Massachusetts General Hospital, 1995, pp. 1-5.
Flanz et al., Operation of a Cyclotron Based Proton Therapy Facility, Massachusetts General Hospital, Boston, MA 02114, pp. 1-4, retrieved from Internet in 2009.
Flanz et al., The Northeast Proton Therapy Center at Massachusetts General Hospital, Fifth Workshop on Heavy Charge Particles in Biology and Medicine, GSI, Darmstadt, Aug. 1995, 11 pages.
Flanz et al., Treating Patients with the NPTC Accelerator Based Proton Treatment Facility, Proceedings of the 2003 Particle Accelerator Conference, 2003, pp. 690-693.
Flood and Frazier, The Wide-Band Driven RF System for the Berkeley 88-Inch Cyclotron, American Institute of Physics, Conference Proceedings., No. 9, 1972, 459-466.
Foster and Kashikhin, Superconducting Superferric Dipole Magent with Cold Iron Core for the VLHC, IEEE Transactions on Applied Superconductivity, Mar. 2002, 12(1):111-115.
Fredriksson, Albin, Robust optimization of radiation therapy accounting for geometric uncertainty, Doctoral Thesis, 57 pages (2013).
Friesel et al., Design and Construction Progress on the IUCF Midwest Proton Radiation Institute, Proceedings of EPAC 2002, 2002, pp. 2736-2738.
Fukumoto et al., A Proton Therapy Facility Plan Cyclotrons and their Applications, Proceedings of the 13th International Conference, Vancouver, Canada, Jul. 6-10, 1992, pp. 258-261.
Fukumoto, Cyclotron Versus Synchrotron for Proton Beam Therapy, KEK Prepr., No. 95-122, Oct. 1995, pp. 533-536.
Gelover, E. et al., A method for modeling laterally asymmetric proton beamlets resulting from collimation, Medical Physics, 42:1321-1334 (2015).
Goto et al., Progress on the Sector Magnets for the Riken SRC, American Institute of Physics, 714 CP600, Cyclotrons and Their Applications 2001, Sixteenth International Conference, 2001, pp. 319-323.
Graffman et al., Design Studies for a 200 MeV Proton Clinic for Radiotherapy, AIP Conference Proceedings: Cyclotrons—1972, 1972, No. 9, pp. 603-615.
Graffman, et. al. Proton radiotherapy with the Uppsala cyclotron. Experience and plans Strahlentherapie, 1985, 161(12):764-770.
Graffman, S., et al., Clinical Trials in Radiotherapy and the Merits of High Energy Protons, Acta Radiol. Therapy Phys. Biol. 9:1-23 (1970).
Hede, Research Groups Promoting Proton Therapy Lite, Journal of the National Cancer Institute, Dec. 6, 2006, 98(23):1682-1684.
Heinz, Superconducting Pulsed Magnetic Systems for High-Energy Synchrotrons, Proceedings of the Fourth International Cryogenic Engineering Conference, May 24-26, 1972, pp. 55-63.
Hentschel et al., Plans for the German National Neutron Therapy Centre with a Hospital-Based 70 MeV Proton Cyclotron at University Hospital Essen/Germany, Cyclotrons and their Applications, Proceedings of the Fifteenth International Conference on Cyclotrons and their Applications, Caen, Franco, Jun. 14-19, 1998, pp. 21-23.
Hepburn et al., Superconducting Cyclotron Neutron Source for Therapy, International Journal of Radiation Oncology Biology Physics, vol. 3 complete, 1977, pp. 387-391.
Hirabayashi, Development of Superconducting Magnets for Beam Lines and Accelerator at KEK, IEEE Transaction on Magnetics, Jan. 1981, MAG-17(1 ):728-731.
Hyer, D. et al., A dynamic collimation system for penumbra reduction in spot-scanning proton therapy: Proof of concept; Medical Physics, 41(9):091701-1-091701-9 (2014).
Indiana's mega-million proton therapy cancer center welcomes its first patients [online] Press release, Health & Medicine Week, 2004, retrieved from NewsRx.com, Mar. 1, 2004, pp. 119-120.
International Preliminary Report on Patentability for PCT/US2014/071448, 14 pages (dated Jun. 30, 2016).
International Search Report and Written Opinion issued in corresponding PCT application No. PCT/US2014/071448 dated Jul. 24, 2015 (18 pages).
International Search Report for PCT/US2016/048037, 11 pages (dated Feb. 6, 2017).
Invitation to Pay Additional Fees and, where applicable, protest fee issued in PCT application PCT/US2014/071448 dated Apr. 13, 2015 (11 pages).

(56) References Cited

OTHER PUBLICATIONS

Invitation to Pay Additional Fees and, where applicable, protest fee issued in PCT application PCT/US2016/048037 dated Oct. 20, 2016 (8 pages).
Ishibashi and Mcinturff, Stress Analysis of Superconducting 1 OT Magnets for Synchrotron, Proceedings of the Ninth International Cryogenic Engineering Conference, May 11-14, 1982, pp. 513-516.
Ishibashi and Mcinturff, Winding Design Study of Superconducting 10 T Dipoles for a Synchrotron, IEEE Transactions on MaRnetics, May 1983, MAG-19(3):1364-1367.
Jahnke et al., First Superconducting Prototype Magnets for a Compact Synchrotron Radiation Source in Operation, IEEE Transactions on MaRnetics, Mar. 1988, 24(2)1230-1232.
Jones and Dershem, Synchrotron Radiation from Proton in a 20 TEV, 10 TESLA Superconducting Super Collider Proceedings of the 12th International Conference on High-Energy Accelerator, Aug. 11-16, 1983, pp. 138-140.
Jones and Mills, The South African National Accelerator Centre: Particle Therapy and Isotope Production Programmes, Radiation Physics and Chemistry, Apr.-Jun. 1998, 51 ( 4-6):571-578.
Jones et al., Status Report of the NAC Particle Therapy Programme, Stralentherapie and Onkologie, vol. 175, Suppl. II, Jun. 1999, pp. 30-32.
Jones, Present Status and Future Trends of Heavy Particle Radiotherapy, Cyclotrons and their Applications 1998, Proceedings of the Fifteenth International Conference on Cyclotrons and their Applications, Jun. 14-19, 1998, pp. 13-20.
Jones, Progress with the 200 MeV Cyclotron Facility at the National Accelerator Centre, Commission of the European Communities Radiation Protection Proceedings, Fifth Symposium on Neutron Dosimetry, Sep. 17-21, 1984, vol. II, pp. 989-998.
Jongen et al., Development of a Low-cost Compact Cyclotron System for Proton Therapy, National Institute of Radiol. Sci,1991, No. 81, DD. 189-200.
Jongen et al., Progress report on the IBA-SHI small cyclotron for cancer therapy Nuclear Instruments and Methods in Physics Research, Section B, vol. 79, issue 1-4, 1993, pp. 885-889.
Jongen et al., The proton therapy system for MGH's NPTC: equipment description and progress report, Bulletin du Cancer/Radiotherapie, Proceedings of the meeting of the European Heavy Particle Theravv Group, 1996, 83(Suool. 1):219-222.
Jongen et al., The proton therapy system for the NPTC: Equipment Description and progress report, Nuclear Instruments and methods in physics research, 1996, Section B, 113(1 ): 522-525.
Kanai et al., Three-dimensional Beam Scanning for Proton Therapy, Nuclear Instruments and Methods in Physic Research, Sep. 1, 1983, The Netherlands, 214(23):491-496.
Karlin et al., Medical Radiology (Moscow), 1983, 28, 13.
Karlin et al., The State and Prospects in the Development of the Medical Proton Tract on the Synchrocyclotron in Gatchina, Med. Radial., Moscow, 28(3):28-32 (Mar. 1983)(German with English Abstract on end of p. 32).
Kats and Druzhinin, Comparison of Methods for Irradiation Prone Patients, Atomic Energy, Feb. 2003, 94(2): 120-123.
Kats and Onosovskii, A Planar Magnetooptical System for the Irradiation of a Lying Patient with a Proton Beam from Various Directions, Instruments and Experimental Techniques, 1996, 39(1):127-131.
Kats and Onosovskii, A Simple, Compact, Flat System for the Irradiation of a Lying Patient with a Proton Beam from Different Directions, Instruments and Experimental Techniques, 1996, 39(1):132-134.
Khoroshkov et al., Moscow Hospital-Based Proton Therapy Facility Design, Am. Journal Clinical Oncology: CCT, Apr. 1994, 17(2):109-114.
Kim and Blosser, Optimized Magnet for a 250 MeV Proton Radiotherapy Cyclotron, Cyclotrons and Their Annlications 2001, May 2001, Sixteenth International Conference, pp. 345-347.
Kim and Yun, A Light-Ion Superconducting Cyclotron System for Multi-Disciplinary Users, Journal of the Korean Physical Society, Sep. 2003, 43(3):325-331.
Kim et al., Construction of 8T Magnet Test Stand for Cyclotron Studies, IEEE Transactions on Applied Superconductivity, Mar. 1993, 3(1):266-268.
Kim et al., Design Study of a Superconducting Cyclotron for Heavy Ion Therapy, Cyclotrons and Their Applications 2001, Sixteenth International Conference, May 13-17, 2001, pp. 324-326.
Kim et al., Trim Coil System for the Riken Cyclotron Ring Cyclotron, Proceedings of the 1997 Particle Accelerator Conference, IEEE, Dec. 1981, vol. 3, pp. 214-235 or 3422-3242, 1998.
Kim, An Eight Tesla Superconducting Magnet for Cyclotron Studies, Ph.D. Dissertation, Michigan State University, Department of Physics and Astronomy, 1994, 13 8 pages.
Kimstrand, Beam Modelling for Treatment Planning of Scanned Proton Beams, Digital Comprehensive Summaries of Uppsala dissertations from the Faculty of Medicine 330, Uppsala Universitet, 2008, 58 pages.
Kishida and Yano, Beam Transport System for the RIKEN SSC (II), Scientific Papers of the Institute of Physical and Chemical Research, Dec. 1981, 75(4):214-235.
Koehler et al., Range Modulators for Protons and Heavy Ions, Nuclear Instruments and Methods, 1975, vol. 131, pp. 437-440.
Koto and Tsujii, Future of Particle Therapy, Japanese Journal of Cancer Clinics, 2001, 47(1):95-98 [Lang.: Japanese], English abstract (http://sciencelinks.j12/jeast/article/200206/000020020601A05 I I 453 .nhn).
Kraft et al., Hadrontherapy in Oncology, U. Amaldi and Larrsson, editors Elsevier Science, 1994, 161 pages.
Krevet et al., Design of a Strongly Curved Superconducting Bending Magnet for a Compact Synchrotron Light Source, Advances in Cryogenic Engineering, 1988, vol. 33, pp. 25-32.
Laisne et al., The Orsay 200 MeV Synchrocyclotron, IEEE Transactions on Nuclear Science, Apr. 1979, NS-26(2):1919-1922.
Larsson, B., et al., "The High-Energy Proton Beam as a Neurosurgical Tool," Nature vol. 182, pp. 1222-1223 (1958).
Larsson, Biomedical Program for the Converted 200-MeV Synchrocyclotron at the Gustaf Werner Institute, Radiation Research, 1985, 104:S310-S318.
Lawrence et al., Heavy particles in acromegaly and Cushing's Disease, in Endocrine and Norendocrine Hormone Producing Tumors (Year Book Medical Chicago, 1973, pp. 29-61.
Lawrence et al., Successful Treatment of Acromegaly: Metabolic and Clinical Studies in 145 Patients, The Journal of Clinical Endrocrinology and Metabolism, Aug. 1970, 31(2), 21 pages.
Lawrence et al., Treatment of Pituitary Tumors, (Excerpta medica, Amsterdam/American Elsevier, New York, 1973, pp. 253-262.
Lawrence, J.H., Proton Irradiation of the Pituitary Cancer, vol. 10, pp. 795-798 (1957).
Lecroy et al., Viewing Probe for High Voltage Pulses, Review of Scientific Instruments USA, Dec. 1960, 31(12):1354.
Lin et al., Principles and 10 Year Experience of the Beam Monitor System at the PSI Scanned Proton Therapy Facility, Center for Proton Radiation Therapy, Paul Scherrer Institute, CH-5232, Villigen PSI, Switzerland, 2007, 21 pages.
Linfoot et al., Acromegaly, in Hormonal Proteins and Peptides, edited by C.H. Li, 1975, pp. 191-246.
Literature Author and Keyword Search, Feb. 14, 2005, 44 pages.
Literature Keyword Search, Jan. 24, 2005, 98 pages.
Literature Search and Keyword Search for Synchrocyclotron, Jan. 25, 2005, 68 pages.
Literature Search by Company Name/Component Source, Jan. 24, 2005, 111 pages.
Literature Search, Jan. 26, 2005, 37 pages.
Livingston, M.S., et al. A Capillary Ion Source for the Cyclotron, Review Science Instruments, vol. 10, p. 9. 63-67, (1939).
LLNL, UC Davis Team Up to Fight Cancer, Lawrence Livermore National Laboratory, Apr. 28, 2006, SF-06-04-02, Livermore, California, pp. 1-4.
Machine translation of JP11-028252A from jpo website Jul. 17, 2015.

(56) References Cited

OTHER PUBLICATIONS

Mandrillon, High Energy Medical Accelerators, EPAC 90, 2nd European Particle Accelerator Conference, Jun. 12-16, 1990, 2:54-58.

Marchand et al., IBA Proton Pencil Beam Scanning: an Innovative Solution for Cancer Treatment, Proceedings of EPAC 2000, Vienna, Austria, 3 pages.

Marti et al., High Intensity Operation of a Superconducting Cyclotron, Proceedings of the I 4the International Conference, Cyclotrons and Their Applications, Oct. 1995, pp. 45-48 (Oct. 1995).

Martin, Operational Experience with Superconducting Synchrotron Magnets Proceedings of the 1987 IEEE Particle Accelerator Conference, Mar. 16-19, 1987, vol. 3 of 3: 1379-1382.

Meote et al., ETOILE Hadrontherapy Project, Review of Design Studies Proceedings of EPAC 2002, 2002, pp. 2745-2747.

Miyamoto et al., Development of the Proton Therapy System, The Hitachi Hyoron, 79(10):775-775 779 (1997) [Lang: Japanese], English abstract (http://www.hitachi.com/rev/1998/revfeb98/rev4 706.htm).

Moignier, A. et al., Toward improved target conformity for two spot scanning proton therapy delivery systems using dynamic collimation, Medical Physics, 43:1421-1427 (2014).

Montelius et al., The Narrow Proton Beam Therapy Unit at the Svedberg Laboratory in Uppsala, ACTA Oncologica, 1991, 30:739-745.

Moser et al., Nonlinear Beam Optics with Real Fields in Compact Storage Rings, Nuclear Instruments & Methods in Physics Research/Section B, B30, Feb. 1988, No. 1, pp. 105-109.

Moyers et al., A Continuously Variable Thickness Scatterer for Proton Beams Using Self-compensating Dual Linear Wedges Loma Linda University Medical Center, Dept. of Radiation Medicine, Loma Linda, CA, Nov. 2, 1992, 21 pages.

National Cancer Institute Funding (Senate—Sep. 21, I 992} (wvw.tbomas.loc.gov/cgibin/querv/z?rl02:S21SE2-7I2 (2 pages).

Nicholson, Applications of Proton Beam Therapy, Journal of the American Society of Radiologic Technologists, May/Jun. 1996, 67(5): 439-441.

Nolen et al., The Integrated Cryogenic—Superconducting Beam Transport System Planned for MSU, Proceedings of the J21h International Conference on High-Energy Accelerators, Aug. 1983, pp. 549-551.

Norimine et al., A Design of a Rotating Gantry with Easy Steering for Proton Therapy, Proceedings of EPAC 2002, 2002, pp. 2751-2753.

Office Action for U.S. Appl. No. 14/137,854, 32 pages (dated Dec. 22, 2016).

Office Action for U.S. Appl. No. 14/137,854, 39 pages (dated Apr. 5, 2017).

Ogino, Takashi, Heavy Charged Particle Radiotherapy-Proton Beam, Division of Radiation Oncology, National Cancer Hospital East, Kashiwa, Japan, Dec. 2003, 7 pages.

Okumura et al., Overview and Future Prospect of Proton Radiotherapy, Japanese Journal of Cancer Clinics, 1997, 43(2):209-214 [Lang.: Japanese].

Okumura et al., Proton Radiotherapy Japanese Journal of Cancer and Chemotherapy, 1993, 10. 20(14):2149-2155[Lang.: Japanese].

Outstanding from Search Reports, Accelerator of Polarized Portons at Fermilab, 2005, 20 pages.

Paganetti et al., Proton Beam Radiotherapy—The State of the Art, Springer Verlag, Heidelberg, ISBN 3-540-00321-5, Oct. 2005,36 pages.

Palmer and Tollestrup, Superconducting Magnet Technology for Accelerators, Annual Review of Nuclear and Particle Science, 1984, vol. 34, pp. 247-284.

Patent Assignee and Keyword Searches for Synchrocyclotron, Jan. 25, 2005, 78 pages.

Patent Assignee Search Paul Scherrer Institute, Library Services at Fish & Richardson P.C., Mar. 20, 2007, 40 pages.

Patent Prior Art Search for 'Proton Therapy System', Library Services at Fish & Richardson P.C., Mar. 20, 2007, 46 pages.

Pavlovic, Beam-optics study of the gantry beam delivery system for light-ion cancer therapy, Nuclear Instruments and Methods in Physics Research, Section A, Nov. 1997, 399(2):439-454(16).

Pedroni and Enge, Beam optics design of compact gantry for proton therapy Medical & Biological Engineering & Computing, May 1995, 33(3):271-277.

Pedroni et al., A Novel Gantry for Proton Therapy at the Paul Scherrer Institute, Cycloctrons and Their Applications 2001: Sixteenth International Conference. AIP Conference Proceedings, 2001, 600:13-17.

Pedroni et al., The 200-MeV proton therapy project at the Paul Scherrer Institute: Conceptual design and practical realization, Medical Physics, Jan. 1995, 22(1):37-53.

Pedroni, Accelerators for Charged Particle Therapy: Performance Criteria from the User Point of View, Cyclotrons and their Applications, Proceedings of the 13th International Conference, Jul. 6-10, 1992, pp. 226-233.

Pedroni, E. and Jermann, M. "SGSMP: Bulletin Mar. 2002 Proscan Project, Progress Report on the PROSCAN Project of PSI," [online] retrieved from www.sgsmp.ch/protA23.htm, (5 pages) Mar. 2002.

Pedroni, Latest Developments in Proton Therapy Proceedings of EPAC 2000, pp. 240-244, 2000.

Pedroni, Status of Proton Therapy: results and future trends, Paul Scherrer Institute, Division of Radiation Medicine, 1994, 5 pages.

Peggs et al., A Survey of Hadron Therapy Accelerator Technologies, Particle Accelerator Conference, Jun. 25-29, 2008, 7 pages.

Potts et al., MPWP6-Therapy III: Treatment Aids and Techniques Medical Physics, Sep./Oct. 1988, 15(5):798.

Pourrahimi et al., Powder Metallurgy Processed Nb3Sn(Ta) Wire for High Field NMR magnets, IEEE Transactions on Applied Superconductivity, Jun. 1995, 5(2):1603-1606.

Prieels et al., The IBA State-of-the-Art Proton Therapy System, Performances and Recent Results, Application of Accelerators in Research and industry—Sixteenth Int'l Conj, American Institute of Physics, Nov. 1-5, 2000, 576:857-860.

Proiect of PSI [online] retrieved from www.sgsmp.ch/protA23.htm, Mar. 2002, 5 pages.

Rabin et al., Compact Designs for Comprehensive Proton Beam Clinical Facilities, Nuclear Instruments & Methods in Physics Research, Apr. 1989, Section B, vol. 40-41, Part II, pp. 1335-1339.

Research & Development Magazine, Proton Therapy Center Nearing Completion, Aug. 1999, 41(9):2 pages (www.rdmag.com).

Resmini,, Design Characteristics of the K=800 Superconducting Cyclotron at M.S.U., Cyclotron Laboratory, Michigan State University, East Lansing, Michigan 48824, IEEE Transaction on Nuclear Science, vol. NS-26, No. 2, Apr. 1979, 8 pages.

RetroSearch Berkeley 88-Inch Cyclotron 'RF' or 'Frequency Control', Jan. 21, 2005, 36 pages.

RetroSearch Berkeley 88-Inch Cyclotron, Jan. 24, 2005, 170 pages.

RetroSearch Bernard Gottschalk, Cyclotron, Beams, Compensated Upstream Modulator, Compensated Scatter, Jan. 21, 2005, 20 pages.

RetroSearch Cyclotron with 'RF' or 'Frequency Control', Jan. 21, 2005, 49 pages.

RetroSearch Gottschalk, Bernard, Harvard Cyclotron Wheel, Jan. 21, 2005, 20 pages.

RetroSearch Loma Linda University Beam Compensation, Jan. 21, 2005, 60 pages.

RetroSearch Loma Linda University, Beam Compensation Foil Wedge, Jan. 21, 2005, 15 pages.

Revised Patent Keyword Search, Jan. 25, 2005, 86 pages.

Rifuggiato et, al., Status Report of the LNS Superconducting Cyclotron Nukleonika, 2003, 48:SI31-SI34, Supplement 2.

Rode, Tevatron Cryogenic System, Proceedings of the 12th International Conference on Highenergy Accelerators, Fermilab, Aug. 11-16, 1983, pp. 529-535.

Salzburger et al., Superconducting Synchrotron Magnets Supraleitende Synchrotronmagnete, NTiS, 155 pages (Oct. 1975).

Schillo et al,. Compact Superconducting 250 MeV Proton Cyclotron for the PSI Proscan Proton Therapy Project, Cyclotrons and Their Applications 2001, Sixteenth International Conference, 2001, pp. 37-39.

(56) References Cited

OTHER PUBLICATIONS

Schneider et al., Nevis Synchrocyclotron Conversion Program—RF System, IEEE Transactions on Nuclear Science USA, Jun. 1969, ns 16(3): 430-433.
Schneider et al., Superconducting Cyclotrons, IEEE Transactions on Magnetics, vol. MAG-11, No. 2, Mar. 1975, New York, pp. 443-446.
Schreuder et al., The Non-orthogonal Fixed Beam Arrangement for the Second Proton Therapy Facility at the National Accelerator Centre, Application of Accelerators in Research and Industry, American Institute of Physics, Proceedings of the Fifteenth International Conference, Nov. 1998, Part Two, pp. 963-966.
Schreuder, Recent Developments in Superconducting Cyclotrons, Proceedings of the 1995 Particle Accelerator Conference, May 1-5, 1995, vol. 1, pp. 317-321.
Schubert and Blosser, Conceptual Design of a High Field Ultra-Compact Cyclotron for Nuclear Physics Research, Proceedings of the 1997 Particle Accelerator Conference, May 12-16, 1997, vol. 1, 3 pp. 1060-1062.
Schubert, Extending the Feasibility Boundary of the Isochronous Cyclotron, Dissertation submitted to Michigan State University, 1997, Abstract http://adsabs.harvard.edu/abs/1998PhDT ....... 147S.
Shelaev et al., Design Features of a Model Superconducting Synchrotron of JINR, Proceedings of the 12th International Conference on High-energy Accelerators, Aug. 11-16, 1983, pp. 416-418.
Shintomi et. Al, Technology and Materials for the Superconducting Super Collider (SSC) Project, [Lang.: Japanese], The Iron and Steel Institute of Japan 00211575, 78(8): 1305-1313, 1992, http://ci.nii.ac.ip/naid/1 1 0001493249/en/.
Siemens A.G., Erlangen (West Germany). Abteilung Technische Physik, Report No. BMFT-FB-T-75-25, Oct. 1975, p. 147, Journal Announcement: GRAI7619; STAR1415, Subm-Sponsored by Bundesmin. Fuer Forsch. U. Technol. In German; English Summary.
Sisterson, Clinical use of proton and ion beams from a world-wide perspective, Nuclear Instruments and Methods in Physics Research, Section B, 1989, 40-41:1350-1353.
Sisterson, World Wide Proton Therapy Experience in 1997, The American Institute of Physics, Applications of Accelerators in Research and Industry, Proceedings of the Fifteenth International Conference, Part Two, Nov. 1998, pp. 959-962.
Slater et al., Developing a Clinical Proton Accelerator Facility: Consortium-Assisted Technology Transfer, Conference Record of the 1991 IEEE Particle Accelerator Conference: Accelerator Science and Technology, vol. I, May 6-9, 1991, pp. 532-536.
Slater et al., Development of a Hospital-Based Proton Beam Treatment Center, International Journal of Radiation Oncology Biology Physics, Apr. 1988, 14(4):761-775.
Smith et al., The Northeast Proton Therapy Center at Massachusetts General Hospital Journal of Brachytherapy International, Jan. 1997, pp. 137-139.
Snyder and Marti, Central region design studies for a proposed 250 MeV proton cyclotron, Nuclear Instruments and Methods in Physics Research, Section A, 1995, vol. 355, pp. 618-623.
Soga, Progress of Particle Therapy in Japan, Application of Accelerators in Research and Industry, American Institute of Physics, Sixteenth International Conference, Nov. 2000, pp. 869-872.
Source Search "Cites of U.S. and Foreign Patents/Published applications in the name of Mitsubishi Denki Kabushiki Kaisha and Containing the Keywords (Proton and Synchrocyclotron)," Jan. 2005, 8 pages.
Spiller et al., The GSI Synchrotron Facility Proposal for Acceleration of High Intensity Ion and Proton Beams Proceedings of the 2003 Particle Accelerator Conference, May 12-16, 2003, vol. 1, pp. 589-591.
Stanford et al., Method of Temperature Control in Microwave Ferroelectric Measurements, Sperry Microwave Electronics Company, Clearwater, Florida, Sep. 19, 1960, 1 page.
Superconducting Cyclotron Contract awarded by Paul Scherrer Institute (PSI), Villigen, Switzerland, http://www.accel.de/News/superconducting_ cyclotron_ contract.htm, Jan. 2009, 1 page.
Tadashi et al., Large superconducting super collider (SSC) in the planning and materials technology,78(8):1305-1313, The Iron and Steel Institute of Japan 00211575, Aug. 1992.
Takada, Conceptual Design of a Proton Rotating Gantry for Cancer Therapy, Japanese Journal of Medical Physics, 1995, 15(4):270-284.
Takayama et al., Compact Cyclotron for Proton Therapy, Proceedings of the 81h Symposium on Accelerator Science and Technology, Japan, Nov. 25-27, 1991, pp. 380-382.
Teng, The Fermilab Tevatron, Coral Gables 1981, Proceedings, Gauge Theories, Massive Neutrinos, and Proton Decay, 1981, pp. 43-62.
The Davis 76-Inch Isochronous Cyclotron, Beam On: Crocker Nuclear Laboratory, University of California, 2009, 1 page.
The Journal of Practical Pharmacy,1995, 46(1):97-103 [Japanese].
The K100 Neutron-therapy Cyclotron, National Superconducting Cyclotron Laboratory at Michigan State University (NSCL ), retrieved from: http://www.nscl.msu.edu/tech/accelerators/kl 00, Feb. 2005, 1 page.
The K250 Proton therapy Cyclotron, National Superconducting Cyclotron Laboratory at Michigan State University (NSCL), retrieved from: http://www.nscl.msu.edu/tech/accelerators/k.250.html, Feb. 2005, 2 pages.
The K250 Proton-therapy Cyclotron Photo Illustration, National Superconducting Cyclotron Laboratory at Michigan State University (NSCL), retrieved from: http://www.nscl.msu.edu/media/image/ experimental-equipment-technology /25 0 .html, Feb. 2005, 1 page.
Tilly, et al., "Development and verification of the pulsed scanned proton beam at The Svedberg 254 Laboratory in Uppsala", Physics in Medicine and Biology, Phys. Med. Biol. 52, pp. 2741-2454, 2007.
Tilly, et al., Development and verification of the pulsed scanned proton beam at The Svedberg Laboratory in Uppsala, Physics in Medicine and Biology, Phys. Med. Biol. 52, pp. 2741-2454, 2007.
Tobias, C.A., et al., Pituitary Irradiation with High-Energy Proton Beams A Preliminary Report, Cancer Research, vol. 18, No. 2, pp. 121-134 (1958).
Tom, The Use of Compact Cyclotrons for Producing Fast Neutrons for Therapy in a Rotatable Isocentric Gantry, IEEE Transaction on Nuclear Science, Apr. 1979, 26(2):2294-2298.
Torikoshi, M. et al., Irradiation System for HIMAC, J. Radiat. Res, 48: Suppl. A15-A25 (2007).
Toyoda, Proton Therapy System, Sumitomo Heavy Industries, Ltd., 2000, 5 pages.
Trinks et. al., The Tritron: A Superconducting Separated-Orbit Cyclotron, Nuclear Instruments and Methods in Physics Research, Section A, 1986, vol. 244, pp. 273-282.
Tsuji, The Future and Progress of Proton Beam Radiotherapy, Journal of Japanese Society for Therapeutic Radiology and Oncology, 1994, 6(2):63-76.
U.S. Appl. No. 13/830,792, filed Mar. 14, 2013.
U.S. Appl. No. 13/949,459, filed Jul. 24, 2013.
U.S. Appl. No. 61/676,377, filed Jul. 27, 2012.
UC Davis School of Medicine, Unlikely Partners Turn Military Defense into Cancer Offense, Current Issue Summer 2008, Sacramento, California, pp. 1-2.
Umegaki et al., Development of an Advanced Proton Beam Therapy System for Cancer Treatment Hitachi Hyoron, 2003, 85(9):605-608 [Lang.: Japanese], English abstract, http://www.hitachi.com/ICSFiles/afieldfile/2004/06/0 I/r2003 _ 04_ I 04.pdf or http://www.hitachi.com/rev/archive/2003/2005649_12606.html (full text) [Hitachi, 52( 4), Dec. 2003].
Umezawa et al., Beam Commissioning of the new Proton Therapy System for University of Tsukuba, Proceedings of the 2001 Particle Accelerator Conference, vol. 1, Jun. 18-22, 2001, pp. 648-650.
van Steenbergen, Superconducting Synchroton Development at BNL, Proceedings of the 8th International Conference on High-Energy Accelerators CERN 1971, 1971, pp. 196-198.

(56) References Cited

OTHER PUBLICATIONS van Steenbergen, The CMS, a Cold Magnet Synchrotron to Upgrade the Proton Energy Range of the BNL Facility, IEEE Transactions on Nuclear Science, Jun. 1971, 18(3):694-698.
Vandeplassche et al., 235 MeV Cyclotron for MGH's Northeast Proton Therapy Center (NPTC): Present Status, EPAC 96, Fifth European Partical Accelerator Conference, vol. 3, Jun. 10-14, 1996, pp. 2650-2652.
Vorobiev et al., Concepts of a Compact Achromatic Proton Gantry with a Wide Scanning Field, Nuclear Instruments and Methods in Physics Research, Section A., 1998, 406(2):307-310.
Vrenken et al., A Design of a Compact Gantry for Proton Therapy with 2D-Scanning, Nuclear Instruments and Methods in Physics Research, Section A, 1999, 426(2):618-624.
Wikipedia, Cyclotron http://en.wikipedia.org/wiki/Cyclotron (originally visited Oct. 6, 2005, revisited Jan. 28, 2009), 7 pages.
Wikipedia, Synchrotron http://en.wikipedia.org/wiki/Synchrotron (originally visited Oct. 6, 2005, revisited Jan. 28, 2009), 7 pages.
Worldwide Patent Assignee Search, Jan. 24, 2005, 224 pages.
Worldwide Patent Keyword Search, Jan. 24, 2005, 94 pages.
Written Opinion for PCT/US2016/048037, 12 pages (dated Feb. 6, 2017).
Wu, Conceptual Design and Orbit Dynamics in a 250 MeV Superconducting Synchrocyclotron, Ph.D. Dissertation, Michigan State University, Department of Physics and Astronomy, 1990, 172 pages.
York et al., Present Status and Future Possibilities at NSCL-MSU, EP AC 94, Fourth European Particle Accelerator Conference, pp. 554-556, Jun. 1994.
York et al., The NSCL Coupled Cyclotron Project—Overview and Status,Proceedings of the Fifteenth International Conference on Cyclotrons and their Avvlications, Jun. 1998, pp. 687-691.
Yudelev et al., Hospital Based Superconducting Cyclotron for Neutron Therapy: Medical Physics Perspective, Cyclotrons and their applications 2001, 16th International Conference. American Institute of Physics Conference Proceedings, vol. 600, May 13-17, 2001, pp. 40-43.
Zherbin et al., Proton Beam Therapy at the Leningrad Synchrocyclotron (Clinicomethodological Aspects and Therapeutic Results), Aug. 1987, 32(8):17-22, (German with English abstract on pp. 21-22).
Office Action for U.S. Appl. No. 14/137,854, 24 pages (dated Oct. 23, 2017).
Office Action for U.S. Appl. No. 14/937,048, 94 pages (dated Oct. 13, 2017).
Office Action for U.S. Appl. No. 15/438,544, 27 pages (dated Oct. 12, 2017).
First Office Action (English translation) for JP2016-541203, 10 pages (dated Jul. 31, 2017).
First Office Action (Japanese translation) for JP2016-541203, 7 pages (dated Jul. 31, 2017).
First Office Action for CN201480070002.6 (Chinese translation), 9 pages (dated Apr. 11, 2018).
First Office Action for CN201480070002.6 (English translation), 12 pages (dated Apr. 11, 2018).
International Search Report for PCT/US2017/067677 (High-Speed Energy Switching, filed Dec. 20, 2017), issued by ISA/US, 4 pages (dated Apr. 30, 2018).
Written Opinion for PCT/US2017/067677 (High-Speed Energy Switching, filed Dec. 20, 2017), issued by ISA/US, 7 pages (dated Apr. 30, 2018).
Communication under Rule 71(3) EPC for EP14830919.8, 113 pages (dated May 2, 2018).
Final Office Action for U.S. Appl. No. 15/438,854, 30 pages (dated Nov. 28, 2018).
Final Office Action for U.S. Appl. No. 15/438,863, 30 pages (dated Nov. 28, 2018).
Second Office Action (Chinese translation) for CN201480070002.6, 3 pages (dated Jan. 11, 2019).
Second Office Action (English translation) for CN201480070002.6, 4 pages (dated Jan. 11, 2019).
File History of U.S. Appl. No. 61/883,631, filed Sep. 27, 2013.
Final Office Action for U.S. Appl. No. 14/937,048, 52 pages (dated Mar. 1, 2018).
Final Office Action for U.S. Appl. No. 15/438,544, 31 pages (dated Mar. 1, 2018).
Final Office Action for U.S. Appl. No. 15/438,544, 47 pages (dated Apr. 29, 2019).
Gustafsson, A. et al., Simultaneous optimization of dynamic multileaf collimation and scanning patterns or compensation filters using a generalized pencil beam algorithm, Med. Phys., 22(7):1141-1156 (1995).
Office Action for U.S. Appl. No. 15/438,854, 27 pages (dated May 8, 2019).
Office Action for U.S. Appl. No. 15/438,863, 20 pages (dated May 8, 2019).
Office Action for U.S. Appl. No. 14/937,048, 56 pages (dated Aug. 15, 2018).
Office Action for U.S. Appl. No. 14/937,048, 57 pages (dated May 9, 2019).

\* cited by examiner

ENERGY DEGRADER ENABLING HIGH-SPEED ENERGY SWITCHING

CROSS-REFERENCE TO RELATED APPLICATION

This application is a continuation-in-part of, and claims priority to, U.S. patent application Ser. No. 14/137,854, which was filed on Dec. 13, 2013, and which is titled "Collimator and Energy Degrader". U.S. patent application Ser. No. 14/137,854 is incorporated herein by reference.

TECHNICAL FIELD

This disclosure relates generally to an energy degrader that is configurable to change the energy of a particle beam.

BACKGROUND

Particle therapy systems use an accelerator to generate a particle beam for treating afflictions, such as tumors. In operation, particles are accelerated in orbits inside a cavity in the presence of a magnetic field, and are removed from the cavity through an extraction channel. A magnetic field regenerator generates a magnetic field bump near the outside of the cavity to distort the pitch and angle of some orbits so that they precess towards, and eventually into, the extraction channel. A beam, comprised of the particles, exits the extraction channel.

A scanning system is down-beam of the extraction channel. In this context, "down-beam" means closer to an irradiation target (here, relative to the extraction channel). The scanning system moves the beam across at least part of the irradiation target to expose various parts of the irradiation target to the beam. For example, to treat a tumor, the particle beam may be "scanned" over different cross-sections of the tumor. An energy degrader changes the energy of the particle beam to reach the different cross-sections of the tumor.

SUMMARY

An example particle therapy system comprises: a particle accelerator to output a particle beam; and an energy degrader that is controllable to pass the particle beam to an irradiation target. At least part of the energy degrader may be controllable to move during passage of the particle beam to the irradiation target. The example particle therapy system may include one or more of the following features, either alone or in combination.

The energy degrader may comprise plates (e.g., multiple plates) that are movable. The multiple plates may comprise a first plate and a second plate that are controllable to move during passage of the particle beam. The second plate may be controllable to trail the first plate during movement, or the first plate may be controllable to trail the second plate during movement.

The example particle therapy system may comprise a scanner that is controllable to move the particle beam in one or more dimensions relative to the irradiation target. At least one of the energy degrader or the scanner may be controllable so that, during movement of the first plate and the second plate, the particle beam passes through the first plate but not the second plate or the second plate but not the first plate. At least one of the energy degrader or the scanner may be controllable so that, during movement of the first plate and the second plate, the particle beam passes through both the first plate and the second plate. Movement of the particle beam across a plate among the multiple plates may be limited to movement outside of a predefined distance from an edge of the plate.

The energy degrader may comprise multiple plates comprising a first plate and a second plate that are controllable to move during passage of the particle beam. During movement of the first plate and the second plate, the first plate and the second plate may move from a starting position to an ending position. The particle beam may be controllable to move from a location towards the ending position such that the particle beam passes through both the first plate and the second plate or through only one of the first plate or the second plate. The particle beam may be controllable to move from a location towards the starting position such that the particle beam passes through both the first plate and the second plate or through only one of the first plate or the second plate.

The multiple plates of the energy degrader may comprise one or more first plates and one or more second plates. The one or more first plates and the one or more second plates may be controllable to move relative to the particle beam. Each of one or more first plates may have a thickness that is less than thicknesses of the one or more second plates. A first plate among the one or more first plates may have a thickness that is a fraction of a thickness of each of the one or more second plates. For example, the first plate may have a thickness that is half of a thickness of each of the one or more second plates.

Control over movement of multiple plates of the energy degrader may comprise sequencing movement of the multiple plates so that each of multiple layers of the irradiation target is subjected to the particle beam. Control over movement of the multiple plates may comprise sequencing movement of the multiple plates so that the multiple layers of the irradiation target are treated with the particle beam non-sequentially. Control over movement of the multiple plates may comprise sequencing movement of the multiple plates so that an energy of the particle beam corresponds to a location of each of multiple layers of the irradiation target.

The example particle therapy may comprise an aperture that is controllable to trim spots of the particle beam. The aperture may be between the irradiation target and the energy degrader. The energy degrader may comprise one or more plates that are movable relative to the irradiation target during passage of the particle beam. Each of the one or more plates may have a size that is less than a size of a radiation field.

An example particle therapy system may comprise: a synchrocyclotron to produce a particle beam; a scanner to move the particle beam in one or more dimensions relative to an irradiation target; and an energy degrader that is between the scanner and the irradiation target. The energy degrader may comprise multiple plates that are movable relative to a path of the particle beam. The multiple plates may each be controllable to move while in the path of the particle beam and during movement of the particle beam. An aperture may be between the energy degrader and the irradiation target. The aperture may be controllable to trim the particle beam prior to the particle beam reaching the irradiation target. The example particle therapy system may include one or more of the following features, either alone or in combination.

The example particle therapy system may comprise an outer gantry on which the synchrocyclotron is mounted, with the outer gantry being configured to move the synchrocyclotron at least partly around the irradiation target; and an inner gantry, within a sweep of the outer gantry, with the inner gantry comprising a nozzle on which the energy degrader is mounted, and with the inner gantry being configured to move the energy degrader based on movement of the outer gantry.

The multiple plates may comprise a first plate and a second plate that are controllable to move in a first direction and a second direction during passage of the particle beam. The first direction may be from a starting position to an ending position, and the second direction may be from the ending position to the starting position. At least one of the scanner or the energy degrader may be controllable so that, during movement of the first plate and the second plate in the first direction, the particle beam passes through either the first plate only or the second plate only or through both the first plate and the second plate. At least one of the scanner or the energy degrader may be controllable so that, during movement of the first plate and the second plate in the second direction, the particle beam passes through either the first plate only or the second plate only or through both the first plate and the second plate.

The first plate and the second plate may be controllable to move separately during application of the particle beam. The second plate may be controllable to trail the first plate during movement, or the first plate may be controllable to trail the second plate during movement. At least one of the energy degrader or the scanner may be controllable so that movement of the particle beam during movement of the first plate and the second plate is such that the particle beam passes through the first plate but not the second plate or through the second plate but not the first plate. At least one of the energy degrader or the scanner may be controllable so that movement of the particle beam during movement of the first plate and the second plate is such that the particle beam passes through both the first plate and the second plate. Movement of the particle beam across a plate among the multiple plates may be limited to movement outside of a distance from an edge of the plate.

During movement of the first plate and the second plate, the first plate and the second plate may move from a starting position to an ending position. The scanner may be controllable to move the particle beam from a location towards the ending position such that the particle beam passes through both the first plate and the second plate or through only one of the first plate or the second plate. The scanner may be controllable to move the particle beam from a location towards the starting position such that the particle beam passes through both the first plate and the second plate or through only one of the first plate or the second plate. The multiple plates may comprise one or more first plates and one or more second plates, with the one or more first plates and one or more second plates being controllable to move during application of the particle beam, and with each of the one or more first plates having a thickness that is less than thicknesses of the one or more second plates. Each of the multiple plates may have a size that is less than a size of a radiation (or beam) field.

An example particle therapy system may be configured to apply a particle beam to an irradiation target. The example particle therapy system comprises a scanner to move the particle beam in one or more dimensions relative to the irradiation target; and an energy degrader comprising elements that are controllable to move during movement of the particle beam. The energy degrader is for passing the particle beam prior to application of the particle beam to the irradiation target. The example particle therapy system may include one or more of the following features, either alone or in combination.

The elements may comprise plates that are controllable to move in a sequence to change an energy of the particle beam so that different layers of the irradiation target are subjected to the particle beam. The elements may comprise a first plate and a second plate, with both the first plate and the second plate being controllable to move during movement of the particle beam. At least one of the energy degrader or the scanner may be controllable so that the particle beam passes through the first plate but not the second plate or through the second plate but not the first plate during at least part of the movement of the first plate and the second plate. At least one of the energy degrader or the scanner may be controllable so that the particle beam passes through both the first plate and the second plate during at least part of the movement of the first plate and the second plate. At least one of the energy degrader or the scanner may be controllable so that the particle beam does not pass within at least a distance from an edge of at least one of the elements. The distance may be based on a distribution of particles in a spot representing a cross-section of the particle beam at the at least one of the elements.

The elements may be controllable to move in at least one of a first direction or a second direction during movement of the particle beam, with the first direction being from a starting position of the elements to an ending position of the elements, and with the second direction being from the ending position to the starting position. At least some of the elements may be controllable to move separately during movement of the particle beam. At least some of the elements may be controllable to move together during movement of the particle beam. Each of the multiple elements may have a size that is less than a size of a radiation field.

An example particle therapy system comprises a particle accelerator to output a particle beam; and a scanning system for the particle accelerator to scan the particle beam across at least part of an irradiation target. The scanning system is configured to scan the particle beam in two dimensions that are at an angle relative to a direction of the particle beam. A structure defines an edge. The structure is controllable to move in the two dimensions relative to the irradiation target such that at least part of the structure is between at least part of the particle beam and the irradiation target. The structure comprises a material that inhibits transmission of the particle beam. The example particle therapy system may include one or more of the following features, either alone or in combination.

The structure may be rotatable at least in the two dimensions so that the edge can be moved between different parts of the irradiation target and the particle beam. The edge may comprise a curve that has a radius that varies on at least one side of the structure. The curve may be a French curve. The structure may define an aperture and the edge may comprise an edge of the aperture. The structure may be movable to track a direction of the particle beam. The structure may comprise multiple elements that are adjustable to vary a size of the edge. The multiple elements may comprise fingers that are individually movable relative to the irradiation target.

The structure may be part of a collimator system. The structure may comprise a first structure in the collimator system and the edge may comprise a first edge. The collimator system may comprise a second structure comprising a second edge. The first edge and the second edge may be controllable to move along different edges of the irradiation target.

The scanning system may comprise at least one magnet to control movement of the particle beam to scan the particle beam. The at least one magnet may be for generating a magnetic field in response to applied current. The magnetic field may affect the movement.

The scanning system may be configured to scan the particle beam more quickly in interior sections of the irradiation target than at edges of the irradiation target. The particle beam may be movable within an area of a plane at a location of the structure. The structure may have an area that is less than the area of the plane. The structure may have an area that is less than half the area of the plane. The structure may have an area that is less than a quarter the area of the plane. The structure may have an area that is less than an eighth the area of the plane. The structure may have an area that is less than ten times a cross-sectional area of the particle beam.

The scanning system may be configured to scan the particle beam from different incident angles. The structure may be controllable to move based on movement of the particle beam as the particle beam is scanned from different incident angles. The scanning system may comprise: a magnet to affect a direction of the particle beam to scan the particle beam across at least part of an irradiation target; and a degrader to change an energy of the beam prior to output of the particle beam to the irradiation target, where the degrader is down-beam of the magnet relative to the particle accelerator. The particle accelerator may be a variable-energy device.

The particle accelerator may comprise: a voltage source to provide a radio frequency (RF) voltage to a cavity to accelerate particles from a plasma column, where the cavity has a magnetic field causing particles accelerated from the plasma column to move orbitally within the cavity; an extraction channel to receive the particles accelerated from the plasma column and to output the received particles from the cavity; and a regenerator to provide a magnetic field bump within the cavity to thereby change successive orbits of the particles accelerated from the plasma column so that, eventually, particles output to the extraction channel. The magnetic field may be between 4 Tesla (T) and 20 T and the magnetic field bump is at most 2 Tesla.

An example particle therapy system comprises: a particle accelerator to output a particle beam; and a scanning system to receive the particle beam from the particle accelerator and to perform scanning of at least part of an irradiation target with the particle beam. The scanning system comprises a structure defining an edge. The structure is controllable to move in the two dimensions and to move based on movement of the particle beam so that the edge is between at least part of the particle beam and the irradiation target. The structure comprises a material that inhibits transmission of the particle beam. The example system also comprises a gantry on which the particle accelerator and the scanning system are mounted. The gantry may be configured to move the particle accelerator and the scanning system around the irradiation target.

An example particle therapy system comprises: a synchrocyclotron to output a particle beam; a magnet to affect a direction of the particle beam to move the particle beam across a cross-section of an irradiation target; a degrader to change an energy of the particle beam prior to moving the particle beam across the cross-section of the irradiation target, where the degrader is down-beam of the magnet relative to the synchrocyclotron; and one or more processing devices to control movement of the degrader so that the degrader at least partly tracks movement of the particle beam at an irradiation plane. The example particle therapy system may include one or more of the following features, either alone or in combination.

The particle beam may be movable within an area of a plane at a location of the degrader. The degrader may have an area that is less than the area of the plane. The degrader may comprise multiple pieces, with each piece comprised of beam-energy absorbing material, and with each piece being movable into a path of the particle beam. The one or more processing devices may be programmed to receive an energy of the particle beam to apply to the irradiation target, and to move one or more of the pieces of the beam-energy absorbing material into the path of the particle beam so that a resulting energy of the particle beam approximates the energy of the particle beam to apply to the irradiation target. The one or more processing devices may be programmed to control movement of the one or more pieces of the beam-energy absorbing material to at least partly track movement of the particle beam.

The degrader may have an area that is less than half the area of the plane. The degrader may have an area that is less than one-quarter the area of the plane. The particle beam has a spot size at a location of the degrader; and the degrader may have an area that is less than ten times an area of the spot size. The degrader may have an area that is less than twice an area of the spot size.

The particle therapy system may comprise memory to store a treatment plan. The treatment plan may comprise information to define a scanning pattern for the irradiation target. The scanning pattern may define movement of the particle beam in the two dimensions and movement of the degrader so that the degrader at least partly tracks movement of the particle beam.

The synchrocyclotron may comprise: a voltage source to provide a radio frequency (RF) voltage to a cavity to accelerate particles from a plasma column, where the cavity has a magnetic field causing particles accelerated from the plasma column to move orbitally within the cavity; an extraction channel to receive the particles accelerated from the plasma column and to output the received particles from the cavity as part of the particle beam; and a regenerator to provide a magnetic field bump within the cavity to thereby change successive orbits of the particles accelerated from the plasma column so that, eventually, particles output to the extraction channel. The magnetic field may be between 4 Tesla (T) and 20 T and the magnetic field bump may be at most 2 Tesla, and the synchrocyclotron may be a variable-energy device.

The magnet and the degrader may be part of a scanning system. The particle therapy system may comprise a gantry on which the synchrocyclotron and the scanning system are mounted. The gantry may be configured to move the synchrocyclotron and the scanning system around the irradiation target.

The scanning system may be a raster scanning system, a spot scanning system, or any other type of scanning system An example particle therapy system may comprise a particle accelerator to output a particle beam; and a scanning system to receive the particle beam from the synchrocyclotron and to perform scanning of at least part of an irradiation target with the particle beam. The scanning system may comprise a degrader to change an energy of the particle beam prior to scanning the at least part of the irradiation target. The degrader may be down-beam of the magnet relative to the synchrocyclotron. The example particle therapy system may comprise one or more processing devices to control movement of the degrader so that the degrader at least partly tracks movement of the particle beam during; and a gantry on which the particle accelerator and the scanning system are mounted. The gantry may be configured to move the synchrocyclotron and the scanning system around the irradiation target. The example particle therapy system may include one or more of the following features, either alone or in combination.

The particle beam may be movable within an area of a plane at a location of the degrader. The degrader may have an area that is less than the area of the plane. The degrader may comprise multiple pieces, with each piece comprised of beam-energy absorbing material, and with each piece being movable into a path of the particle beam. The one or more processing devices may be programmed to receive an energy of the particle beam to apply to the irradiation target, and to move one or more of the pieces of the beam-energy absorbing material into the path of the particle beam so that a resulting energy of the particle beam approximates the energy of the particle beam to apply to the irradiation target. The one or more processing devices may be programmed to control movement of the one or more pieces of the beam-energy absorbing material to at least partly track movement of the particle beam.

The degrader may have an area that is less than half the area of the plane. The degrader may have an area that is less than one-quarter the area of the plane. The particle beam has a spot size at a location of the degrader, and the degrader may have an area that is less than ten times an area of the spot size. The degrader may have an area that is less than twice an area of the spot size. The particle accelerator may be a variable-energy synchrocyclotron.

An example proton therapy system may include the foregoing particle accelerator and scanning system; and a gantry on which the particle accelerator and scanning system are mounted. The gantry is rotatable relative to a patient position. Protons are output essentially directly from the particle accelerator and through the scanning system to the position of an irradiation target, such as a patient. The particle accelerator may be a synchrocyclotron.

Two or more of the features described in this disclosure, including those described in this summary section, may be combined to form implementations not specifically described herein.

Control of the various systems described herein, or portions thereof, may be implemented via a computer program product that includes instructions that are stored on one or more non-transitory machine-readable storage media, and that are executable on one or more processing devices. The systems described herein, or portions thereof, may be implemented as an apparatus, method, or electronic system that may include one or more processing devices and memory to store executable instructions to implement control of the stated functions.

The details of one or more implementations are set forth in the accompanying drawings and the description below. Other features, objects, and advantages will be apparent from the description and drawings, and from the claims.

DESCRIPTION OF THE DRAWINGS

Like reference symbols in the various drawings indicate like elements.

DETAILED DESCRIPTION

Figure 1:
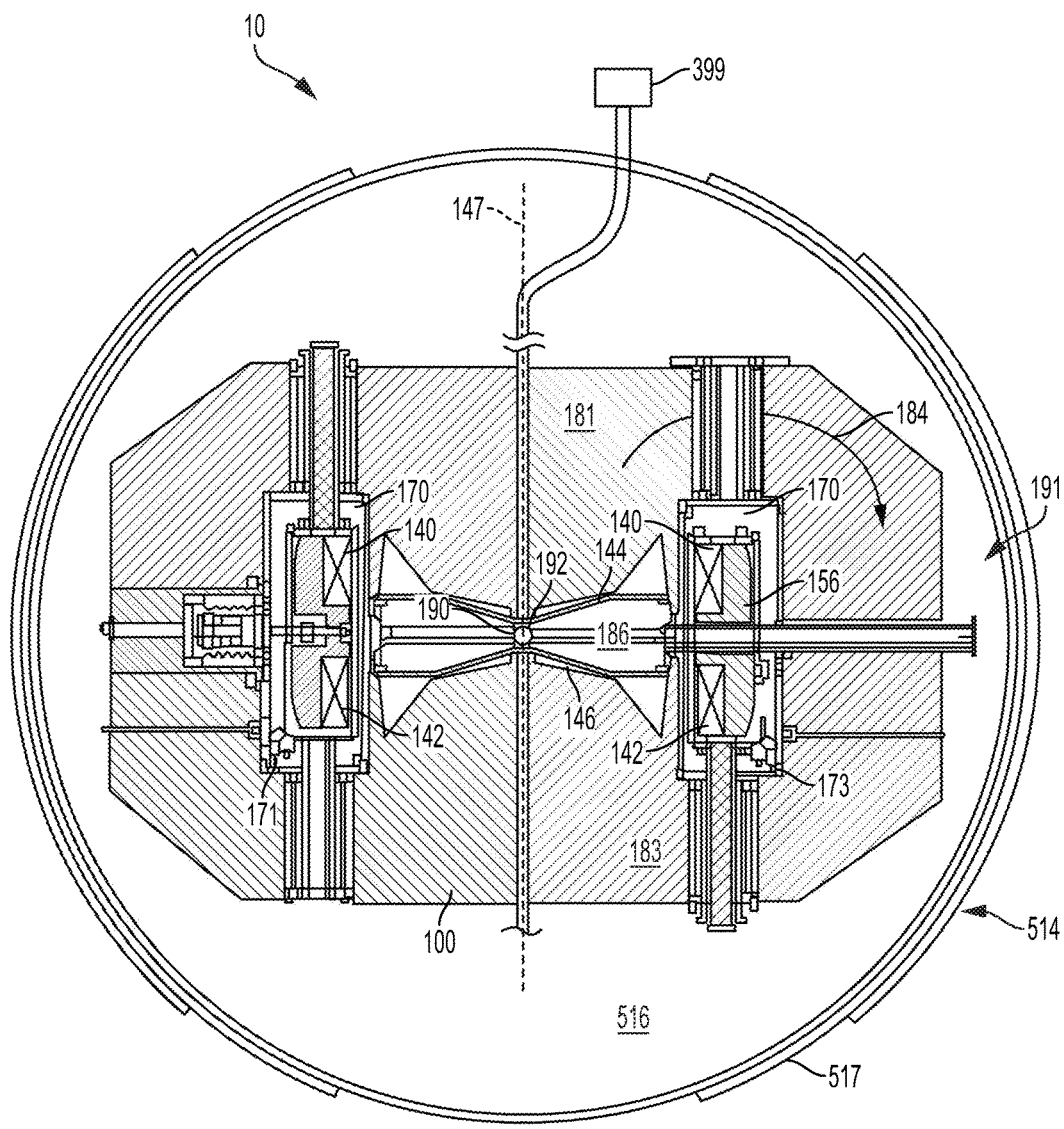
FIGS. 1 and 2 are a cross-sectional views of an example synchrocyclotron configuration for use in a particle therapy system.

Described herein is an example of a particle accelerator for use in a system, such as a proton or ion therapy system. The example particle therapy system includes a particle accelerator—in this example, a synchrocyclotron—mounted on a gantry. The gantry enables the accelerator to be rotated around a patient position, as explained in more detail below. In some implementations, the gantry is steel and has two legs mounted for rotation on two respective bearings that lie on opposite sides of a patient. The particle accelerator is supported by a steel truss that is long enough to span a treatment area in which the patient lies and that is attached at both ends to the rotating legs of the gantry. As a result of rotation of the gantry around the patient, the particle accelerator also rotates.

In an example implementation, the particle accelerator (e.g., the synchrocyclotron) includes a cryostat that holds one or more superconducting coils, each for conducting a current that generates a magnetic field (B). In this example, the cryostat uses liquid helium (He) to maintain each coil at superconducting temperatures, e.g., 4° Kelvin (K). Magnetic yokes or smaller magnetic pole pieces are located inside the cryostat, and define a cavity in which particles are accelerated.

In this example implementation, the particle accelerator includes a particle source (e.g., a Penning Ion Gauge—PIG source) to provide a plasma column to the cavity. Hydrogen gas is ionized to produce the plasma column. A voltage source provides a radio frequency (RF) voltage to the cavity to accelerate pulses of particles from the plasma column.

As noted, in an example, the particle accelerator is a synchrocyclotron. Accordingly, the RF voltage is swept across a range of frequencies to account for relativistic effects on the particles (e.g., increasing particle mass) when accelerating particles from the plasma column. The magnetic field produced by running current through a superconducting coil causes particles accelerated from the plasma column to accelerate orbitally within the cavity. In other implementations, a particle accelerator other than a synchrocyclotron may be used. For example, a cyclotron, a synchrotron, a linear accelerator, and so forth may be substituted for the synchrocyclotron described herein.

In the synchrocyclotron, a magnetic field regenerator ("regenerator") is positioned near the outside of the cavity (e.g., at an interior edge thereof) to adjust the existing magnetic field inside the cavity to thereby change locations (e.g., the pitch and angle) of successive orbits of the particles accelerated from the plasma column so that, eventually, the particles output to an extraction channel that passes through the cryostat. The regenerator may increase the magnetic field at a point in the cavity (e.g., it may produce a magnetic field "bump" at an area of the cavity), thereby causing each successive orbit of particles at that point to precess outwardly toward the entry point of the extraction channel until it reaches the extraction channel. The extraction channel receives particles accelerated from the plasma column and outputs the received particles from the cavity as a particle beam.

The superconducting ("main") coils can produce relatively high magnetic fields. The magnetic field generated by a main coil may be within a range of 4 T to 20 T or more. For example, a main coil may be used to generate magnetic fields at, or that exceed, one or more of the following magnitudes: 4.0 T, 4.1 T, 4.2 T, 4.3 T, 4.4 T, 4.5 T, 4.6 T, 4.7 T, 4.8 T, 4.9 T, 5.0 T, 5.1 T, 5.2 T, 5.3 T, 5.4 T, 5.5 T, 5.6 T, 5.7 T, 5.8 T, 5.9 T, 6.0 T, 6.1 T, 6.2 T, 6.3 T, 6.4 T, 6.5 T, 6.6 T, 6.7 T, 6.8 T, 6.9 T, 7.0 T, 7.1 T, 7.2 T, 7.3 T, 7.4 T, 7.5 T, 7.6 T, 7.7 T, 7.8 T, 7.9 T, 8.0 T, 8.1 T, 8.2 T, 8.3 T, 8.4 T, 8.5 T, 8.6 T, 8.7 T, 8.8 T, 8.9 T, 9.0 T, 9.1 T, 9.2 T, 9.3 T, 9.4 T, 9.5 T, 9.6 T, 9.7 T, 9.8 T, 9.9 T, 10.0 T, 10.1 T, 10.2 T, 10.3

T, 10.4 T, 10.5 T, 10.6 T, 10.7 T, 10.8 T, 10.9 T, 11.0 T, 11.1 T, 11.2 T, 11.3 T, 11.4 T, 11.5 T, 11.6 T, 11.7 T, 11.8 T, 11.9 T, 12.0 T, 12.1 T, 12.2 T, 12.3 T, 12.4 T, 12.5 T, 12.6 T, 12.7 T, 12.8 T, 12.9 T, 13.0 T, 13.1 T, 13.2 T, 13.3 T, 13.4 T, 13.5 T, 13.6 T, 13.7 T, 13.8 T, 13.9 T, 14.0 T, 14.1 T, 14.2 T, 14.3 T, 14.4 T, 14.5 T, 14.6 T, 14.7 T, 14.8 T, 14.9 T, 15.0 T, 15.1 T, 15.2 T, 15.3 T, 15.4 T, 15.5 T, 15.6 T, 15.7 T, 15.8 T, 15.9 T, 16.0 T, 16.1 T, 16.2 T, 16.3 T, 16.4 T, 16.5 T, 16.6 T, 16.7 T, 16.8 T, 16.9 T, 17.0 T, 17.1 T, 17.2 T, 17.3 T, 17.4 T, 17.5 T, 17.6 T, 17.7 T, 17.8 T, 17.9 T, 18.0 T, 18.1 T, 18.2 T, 18.3 T, 18.4 T, 18.5 T, 18.6 T, 18.7 T, 18.8 T, 18.9 T, 19.0 T, 19.1 T, 19.2 T, 19.3 T, 19.4 T, 19.5 T, 19.6 T, 19.7 T, 19.8 T, 19.9 T, 20.0 T, 20.1 T, 20.2 T, 20.3 T, 20.4 T, 20.5 T, 20.6 T, 20.7 T, 20.8 T, 20.9 T, or more. Furthermore, a main coil may be used to generate magnetic fields that are within the range of 4 T to 20 T (or more, or less) that are not specifically listed above.

Figure 2:
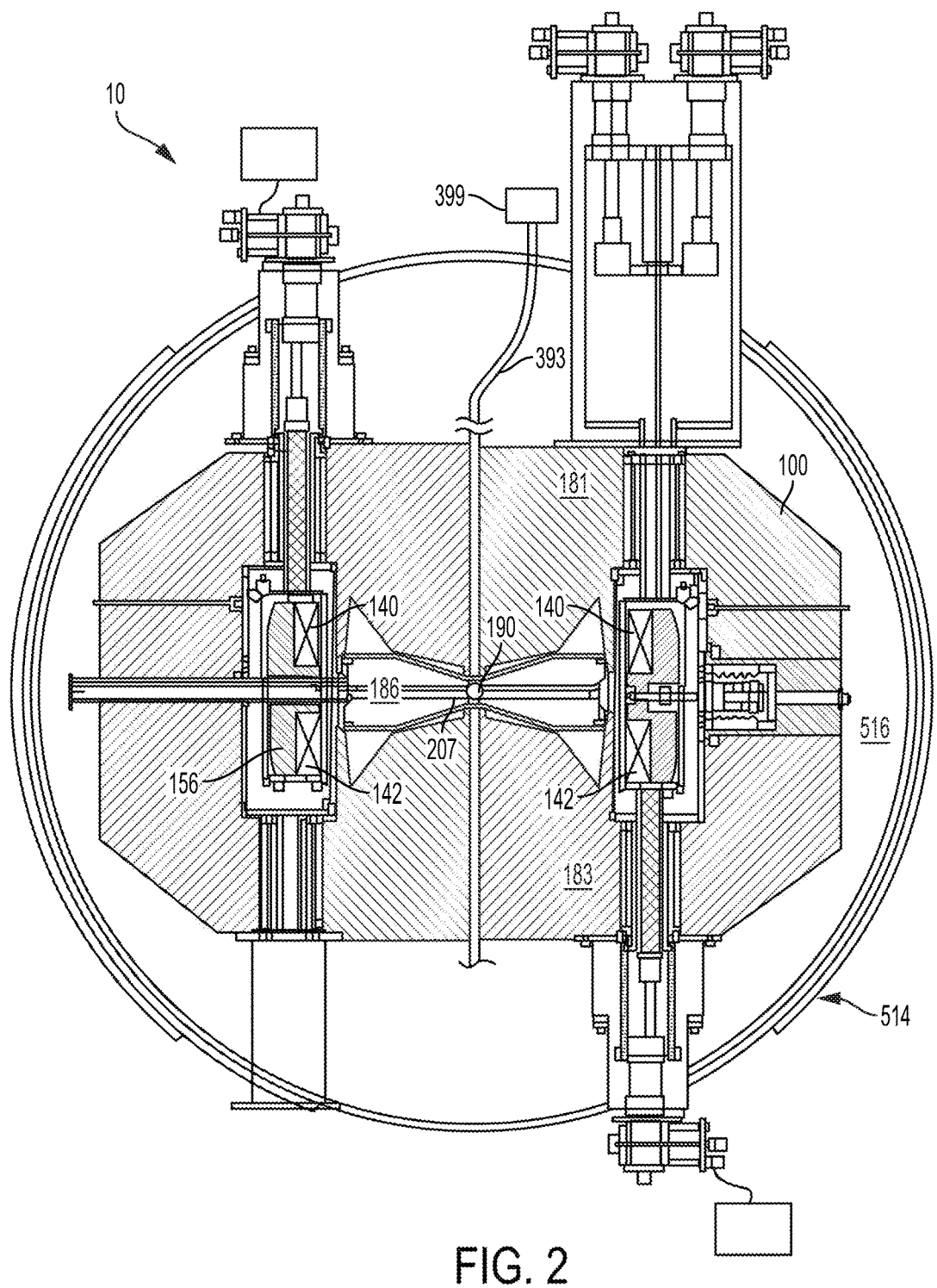

In some implementations, such as the examples shown in FIGS. 1 and 2, large ferromagnetic magnetic yokes act as a return for stray magnetic field produced by the superconducting coils. For example, in some implementations, the superconducting magnet can generate a relatively high magnetic field of, e.g., 4 T or more, resulting in considerable stray magnetic fields. In some systems, such as that shown in FIGS. 1 and 2, the relatively large ferromagnetic return yoke 100 are used as a return for the magnetic field generated by superconducting coils. A magnetic shield surrounds the yoke. The return yoke and the shield together dissipate stray magnetic field, thereby reducing the possibility that stray magnetic fields will adversely affect the operation of the accelerator.

In some implementations, the return yoke and shield may be replaced by, or augmented by, an active return system. An example active return system includes one or more active return coils that conduct current in a direction opposite to current through the main superconducting coils. In some example implementations, there is an active return coil for each superconducting coil, e.g., two active return coils—one for each superconducting coil (referred to as a "main" coil). Each active return coil may also be a superconducting coil that surrounds the outside of a corresponding main superconducting coil.

Current passes through the active return coils in a direction that is opposite to the direction of current passing through the main coils. The current passing through the active return coils thus generates a magnetic field that is opposite in polarity to the magnetic field generated by the main coils. As a result, the magnetic field generated by an active return coil is able to dissipate at least some of the relatively strong stray magnetic field resulting from the corresponding main coil. In some implementations, each active return may be used to generate a magnetic field of between 2.5 T and 12 T or more. An example of an active return system that may be used is described in U.S. patent application Ser. No. 13/907,601 (U.S. Pat. No. 8,791,656), filed on May 31, 2013, the contents of which are incorporated herein by reference.

Figure 3:
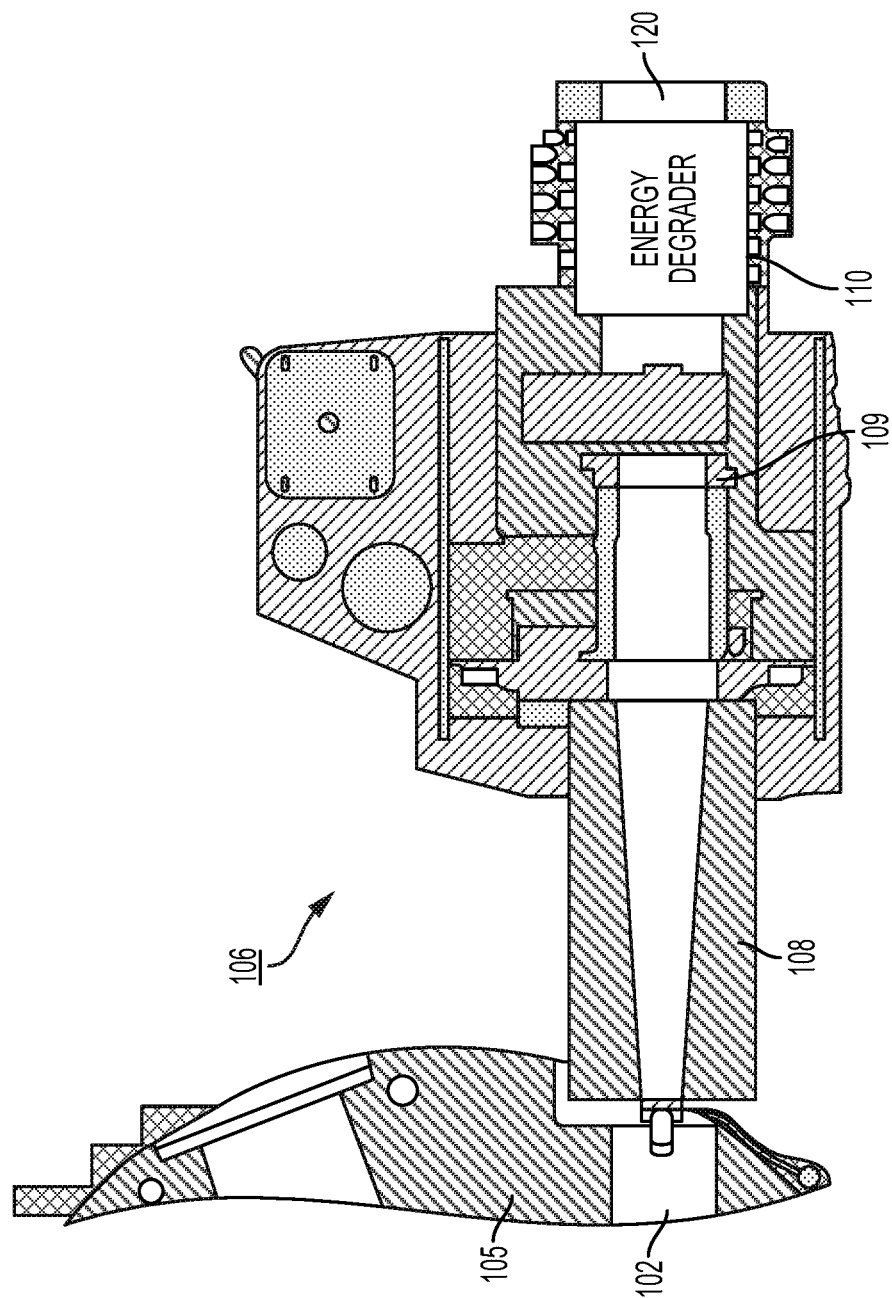
FIG. 3 is a side view of an example scanning system.
Figure 4:
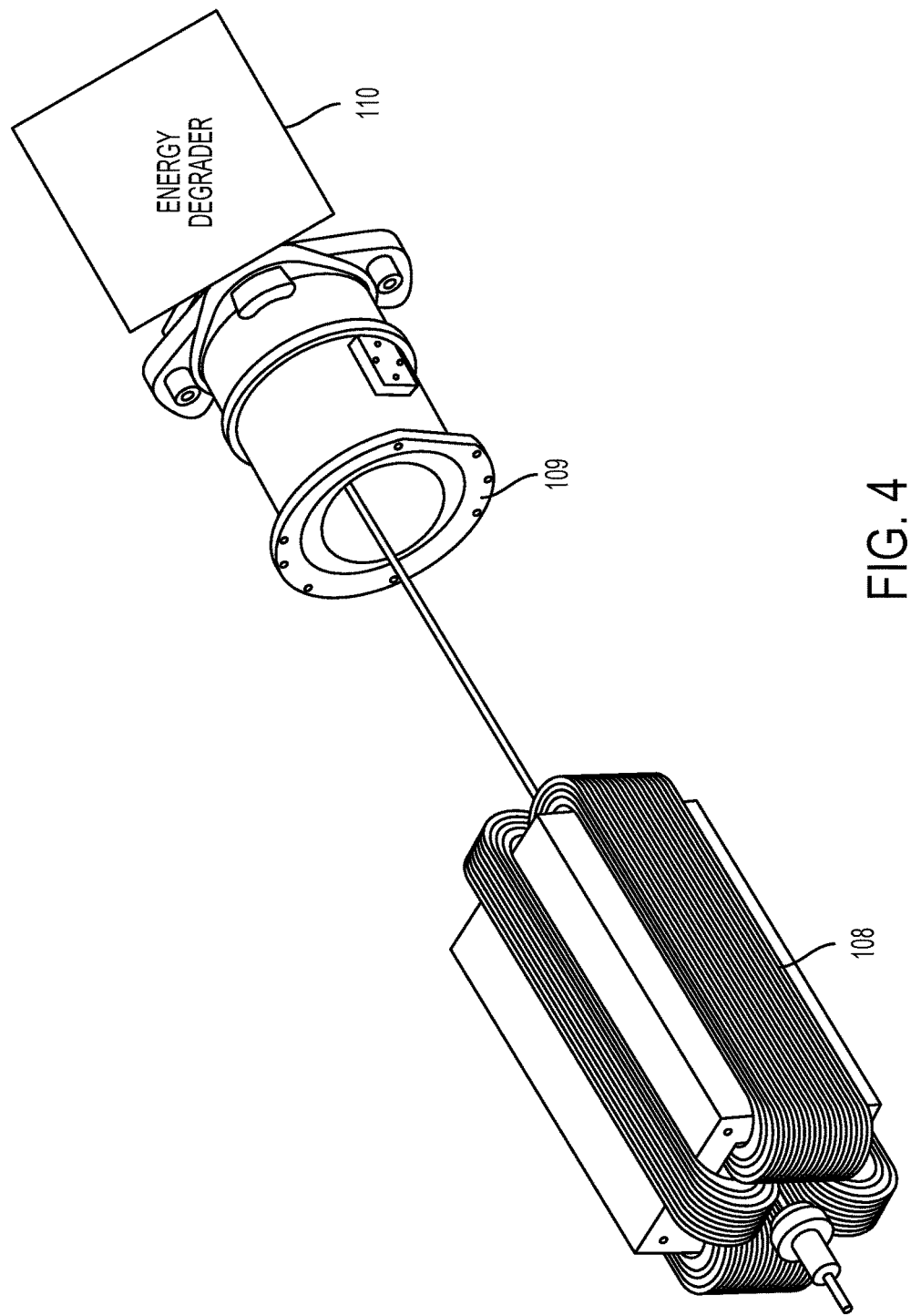
FIG. 4 is a perspective view of components of an example scanning system, excluding scattering material for spot size variation.

Referring to FIG. 3, at the output of extraction channel 102 of particle accelerator 105 (which may have the configuration shown in FIGS. 1 and 2), is an example scanning system 106 that may be used to scan the particle beam across at least part of an irradiation target. FIG. 4 shows examples of components of the scanning system. These include, but are not limited to, a scanning magnet 108, an ion chamber 109, and an energy degrader 110. Other components that may be incorporated into the scanning system are not shown in FIG. 4, including, e.g., one or more scatterers for changing beam spot size.

In an example operation, scanning magnet 108 is controllable in two dimensions (e.g., Cartesian XY dimensions) to direct the particle beam across a part (e.g., a cross-section) of an irradiation target. Ion chamber 109 detects the dosage of the beam and feeds-back that information to a control system to adjust beam movement. Energy degrader 110 is controllable to move material into, and out of, the path of the particle beam to change the energy of the particle beam and therefore the depth to which the particle beam will penetrate the irradiation target.

Figure 5:
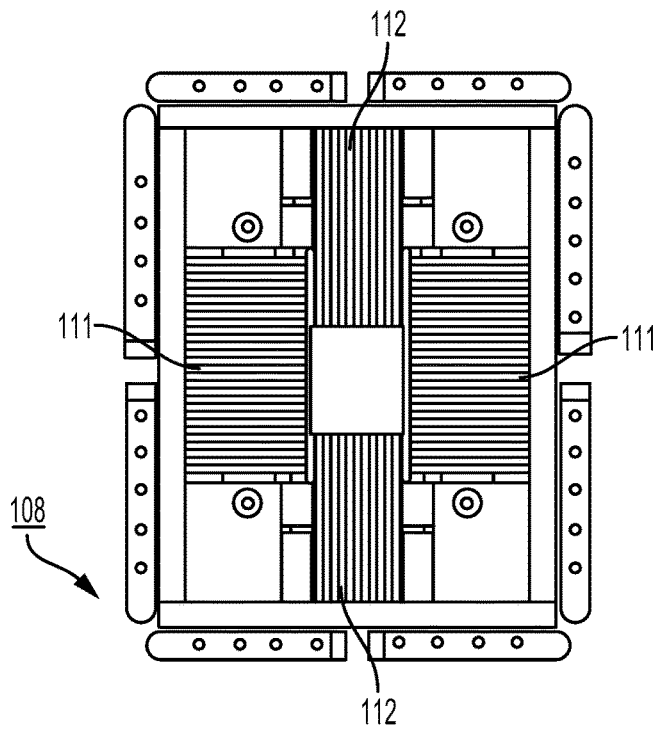
FIG. 5 is a front view of an example magnet for use in a scanning system of the type shown in FIGS. 3 and 4.
Figure 6:
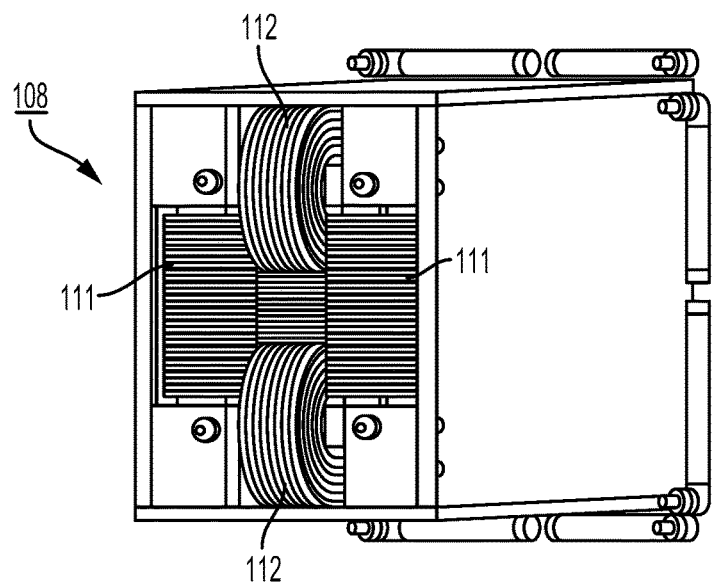
FIG. 6 is a perspective view of an example magnet for use in a scanning system of the type shown in FIGS. 3 and 4.

FIGS. 5 and 6 shows views of an example scanning magnet 108. Scanning magnet 108 includes two coils 111, which control particle beam movement in the X direction, and two coils 112, which control particle beam movement in the Y direction. Control is achieved, in some implementations, by varying current through one or both sets of coils to thereby vary the magnetic field(s) produced thereby. By varying the magnetic field(s) appropriately, the particle beam can be moved in the X and/or Y direction across the irradiation target. In some implementations, the scanning magnet is not movable physically relative to the particle accelerator. In other implementations, the scanning magnet may be movable relative to the accelerator (e.g., in addition to the movement provided by the gantry). In some implementations, the scanning magnets may be controllable to move the particle beam continuously. In other implementations, the scanning magnets are controllable at intervals or specific times. In some implementations, there may be different scanning magnets to control movement of the beam in the X and/or Y directions. In some implementations, there may be different scanning magnets to control partial movement of the beam in either the X and/or Y direction.

In some implementations, ion chamber 109 detects dosage applied by the particle beam by detecting the numbers of ion pairs created within a gas caused by incident radiation. The numbers of ion pairs correspond to the dosage provided by the particle beam. That information is fed-back to a computer system that controls operation of the particle therapy system. The computer system (not shown), which may include memory and one or more processing devices, determines if the dosage detected by the ion chamber is the intended dose. If the dosage is not as intended, the computer system may control the accelerator to interrupt production and/or output of the particle beam, and/or control the scanning magnet to prevent output of the particle beam to the irradiation target. For example, to prevent or modify output of the particle beam, the computer system may turn the ion source off/on, change the frequency of the RF sweep, activate one or more mechanisms (such as a fast kicker magnet (not shown)) to divert the beam to an absorber material and thereby prevent the beam output, and so forth.

Figure 7:
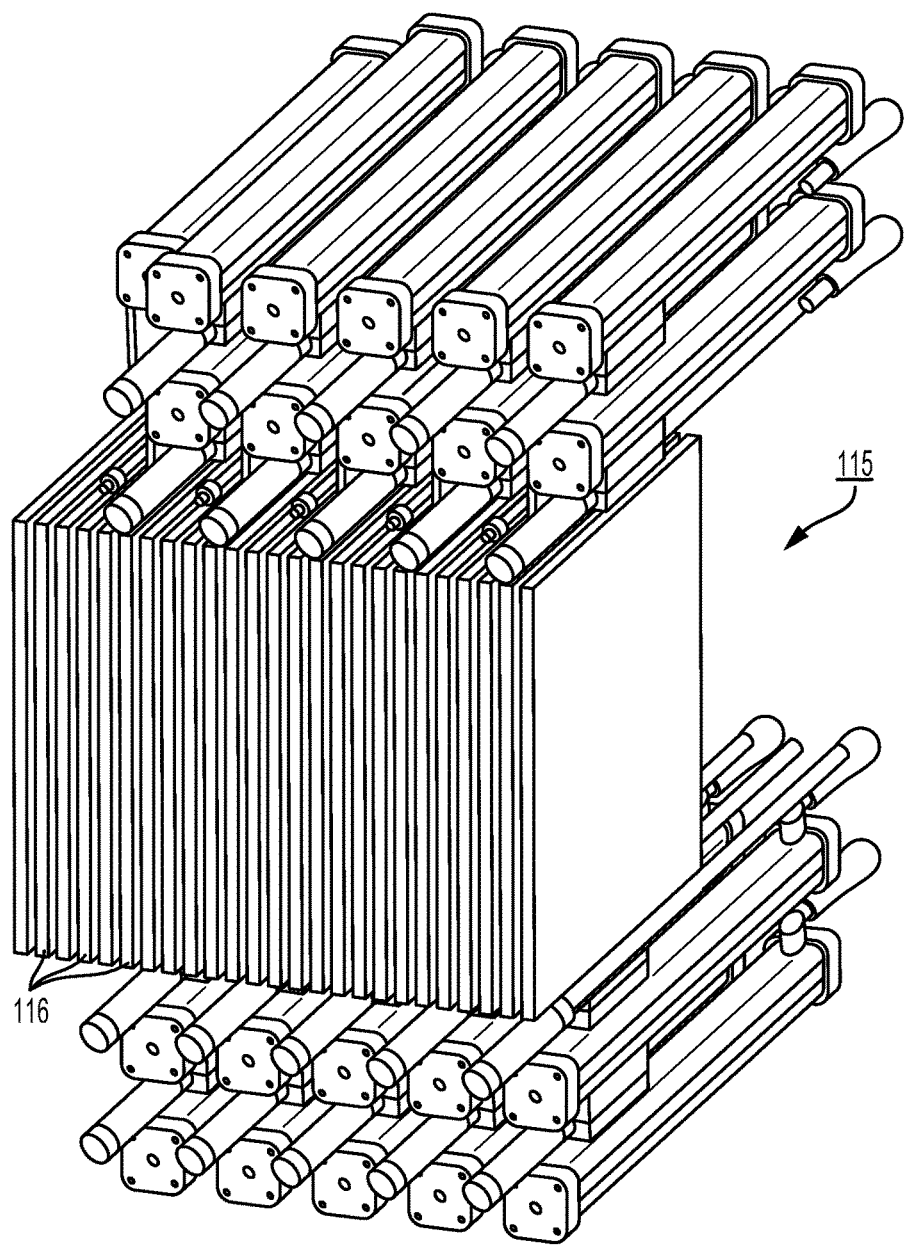
FIG. 7 is a perspective view of an example energy degrader (range modulator) for use in a scanning system of the type shown in FIGS. 3 and 4.

FIG. 7 shows a range modulator 115, which is an example implementation of energy degrader 110. In some implementations, such as that shown in FIG. 7, range modulator includes a series of plates 116. The plates may be made of one or more of the following example materials: polycarbonate, carbon, beryllium or other material of low atomic number. Other materials, however, may be used in place of, or in addition to, these example materials.

One or more of the plates is movable into, or out of, the beam path to thereby affect the energy of the particle beam and, thus, the depth of penetration of the particle beam within the irradiation target. For example, the more plates that are moved into the path of the particle beam, the more energy that will be absorbed by the plates, and the less energy the particle beam will have. Conversely, the fewer plates that are moved into the path of the particle beam, the less energy that will be absorbed by the plates, and the more energy the particle beam will have. Higher energy particle beams penetrate deeper into the irradiation target than do lower energy particle beams. In this context, "higher" and "lower" are meant as relative terms, and do not have any specific numeric connotations.

Figure 8:
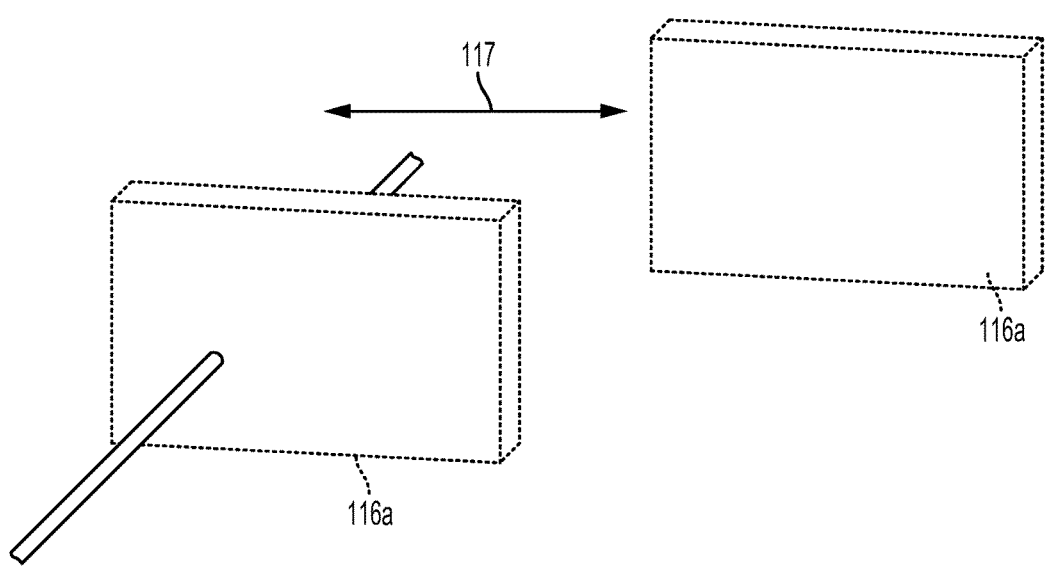
FIG. 8 is a perspective view of a process for moving a plate of an energy degrader in the path of a particle beam

Plates are moved physically into, and out of, the path of the particle beam. For example, as shown in FIG. 8, a plate 116*a* moves along the direction of arrow 117 between positions in the path of the particle beam and outside the path of the particle beam. The plates are computer-controlled. Generally, the number of plates that are moved into the path of the particle beam corresponds to the depth at which scanning of an irradiation target is to take place. For example, the irradiation target can be divided into cross-sections, each of which corresponds to an irradiation depth. One or more plates of the range modulator can be moved into, or out of, the beam path to the irradiation target in order to achieve the appropriate energy to irradiate each of these cross-sections of the irradiation target. Traditionally, the range modulator was stationary relative to the particle beam during scanning of a part of (e.g., cross-section of) an irradiation target, except for its plates moving in and out of the path of the particle beam.

In some implementations, the range modulator of FIGS. 7 and 8 may be replaced with a range modulator that, at least some of the time, tracks movement of the particle beam. This type of energy degrader is described in more detail below. In some implementations, the range modulator may be an energy-switching range modulator, examples of which are described with respect to FIGS. 35 to 49.

In some implementations, the particle accelerator may be a variable-energy particle accelerator, such as the example particle accelerator described in U.S. patent application Ser. No. 13/916,401 (U.S. Patent Publication No. 2014/0371511), filed on Jun. 12, 2013, the contents of which are incorporated herein by reference. In example systems where a variable-energy particle accelerator is used, there may be less need for an energy degrader of the type described herein, as the energy level of the particle beam may be controlled by the particle accelerator. For example, in some systems that employ a variable-energy particle accelerator, an energy degrader may not be needed. In some systems that employ a variable-energy particle accelerator, an energy degrader may still be used to change beam energy levels.

In some implementations, a treatment plan is established prior to treating the irradiation target. The treatment plan may specify how scanning is to be performed for a particular irradiation target. In some implementations, the treatment plan specifies the following information: a type of scanning (e.g., spot scanning or raster scanning); scan locations (e.g., locations of spots to be scanned); magnet current per scan location; dosage-per-spot, spot size; locations (e.g., depths) of irradiation target cross-sections; particle beam energy per cross-section; plates or other types of pieces to move into the beam path for each particle beam energy; and so forth. Generally, spot scanning involves applying irradiation at discrete spots on an irradiation target and raster scanning involves moving a radiation spot across the radiation target. The concept of spot size therefore applies for both raster and spot scanning.

In some implementations, the overall treatment plan of an irradiation target includes different treatment plans for different cross-sections of the irradiation target. The treatment plans for different cross-sections may contain the same information or different information, such as that provided above.

In some implementations, the scanning system may include a collimator 120 (FIG. 3) to collimate the particle bean, which may include an aperture that is placeable relative to the irradiation target to limit the extent of the particle beam and thereby alter the shape of the spot applied to the irradiation target. For example, the collimator may be placed in the beam path down-beam of the energy degrader and before the particle beam hits the irradiation target. The collimator may contain an area (e.g., a hole or a transmissive material) through which the particle beam passes and another material (e.g., brass) around the hole that inhibits or prevents passage of the particle beam.

Figure 9:
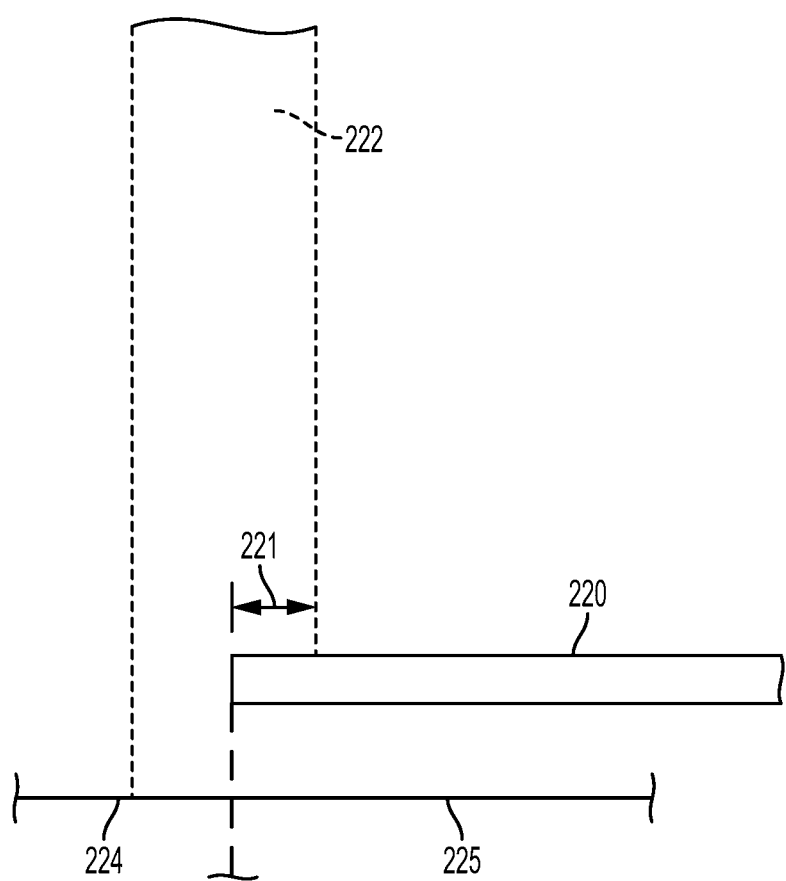
FIG. 9 is a side view of an example particle beam and collimator.

In some implementations, the collimator may include a structure defining an edge. The structure may include a material, such as brass, that inhibits transmission of the particle beam. The structure may be controllable to move in two dimensions relative to the irradiation target so that at least part of the structure is between at least part of the particle beam and the irradiation target. For example, the structure may be movable in the X and Y directions of a plane that intersects the particle beam and that is parallel, or substantially parallel to, a cross-section of the irradiation target that is being treated. Use of a collimator in this manner may be beneficial in that it can be used to customize the cross-sectional shape of the particle beam that reaches the patient, thereby limiting the amount of particle beam that extends beyond the radiation target. For example, as shown in FIG. 9, a structure 220 in a collimator prevents portion 221 of particle beam 222 from reaching a target 224, thereby limiting the beam to the irradiation target and reducing exposure of healthy tissue 225 to radiation. By placing a structure with an edge between part of the particle beam and the patient, the example collimator also provides a defined, or sharp, edge to the particle beam portion that reaches the patient, thereby promoting more precise dose applications.

Positioning and movement of the collimator may be controlled by a control computer system that controls other features of the particle therapy system described herein. For example, the collimator may be controlled in accordance with the treatment plan to track (e.g., follow) motion of the particle beam across at least part of the irradiation target. In some implementations, the collimator track is controlled to track all motion of the particle beam relative to the irradiation target. For example, in some implementations, the collimator may be controlled to track motion of the particle beam throughout the entirety of the irradiation target, e.g., both at edges of the irradiation target and at interiors of the irradiation target. In some implementations, the collimator is controlled to track only some motion of the particle beam relative to the irradiation target. For example, the collimator may be controlled to track movement of the particle beam only along the edges of the irradiation target relative to when the particle beam reaches those edges.

Figure 10:
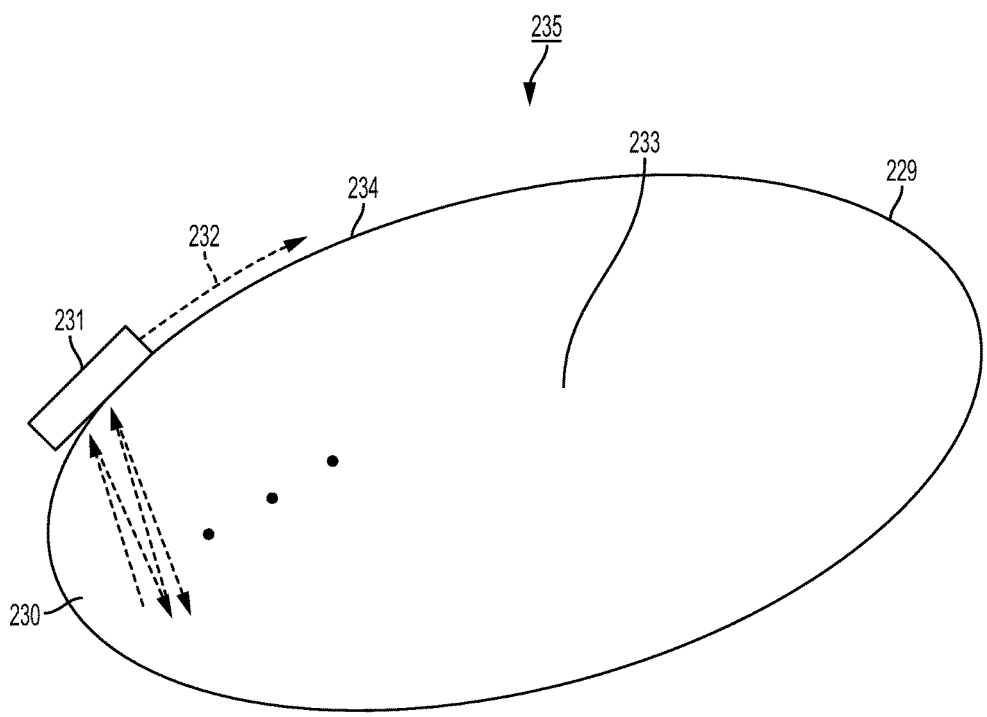
FIG. 10 is a top view show an example cross-section of an irradiation target, an example collimator that is movable along the edge of the cross-section, and an example beam scanning path along an interior of the irradiation target.

Referring to FIG. 10, for instance, a particle beam may follow a path in an irradiation target 229 shown by arrowed lines 230. Collimator 231 may not track motion of the particle beam on the interior 233 of irradiation target 229. But, collimator 231 may track motion of the particle beam along only the edges of the irradiation target (e.g., roughly along arrow 232). For example, each time the particle beam reaches an edge 234 of the irradiation target, the collimator may move, or may have previously moved, to intercept the particle beam at the edge, and thereby limit exposure of surrounding tissue 235 to the beam. When, and by how much, the collimator moves may depend on the size of the particle beam cross-section (spot) and the speed at which the particle beam scans. In this example, there is no need to limit exposure to the particle beam at the interior of the irradiation target; hence, the collimator need not track the beam at the interior.

The movement of a collimator may be controlled in various ways. For example, the current through magnet 108 may correspond to the deflection of the particle beam by the magnet and, thus, the location of the particle beam spot on the irradiation target. So, for example, knowing the current through the magnet and the location of the irradiation target relative to the magnet, a computer system controlling operation of the scanning system can determine the projected location of the irradiation spot. And, knowing the location of the radiation spot, the computer system can control the scanning system, in particular the collimator, to track movement of the irradiation spot along all or part of its motion, as described herein. In some implementations, the computer system can control the scanning system, in particular the collimator, so that the collimator arrives at a location before the particle beam spot arrives at that location, as described in more detail below.

Use of a collimator, such as is described above, can have advantages. For example, in some cases, goals of particle beam scanning may include achieving accuracy at the edges of an irradiation target and uniformity of dosage or coverage in the interior of the irradiation target. The use of a collimator can help to further these goals by enabling use of a relatively large particle beam spot for scanning. In this context, a spot size may be considered "large" if it has an area that is within a specified percentage of the area of the irradiation target. This percentage might typically be 2.5%, but values between, e.g., 0.25% and 25%, could also be used. Scanning using a relative large spot size increases the fractional areal coverage of the irradiation target for each beam pulse. Typically, the larger the size of this spot, the less adversely affected the target uniformity will be due to target (patient) motion. At the edges, however, the collimator reduces the chances that radiation from the large spot will impact tissue (e.g., healthy tissue) outside the radiation target by reducing the lateral penumbra. Traditionally, smaller spot sizes were preferred, since they enabled more precise dosage at the edges as compared to a larger spot size. But, compared to a collimated edge, those smaller spot sizes could result in slower treatment times for a given treatment volume, and reduced edge conformality due to reduced edge resolution and increased penumbra.

The collimator may have any number of different shapes or configurations and may, or may not, include one or more moving parts. In an example implementation, the collimator is comprised of brass and/or other radiation-blocking material, and has a thickness on the order of several centimeters. However, different collimators may have different compositions and thicknesses.

Figure 11:
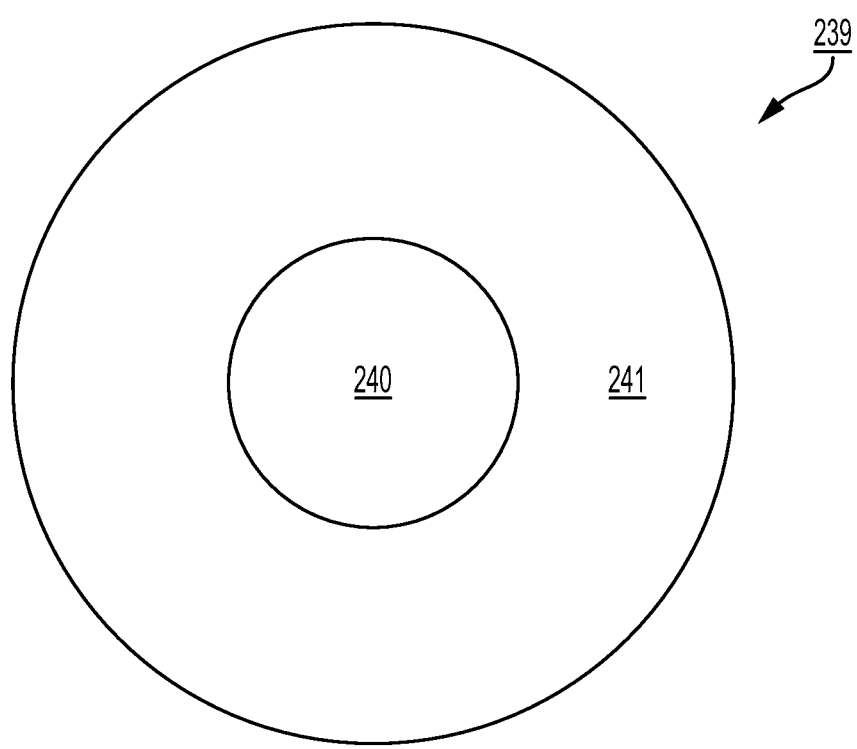
FIG. 11 is a top view of an example collimator.

In example implementations, the collimator is a structure that has one or more defined edges. For example, the collimator may be a structure containing an aperture, or hole. FIG. 11 shows an example of this type of collimator 239. Collimator 239 may have any appropriate shape, with an aperture therein. The edges of the aperture may be used to limit application of the particle beam, as shown in FIG. 9 for example, thereby allowing application of beam 222 to the irradiation target 224 but not to tissue covered by collimator 220 that is otherwise in the beam path. As explained above, the aperture may track (e.g., follow) the particle beam throughout all or part of the scanning operation. For example, the aperture may track movement of the particle beam only at edges of the irradiation target or throughout the entire motion of the beam. That is, the collimator itself may move along the edge of the irradiation target to track movement of the particle beam (e.g., so that the location of the collimator coincides with the particle beam when the particle beam reaches the irradiation target edge).

Figure 12:
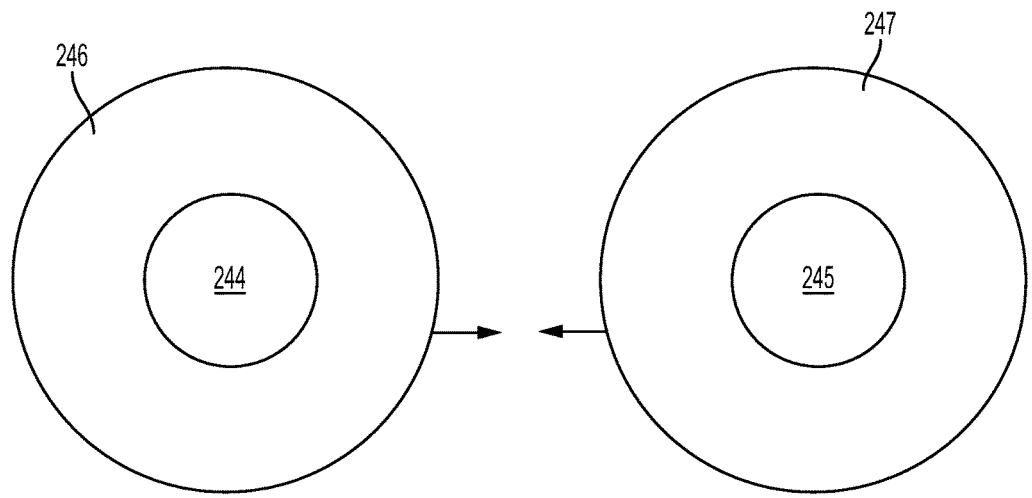
FIG. 12 is a top view of components of an example collimator.
Figure 13:
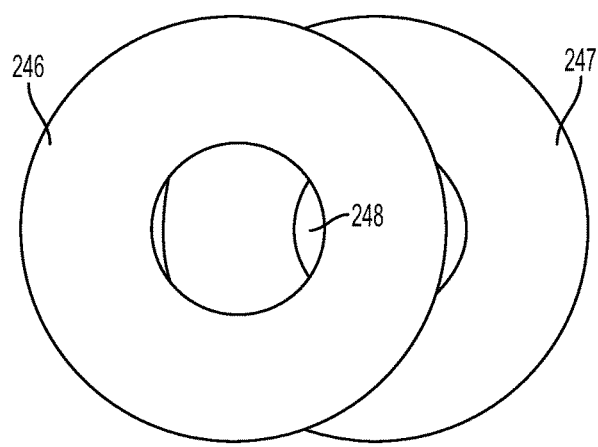
FIG. 13 is a top view showing the components of FIG. 12 combined to form an example collimator.

In some implementations, the collimator may include two or more apertures that are controlled to overlap and thereby achieve a specific size. For example, as shown in FIG. 12, apertures 244 and 245 are part of respective structures 246 and 247. The structures move relative to each other, as shown in FIG. 13, thereby causing the apertures 244, 245 to overlap and change the size and, in some cases, the shape of resulting hole 248 through which the particle beam is allowed to pass. Shapes other than those shown may be used.

In some implementations, the collimator may track the movement of the particle beam during the particle beam's motion in the interior of the irradiation target. For example, in some implementations, the aperture may have a diameter that is less than the diameter of the particle beam spot. In some systems, it may be desirable to use a spot having a specific diameter at all irradiation positions (including those on the interior of the irradiation target). In these systems, therefore, the aperture may track all movement of the particle beam spot so as to achieve the appropriate particle beam spot diameter for treatment. In some implementations, the aperture of the collimator may vary in size and/or shape. For example, the collimator may have one or more moving parts to vary the size and shape of the aperture (e.g., to reduce its diameter, surface area, or the like).

In example implementations, the collimator may be a structure having one or more straight edges. For example, the collimator may include square, rectangular, or substantially linear structures, each having at least one edge that can be placed in the path of the particle beam.

Figure 14:
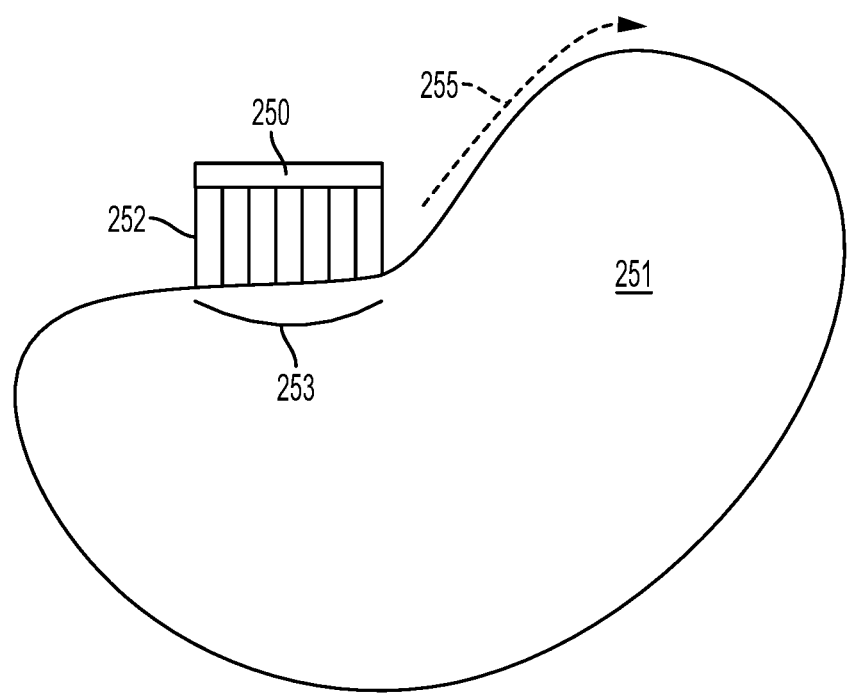
FIG. 14 is a top view showing an example cross-section of an irradiation target, and an example multi-leaf collimator that is movable along the edge of the cross-section during particle beam scanning.

In an example implementation that employs straight edges, the collimator may have a multi-leaf structure, as in FIG. 14. In FIG. 14, collimator 250 tracks movement along the edge of irradiation target 251. Fingers 252 move up or down, or towards or away from the irradiation target, in order to achieve an edge shape 253 that substantially matches the edge shape of the irradiation target and that blocks the particle beam from reaching healthy tissue (or tissue that should not be irradiated). For example, each finger can be moved up or down, or extended and retracted, or a combination of such movements to substantially match the edge shape. Collimator 250 itself may move along the edge of the irradiation target 251 (e.g., roughly in the direction of arrow 255) to track movement of the particle beam (e.g., so that the location of the collimator coincides with the particle beam when the particle beam reaches the irradiation target edge). In some implementations, collimator 250 may, or may not, move into the interior of the irradiation target during scanning operations.

Traditional multi-leaf collimators are stationary relative to the irradiation target and include two sets of fingers that face each other and that move relative to each other to attain the appropriate collimation. There may be tens, hundreds, or even thousands of fingers used in such collimators, and their size may be as large as the irradiation field itself. In some implementations, the irradiation field may be defined by a plane, which is at an angle to the beam, and which defines the maximum extent that a particle beam can move in the X and Y directions relative to the irradiation target. However, in the example implementations described herein, the collimator moves relative to (e.g., tracks or moves along the edge of) the irradiation target, and need only provide a defined edge at the point of the irradiation target where and when the spot hits that point. Accordingly, the multi-leaf collimator may be made considerably smaller than its conventional counterparts. For example, the multi-leaf collimators described herein may include ten or less (e.g., two, three, four, five, six, seven, eight or nine) fingers (or more, if desired).

Figure 15:
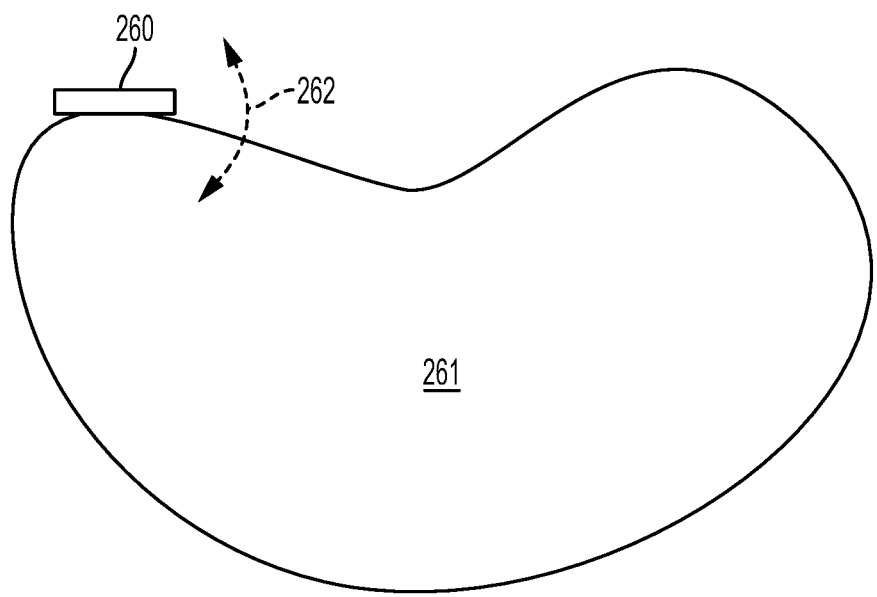
FIG. 15 is a top view showing an example cross-section of an irradiation target, and an example straight-edge collimator that is movable and rotatable along the edge of the cross-section during particle beam scanning.

In an example implementation that employs straight edges, as shown in FIG. 15, collimator 260 may be rectangular in shape, and move along the edge of irradiation target 261. Collimator 260 may move along the edge of the irradiation target to track movement of the particle beam (e.g., so that the location of the collimator coincides with the particle beam when the particle beam reaches the irradiation target edge). During motion along the edge of the irradiation target, collimator 260 may also rotate in two or three dimensions, e.g., in the XY dimensions of arrow 262 and also in the Z dimension. This rotation allows at least a portion of an edge of collimator 260 to match the edge of the irradiation target relatively closely. Thus, collimator 260 may be appropriately positioned so that, when the particle beam reaches the edge of the irradiation target, the collimator blocks the tissue extending beyond the edge. As a result, the collimator provides a defined radiation edge relative to the irradiation target and protects adjacent tissue from the particle beam. Movement of the collimator to the appropriate point on the edge of the irradiation target may coincide with movement of the particle beam or precede movement of the particle beam.

Figure 16:
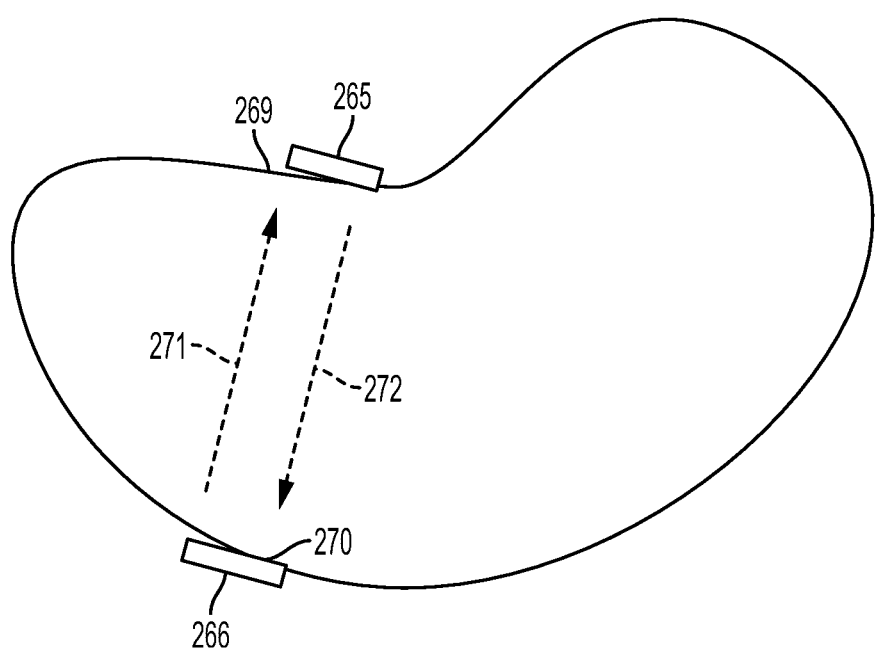
FIG. 16 is a top view showing an example cross-section of an irradiation target, an example multi-part collimator that is movable along the edges of the cross-section during particle beam scanning, and example beam scanning paths along an interior of the irradiation target.

In some implementations, the collimator may include a single structure with one or more straight edges, as shown in FIG. 15. In other implementations, the collimator may include two or more such structures at different (e.g., opposing) edges of the irradiation target, as shown in FIG. 16. There, the collimator includes two structures 265, 266. Each of structures 265 and 266 tracks movement of the particle beam. That is, structure 265 moves so that the location of structure 265 coincides with the particle beam when the particle beam reaches edge 269 of the irradiation target, and structure 266 moves so that the location of structure 266 coincides with the particle beam when the particle beam reaches edge 270 of the irradiation target. Movement of each structure to the appropriate point on the edge of the irradiation target may coincide with movement of the particle beam or precede movement of the particle beam. For example, structure 266 can be moved as the spot is scanned in the direction of arrow 271, so that structure 266 is in the appropriate location when the spot returns to edge 270; and structure 265 can be moved as the spot is scanned in the direction of arrow 272, so that structure 265 is in the appropriate location when the spot returns to edge 269. Structures 265 and 266 may move at the same times, at different times, or there may be overlap in the times of their movement. An arrangement of this type enables the particle beam to be moved from edge to edge of the irradiation target, with the collimator enabling a defined irradiation field at both edges. And, since the collimator is comprised of multiple structures, scanning need not be significantly slowed waiting for movement of the collimator. In some implementations, the collimator may include more than two (e.g., three, four, etc.) structures of the type and operation shown in FIG. 16. In some implementations, the two or more structures that make up the collimator may be structures that include holes, such as that shown in FIG. 11. The operation of the two-structure collimator is otherwise as described above.

Figure 17:
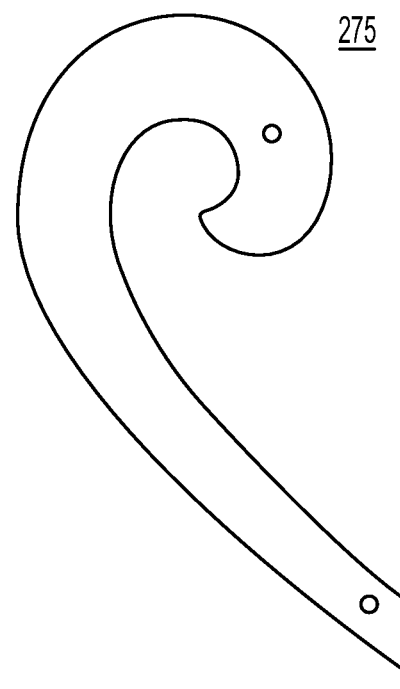
FIG. 17 is a top view of an example curved collimator.

In some implementations, the collimator need not have a straight edge, but rather its edge(s) may be curved, as shown in FIG. 17. A collimator may include only one such structure or two or more such structures. In some implementations, the two or more structures that make up the collimator may be structures that include curved edges. For example, two structures of the type shown in FIG. 17 may replace the two structures of FIG. 16. The operation of the two-structure collimator is otherwise as described above.

In this regard, in example implementations, the collimator may be a structure having a curved shape having a radius of curvature that varies continuously along its edge, thereby enabling at least part of the edge to closely match the edge of an irradiation target, either directly or by rotating the edge at an appropriate angle. In this example, collimator 275 is a French curve that can be moved to track the beam, either partly or fully, and that can be rotated in two or three dimensions relative to the irradiation target to control application of the particle beam. Any appropriately curved structure may be include in the collimator. As was the case above, collimator 275 may only move along the edge of the irradiation target to track movement of the particle beam (e.g., so that the location of the collimator coincides with the particle beam when the particle beam reaches the irradiation target edge). As was the case above, the collimator may, or may not, track movement of the particle beam at the interior of the irradiation target.

A collimator may include only one structure of the type shown in FIG. 17 or the collimator may include two or more such structures. For example, two structures of the type shown in FIG. 17 may replace the two structures of FIG. 16. The operation of the two-structure collimator is otherwise as described above.

In some implementations, the treatment planning system may be designed so that the scanning speed (e.g., the rate at which the particle beam spot traverses the irradiation target) is different in the interior of the irradiation target than at the edges of the irradiation target. For example, the scanning speed may be faster at the interior of the irradiation target than at the edges of the irradiation target. This arrangement allows for higher precision scanning at the edges of the irradiation target than at the interior of the irradiation target. This type of variable-speed scanning may be implemented using any appropriate type of collimator, including those described herein, or this type of variable-speed scanning may be implemented without using any collimator. In either case, the slower speed at the irradiation target edge may enable more precise scanning there, which may reduce the chances that the particle beam will impact outside the irradiation target.

Figure 18:
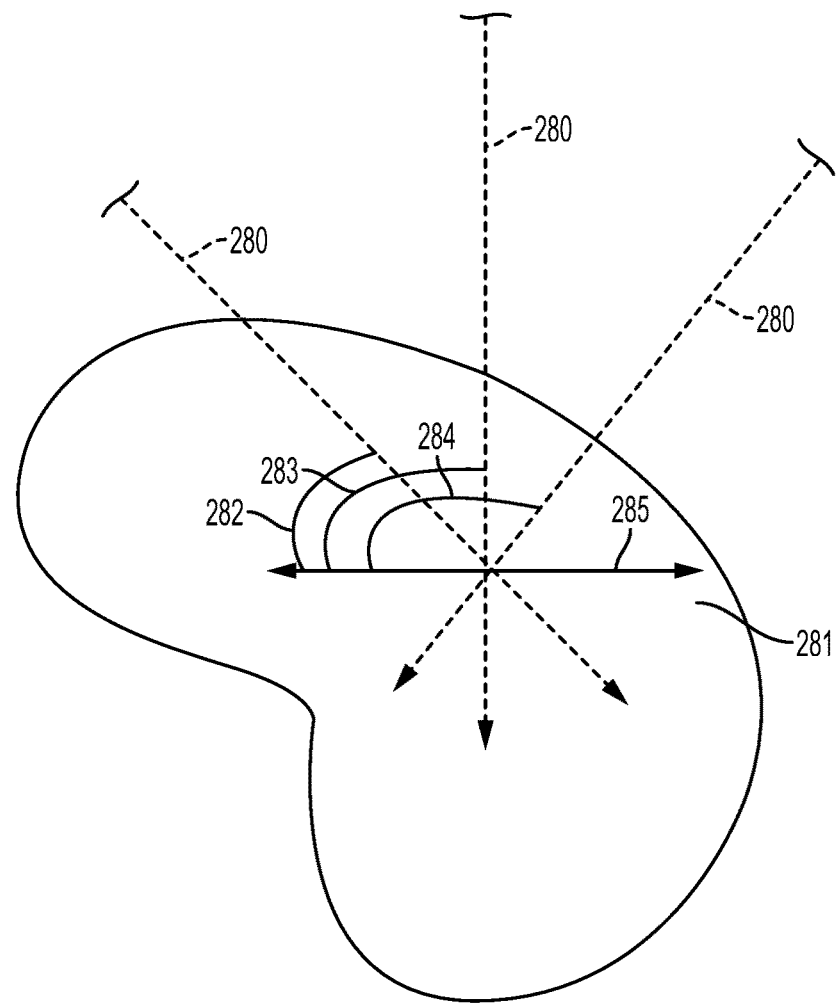
FIG. 18 is a view showing an example cross-section of an irradiation target, and an example of how intensity-modulated proton therapy is performed on the irradiation target.

In some implementations, the collimator described herein may be used in an intensity-modulated proton therapy process. In such as process, the proton beam is projected at the radiation target from different directions so that a percentage of the overall dose is delivered from each direction. As a result, the amount of dose delivered to volumes outside of the irradiation target can be reduced. For example, FIG. 18 shows a particle beam 280 applied to the irradiation target 281 from three different angles. In this example, ⅓ of the total dose may be applied from one angle; ⅓ of the total dose may be applied from another angle; and ⅓ of the total dose may be applied from yet another angle. That is, the particle beam may be scanned at angle 282 relative to horizontal 285 to apply ⅓ of the dose; the particle beam may be scanned at angle 283 to apply ⅓ of the dose; and the particle beam may be scanned at angle 284 to apply ⅓ of the dose. As a result, the amount of radiation applied to surrounding tissue 287 is spread out at the appropriate angles, thereby reducing the chances that surrounding tissue will be exposed to harmful amounts of radiation. Any appropriate number of angles and appropriate dosage per angle may be employed.

Irradiation targets, such as tumors, typically are not symmetric. Accordingly, different beam collimation is typically required for the different angles of application of the particle beam. The example collimators described herein can be positioned at the appropriate locations along the irradiation target's edge (as described above) to provide appropriate collimation given the angle of irradiation. In some implementations, the example collimators can track motion of the particle beam, either only at the irradiation target's edge or throughout some portion (e.g., all) of the motion of the particle beam at all angles of application.

In some implementations, the example collimators described herein prevent transmission of the particle beam to surrounding tissue by blocking the particle beam. In some implementations, the example collimators may enable partial transmission of the particle beam, thereby resulting in application of lower-levels of radiation to the surrounding tissue than to the irradiation target. Any of the example collimators described herein may be produced in this manner.

The example collimators described herein may be mounted to one or more computer-controlled robotic arms or other structures to control their movement relative to the irradiation target. A collimator may be mounted to the scanning system itself as well. Typically, the collimator is mounted closest to the patent relative to other elements of the particle beam scanning system (e.g., down-beam of other elements of the scanning system). In implementations where the collimator includes more than one piece (e.g., FIG. 16), there may be more than one robotic arm or other structure to independently control the different pieces of the collimator in accordance with the treatment plan. In some implementations, a single robotic arm may be configured to control the different pieces of the collimator independently or to control a combination of pre-assembled pieces.

In some implementations, the energy degrader may also configured to track motion of the particle beam. In this regard, in some implementations, such as the example implementation described with respect to FIGS. 7 and 8, the energy degrader may include multiple plates that are movable into the path of the particle beam to control the amount of energy in the beam and thereby control the depth to which the particle beam penetrates the irradiation target. In this way, the energy degrader is used to perform depth (the direction of the particle beam or Z-direction) scanning in the irradiation target. Typically, each plate absorbs an amount of energy in the particle beam. Accordingly, the more plates that are placed in front of the particle beam, the less energy the beam has, and the less deep the beam will penetrate into the irradiation target. Conversely, the fewer plates that are placed in front of the particle beam, the more energy the beam has (since less energy is absorbed by the plate(s)), and the more deep the beam will penetrate into the irradiation target. In some implementations, each plate has about the same thickness, and therefore absorbs about the same amount of beam energy. In other implementations, different plates may have different thicknesses, with the thickness of a plate corresponding to the amount of energy that the plate absorbs.

Figure 19:
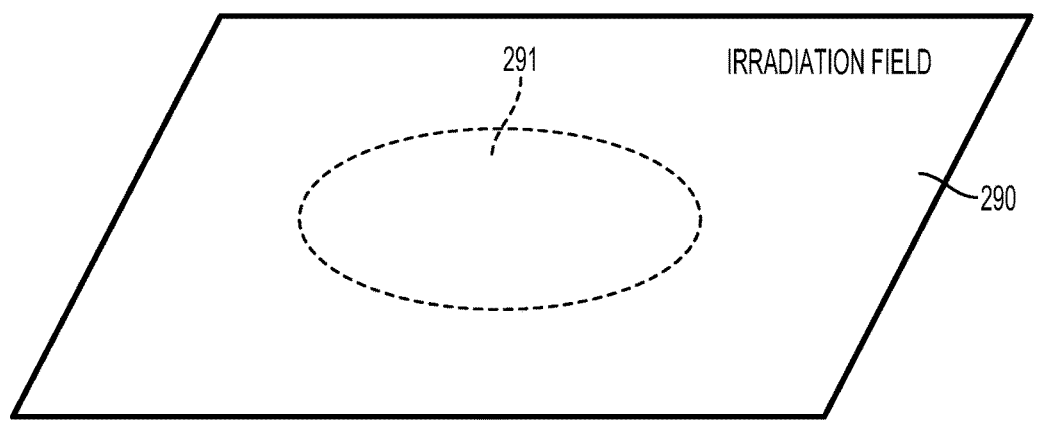
FIG. 19 is a perspective view of an example irradiation field of a particle beam scanning system.

In some implementations, the plates each have a surface area that is about the size of the irradiation field. In this context, the irradiation field may be defined by a plane that defines the maximum extent that a particle beam can move in the X and Y directions relative to the irradiation target. For example, FIG. 19 shows an irradiation field 290 (also called a beam field or radiation field) in front of an irradiation target 291. Due to physical system limitations, a particle beam is movable across, but not beyond, the plane defining the irradiation field. Accordingly, to ensure that the energy degrader can be applied to any location within the irradiation field, in some implementations the plates in the energy degrader each have a surface are that is at least as big as, and in some cases that exceeds, the size of the irradiation field. This configuration, however, can result in plates that are large (e.g., possibly a square meter or square meters), and thus that can be heavy and relative slow to move. Slow movement of the plates can result in slower treatment.

In some implementations, the energy degraders may be smaller than the size of the irradiation field, and track at least part of the motion of the particle beam. As a result, the energy degrader may be lighter, which can reduce the amount of time that it takes to position the energy degrader plates in the path of the particle beam and thus reduce the treatment time. The energy degrader may track the particle beam in two directions (e.g., XY) or in three directions (e.g., XYZ). That is, the energy degrader may move in a plane perpendicular to the particle beam, or the energy degrader may move in a plane perpendicular to the particle beam and along a longitudinal direction of the particle beam. In this regard, any of the collimators described herein may also move in a plane perpendicular to the particle beam, or any of the collimators described herein may also move in a plane perpendicular to the particle beam and along a longitudinal direction of the particle beam. Movement of the collimator(s) and energy degrader(s) may be independent or coordinated.

Figure 20:
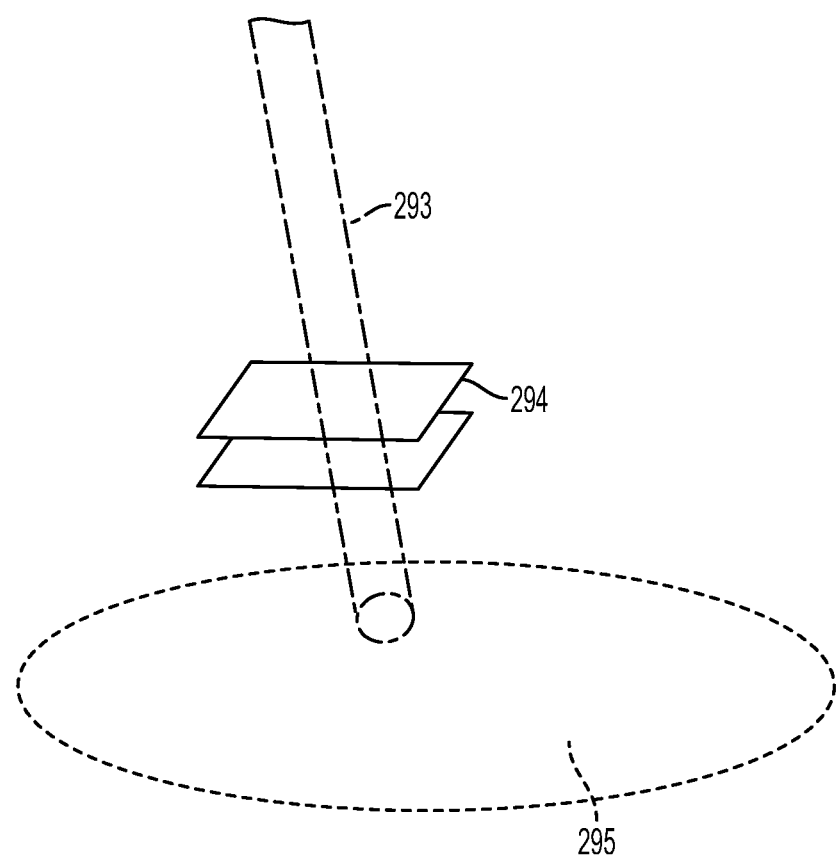
FIG. 20 is a perspective view of multiple pieces of an example energy degrader in the beam path to an irradiation target.

For example, an energy degrader may be comprised of multiple pieces, which may be plates or other structures constructed to absorb particle beam energy during treatment. Each piece may have the same area (XY) and thickness (Z) or different pieces may have different areas and thicknesses. Referring to FIG. 20, two or more pieces 294 having the same or different thicknesses may be placed in front an irradiation target 295 in the particle beam 293 path to achieve a particular amount of energy absorption. Alternatively, a single piece having a specified thickness may be placed in front of the beam to achieve a particular amount of energy absorption. For example, if a particular energy absorption is needed, the control computer may select a piece with the appropriate thickness to achieve that absorption.

In examples where two or more pieces are placed in front of the beam, those pieces may be assembled prior to placement or assembled dynamically during placement. For example, the control computer may select two pieces, arrange them, and then move the combination of the two pieces into the beam path. Alternatively, the control computer may select two pieces and then move the combination of the two pieces into the beam path simultaneously but not in combination (e.g., each may be moved with a separate robotic arm).

The energy degrader, or pieces thereof, may track movement of the particle beam across at least part of the irradiation field so as to achieve appropriate energy absorption, and thus beam depth penetration, at various points on the irradiation target. The treatment plan may dictate where the energy degrader needs to be at any particular time during treatment, and feedback from the ionization chamber may be used for positioning and position correction, if necessary. In some implementations, the precision with which the energy degrader needs to track the particle beam is based on the size of the degrader and the spot size of the particle beam at the point where the particle beam intersects the energy degrader.

Figure 21:
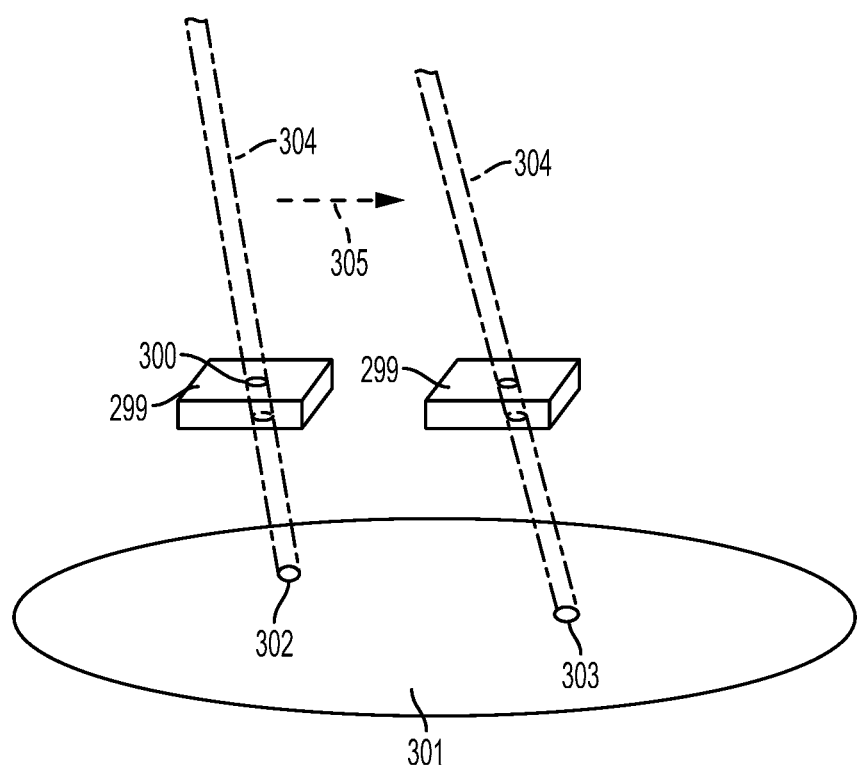
FIG. 21 is a perspective view illustrating movement of pieces of an energy degrader to track scanning of a particle beam.

More specifically, in some examples, the smaller that the surface area of the energy degrader is, the more closely movement of the energy degrader should track movement of the particle beam. Conversely, in other examples, the larger that the surface area of the energy degrader is, the less closely movement of the energy degrader needs to track movement of the particle beam. For example referring to FIG. 21, if the energy degrader 299 has a surface area that is close to a surface area of spot 300 at the point where the particle beam intersects the energy degrader, the energy degrader should track motion of the particle beam rather closely in order to ensure that the energy degrader is in front of the particle beam relative to irradiation target 301 at appropriate times during treatment. For example, motion of particle beam 304 from location 302 to location 303 would also require energy degrader 299 to move in the direction of arrow 305 to remain in the beam path, since the areas of the spot and the degrader are relatively close in size. As indicated, motion of the particle beam may be dictated by the treatment plan and detected through use of the ionization chamber and feedback to the control computer. This information may also be used to control movement of the energy degrader.

Figure 22:
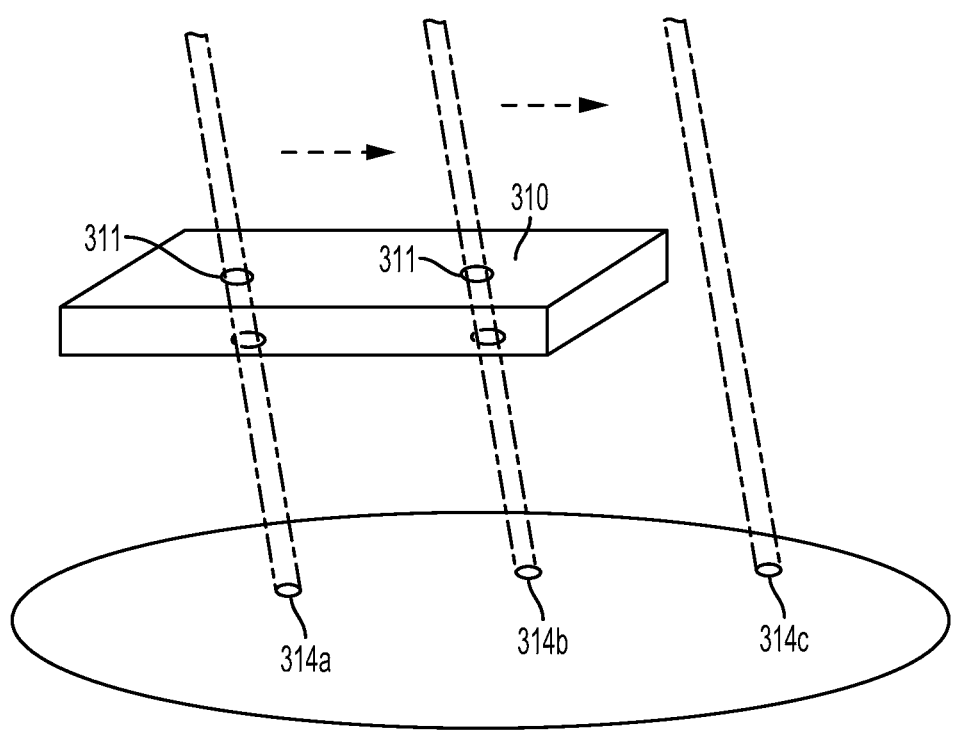
FIG. 22 is a perspective view illustrating situations where movement of pieces of an energy degrader is required, and is not required, to track scanning of a particle beam.

In some implementations, the movable energy degrader may be considerably larger than the particle beam spot. In these cases, the energy degrader need not track motion of the particle beam as closely in order to ensure that the energy degrader is in front of the particle beam at appropriate times during treatment. In fact, depending upon the size of the energy degrader, the energy degrader need not move at all in some cases where the particle beam moves. That is, for some motion of the particle beam, the energy degrader may remain stationary, but for other motion of the particle beam, the energy degrader also moves to intercept the particle beam. For example, FIG. 22 shows a case where the energy degrader 310 is considerably larger than particle beam spot 311 at the point where the particle beam intersects the energy degrader. As the particle beam spot moves from point 314a to point 314b, the energy degrader remains in the beam path even though the energy degrader has not moved. The control computer system, knowing the size of the degrader and the two spot positions, does not move the energy degrader in this case. Accordingly, in this case, the energy degrader need not track movement of the particle beam spot. However, when the spot moves to point 314c, the energy degrader (or piece(s) thereof) will move to track and intercept the beam so as to remain in the beam path. Accordingly, the size of the energy degrader relative to the beam spot is a factor in determining when, and by how much, the energy degrader is required to move during scanning.

In some implementations, the energy degrader may include multiple parts or pieces. For example, one part or piece may be used to track movement of the particle beam across part of an irradiation target (e.g., irradiation applied from the top of the irradiation target) and another part or piece may be used to track movement of the particle beam across another part of an irradiation target (e.g., irradiation applied from the bottom of the target).

The energy degrader (or pieces thereof) may have any shape, e.g., square, rectangular, circular, oval, irregular, regular, polygonal, spherical, cubical, tetrahedral, and so forth. The energy degrader (or pieces thereof) may have any appropriate size. For example, the energy degrader (or pieces thereof) may have a surface area this less than the area of the irradiation field, that is less than ¾ the area of the irradiation field, that is less than ½ the area of the irradiation field, that is less than ⅓ the area of the irradiation field, that is less than ¼ the area of the irradiation field, that is less than ⅕ the area of the irradiation field, or so forth. The energy degrader (or pieces thereof) may have a surface area that is less than twenty times the area of the particle beam spot at the irradiation field, that is less than fifteen times the area of the particle beam spot at the irradiation field, that is less than ten times the area of the particle beam spot at the irradiation field, that is less than nine times the area of the particle beam spot at the irradiation field, that is less than eight times the area of the particle beam spot at the irradiation field, that is less than seven times the area of the particle beam spot at the irradiation field, that is less than six times the area of the particle beam spot at the irradiation field, that is less than five times the area of the particle beam spot at the irradiation field, that is less than four times the area of the particle beam spot at the irradiation field, that is less than three times the area of the particle beam spot at the irradiation field, or that is less than two times the area of the particle beam spot at the irradiation field. In some implementations, the energy degrader (or pieces thereof) may have a surface area that is a multiple of the spot size, e.g., two times the spot size, three times the spot size, five times the spot size, ten times the spot size, and so forth.

In some implementations, each piece (e.g., layer of multiple layers) has a same size, shape, thickness and composition. In other implementations, different pieces may have different sizes, shapes thicknesses and compositions.

The movement of the example energy degraders described herein may be controlled in various ways. For example, the current through magnet 108 may correspond to the deflection of the particle beam by the magnet and, thus, the location of the particle beam spot on the irradiation target. So, for example, knowing the current through the magnet and the location of the irradiation target relative to the magnet, a computer system controlling operation of the scanning system can determine the projected location of the irradiation spot. And, knowing the location of the radiation spot, and the size of the energy degrader relative to the spot size, the computer system can control the energy degrader, to track (if necessary) movement of the irradiation spot along all or part of its motion, as described herein.

The example movable energy degraders described herein may be mounted to one or more computer-controlled robotic arms or other structures that also contain elements of the scanning system to control movement relative to the irradiation target. In implementations where the energy degrader includes more than one piece (e.g., multiple pieces or plates), there may be more than one robotic arm to independently control the different pieces of the energy degrader in accordance with the treatment plan. In some implementations, a single robotic arm may be configured to control the different pieces independently.

Different cross-sections of the irradiation target may be scanned according to different treatment plans. As described above, an energy degrader is used to control the scanning depth. In some implementations, the particle beam may be interrupted or redirected during configuration of the energy degrader. In other implementations, this need not be the case.

Described herein are examples of treating cross-sections of an irradiation target. These may be cross-sections that are roughly perpendicular to the direction of the particle beam. However, the concepts described herein are equally applicable to treating other portions of an irradiation target that are not cross-sections perpendicular to the direction of the particle beam. For example, an irradiation target may be segmented into spherical, cubical or other shaped volumes, and those volumes may be treated using the example processes, systems, and/or devices described herein.

The processes described herein may be used with a single particle accelerator, and any two or more of the features thereof described herein may be used with the single particle accelerator. The particle accelerator may be used in any type of medical or non-medical application. An example of a particle therapy system that may be used is provided below. Notably, the concepts described herein may be used in other systems not specifically described.

Figure 23:
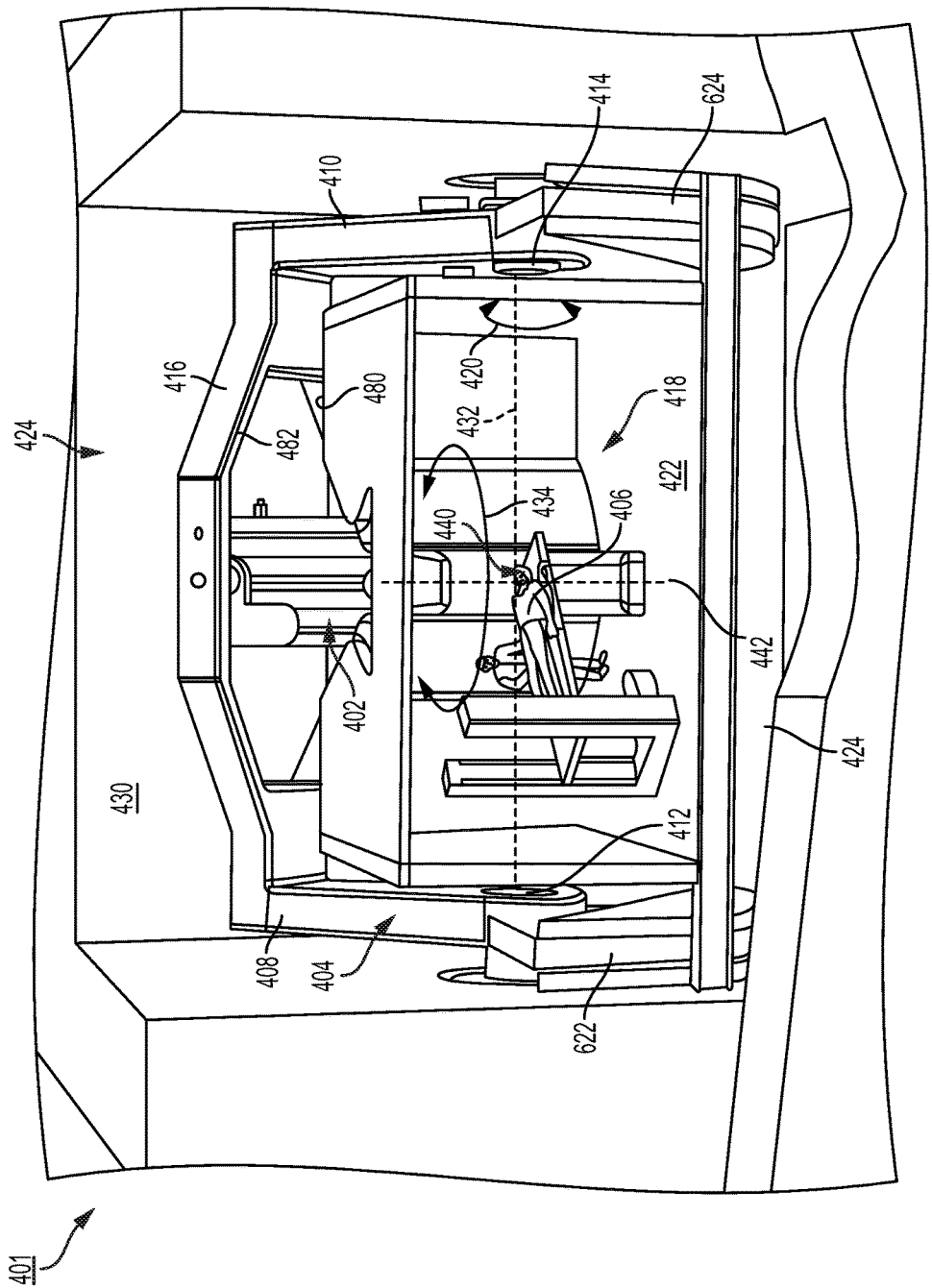
FIG. 23 is a perspective view of an example therapy system.
Figure 24:
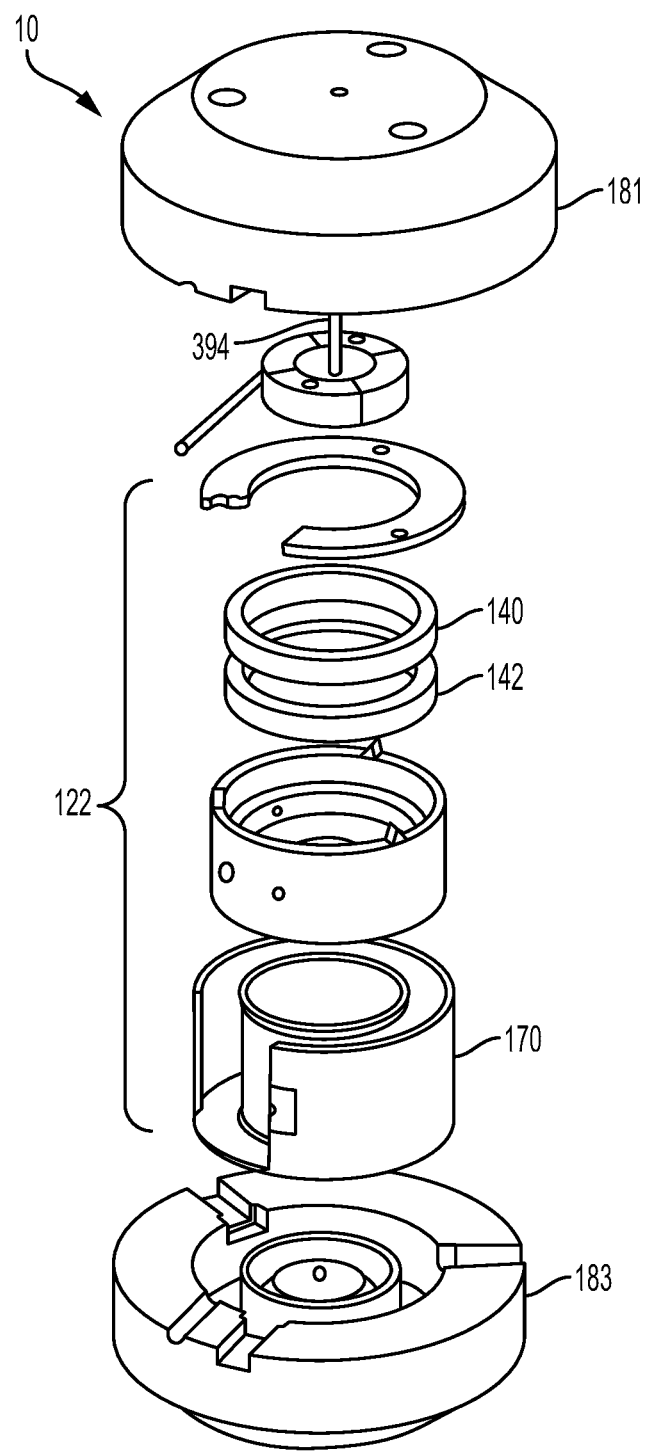
FIG. 24 is an exploded perspective view of components of an example synchrocyclotron for use in the particle therapy system.

Referring to FIG. 23, an example implementation of a charged particle radiation therapy system 401 includes a beam-producing particle accelerator 402 having a weight and size small enough to permit it to be mounted on a rotating gantry 404 with its output directed straight (that is, essentially directly) from the accelerator housing toward a patient 406. Particle accelerator 402 also includes a scanning system of a type described herein, which may operate as described with respect to FIGS. 3 to 22 and FIGS. 34 to 49.

In some implementations, the steel gantry has two legs 408, 410 mounted for rotation on two respective bearings 412, 414 that lie on opposite sides of the patient. The accelerator is supported by a steel truss 416 that is long enough to span a treatment area 418 in which the patient lies (e.g., twice as long as a tall person, to permit the person to be rotated fully within the space with any desired target area of the patient remaining in the line of the beam) and is attached stably at both ends to the rotating legs of the gantry.

In some examples, the rotation of the gantry is limited to a range 420 of less than 360 degrees, e.g., about 180 degrees, to permit a floor 422 to extend from a wall of the vault 424 that houses the therapy system into the patient treatment area. The limited rotation range of the gantry also reduces the required thickness of some of the walls (which are not directly aligned with the beam, e.g., wall 430), which provide radiation shielding of people outside the treatment area. A range of 180 degrees of gantry rotation is enough to cover all treatment approach angles, but providing a larger range of travel can be useful. For example the range of rotation may be between 180 and 330 degrees and still provide clearance for the therapy floor space. In other implementations, rotation is not limited as described above.

The horizontal rotational axis 432 of the gantry is located nominally one meter above the floor where the patient and therapist interact with the therapy system. This floor is positioned about 3 meters above the bottom floor of the therapy system shielded vault. The accelerator can swing under the raised floor for delivery of treatment beams from below the rotational axis. The patient couch moves and rotates in a substantially horizontal plane parallel to the rotational axis of the gantry. The couch can rotate through a range 434 of about 270 degrees in the horizontal plane with this configuration. This combination of gantry and patient rotational ranges and degrees of freedom allow the therapist to select virtually any approach angle for the beam. If needed, the patient can be placed on the couch in the opposite orientation and then all possible angles can be used.

In some implementations, the accelerator uses a synchrocyclotron configuration having a high magnetic field superconducting electromagnetic structure. Because the bend radius of a charged particle of a given kinetic energy is reduced in direct proportion to an increase in the magnetic field applied to it, the high magnetic field superconducting magnetic structure permits the accelerator to be made smaller and lighter. The synchrocyclotron uses a magnetic field that is uniform in rotation angle and falls off in strength with increasing radius. Such a field shape can be achieved regardless of the magnitude of the magnetic field, so in theory there is no upper limit to the magnetic field strength (and therefore the resulting particle energy at a fixed radius) that can be used in a synchrocyclotron.

The synchrocyclotron is supported on the gantry so that the beam is generated directly in line with the patient. The gantry permits rotation of the synchrocyclotron about a horizontal rotational axis that contains a point (isocenter 440) within, or near, the patient. The split truss that is parallel to the rotational axis, supports the synchrocyclotron on both sides.

Because the rotational range of the gantry is limited in some example implementations, a patient support area can be accommodated in a wide area around the isocenter. Because the floor can be extended broadly around the isocenter, a patient support table can be positioned to move relative to and to rotate about a vertical axis 442 through the isocenter so that, by a combination of gantry rotation and table motion and rotation, any angle of beam direction into any part of the patient can be achieved. In some implementations, the two gantry arms are separated by more than twice the height of a tall patient, allowing the couch with patient to rotate and translate in a horizontal plane above the raised floor.

Limiting the gantry rotation angle allows for a reduction in the thickness of at least one of the walls surrounding the treatment room. Thick walls, typically constructed of concrete, provide radiation protection to individuals outside the treatment room. A wall downstream of a stopping proton beam may be about twice as thick as a wall at the opposite end of the room to provide an equivalent level of protection. Limiting the range of gantry rotation enables the treatment room to be sited below earth grade on three sides, while allowing an occupied area adjacent to the thinnest wall reducing the cost of constructing the treatment room.

In the example implementation shown in FIG. 23, the superconducting synchrocyclotron 402 operates with a peak magnetic field in a pole gap of the synchrocyclotron of 8.8 Tesla. The synchrocyclotron produces a beam of protons having an energy of 250 MeV. In some implementations, the synchrocyclotron is a variable-energy machine, and is capable of outputting proton beams having different energies. In some implementations, the synchrocyclotron may produce a beam having a fixed energy. In some implementations the field strength could be in the range of 4 T to 20 T and the proton energy could be in the range of 150 to 300 MeV.

The radiation therapy system described in this example is used for proton radiation therapy, but the same principles and details can be applied in analogous systems for use in heavy ion (ion) treatment systems.

As shown in FIGS. 1, 2, 24, 25, and 26, an example synchrocyclotron 10 (e.g., 402 in FIG. 23) includes a magnet system 122 that contains a particle source 190, a radiofrequency drive system 191, and a beam extraction system 138. In this example, the magnetic field established by the magnet system has a shape appropriate to maintain focus of a contained proton beam using a combination of a split pair of annular superconducting coils 140, 142 and a pair of shaped ferromagnetic (e.g., low carbon steel) pole faces 144, 146.

The two superconducting magnet coils are centered on a common axis 147 and are spaced apart along the axis. The coils may be formed by of $Nb_3Sn$-based superconducting 0.8 mm diameter strands (that initially comprise a niobium-tin core surrounded by a copper sheath) deployed in a twisted cable-in-channel conductor geometry. After seven individual strands are cabled together, they are heated to cause a reaction that forms the final (brittle) superconducting material of the wire. After the material has been reacted, the wires are soldered into the copper channel (outer dimensions 3.18×2.54 mm and inner dimensions 2.08×2.08 mm) and covered with insulation (in this example, a woven fiberglass material). The copper channel containing the wires is then wound in a coil having a rectangular cross-section. The wound coil is then vacuum impregnated with an epoxy compound. The finished coils are mounted on an annular stainless steel reverse bobbin. Heater blankets may be placed at intervals in the layers of the windings to protect the assembly in the event of a magnet quench.

The entire coil can then be covered with copper sheets to provide thermal conductivity and mechanical stability and then contained in an additional layer of epoxy. The precompression of the coil can be provided by heating the stainless steel reverse bobbin and fitting the coils within the reverse bobbin. The reverse bobbin inner diameter is chosen so that when the entire mass is cooled to 4 K, the reverse bobbin stays in contact with the coil and provides some compression. Heating the stainless steel reverse bobbin to approximately 50 degrees C. and fitting coils at a temperature of 100 degrees Kelvin can achieve this.

Figure 25:
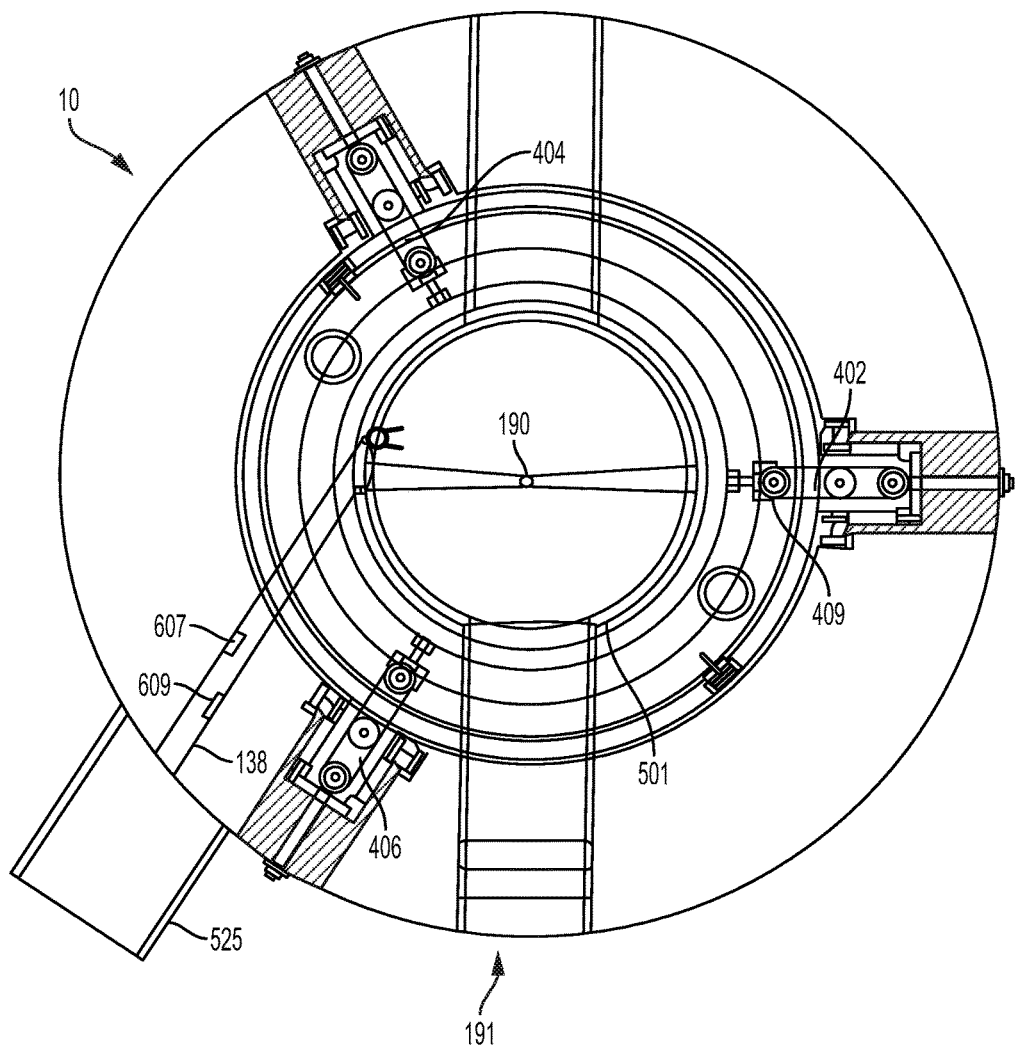
FIG. 25 is a cross-sectional view of the example synchrocyclotron.
Figure 26:
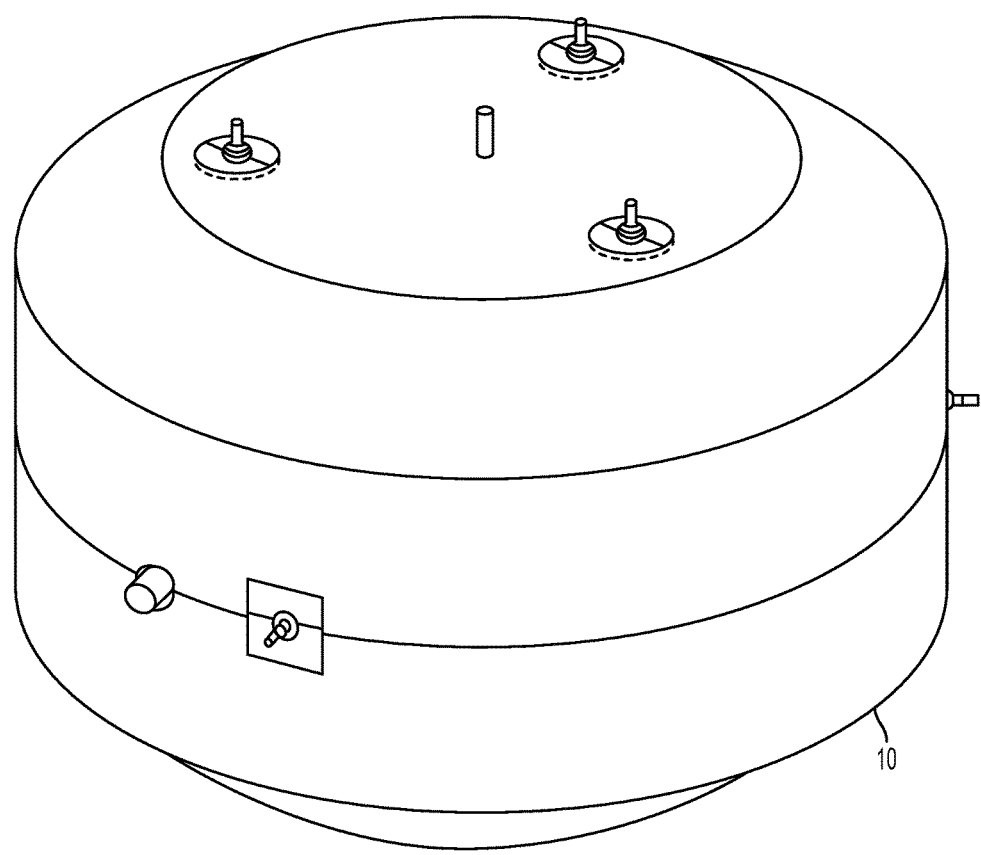
FIG. 26 is a perspective view of the example synchrocyclotron.

The geometry of the coil is maintained by mounting the coils in a "reverse" rectangular bobbin 156 to exert a restorative force that works against the distorting force produced when the coils are energized. As shown in FIG. 25, in some implementations, coil position is maintained relative to corresponding magnet pole pieces and the cryostat using a set of warm-to-cold support straps 402, 404, 406. Supporting the cold mass with thin straps reduces the heat leakage imparted to the cold mass by the rigid support system. The straps are arranged to withstand the varying gravitational force on the coil as the magnet rotates on board the gantry. They withstand the combined effects of gravity and the large de-centering force realized by the coil when it is perturbed from a perfectly symmetric position relative to the magnet yoke. Additionally the links act to reduce dynamic forces imparted on the coil as the gantry accelerates and decelerates when its position is changed. Each warm-to-cold support may include one S2 fiberglass link and one carbon fiber link. The carbon fiber link is supported across pins between the warm yoke and an intermediate temperature (50-70 K), and the S2 fiberglass link 409 is supported across the intermediate temperature pin and a pin attached to the cold mass. Each pin may be made of high strength stainless steel.

Referring to FIG. 1, the field strength profile as a function of radius is determined largely by choice of coil geometry and pole face shape; the pole faces 144, 146 of the permeable yoke material can be contoured to fine tune the shape of the magnetic field to ensure that the particle beam remains focused during acceleration.

The superconducting coils are maintained at temperatures near absolute zero (e.g., about 4 degrees Kelvin) by enclosing the coil assembly (the coils and the bobbin) inside an evacuated annular aluminum or stainless steel cryostatic chamber 170 (the cryostat) that provides a free space around the coil structure, except at a limited set of support points 171, 173. In an alternate version (e.g., FIG. 2) the outer wall of the cryostat may be made of low carbon steel to provide an additional return flux path for the magnetic field.

In some implementations, the temperature near absolute zero is achieved and maintained using one single-stage Gifford-McMahon cryo-cooler and three two-stage Gifford McMahon cryo-coolers. Each two stage cryo-cooler has a second stage cold end attached to a condenser that recondenses Helium vapor into liquid Helium. In some implementations, the temperature near absolute zero is achieved and maintained using a cooling channel (not shown) containing liquid helium, which is formed inside a superconducting coil support structure (e.g., the reverse bobbin), and which contains a thermal connection between the liquid helium in the channel and the corresponding superconducting coil.

In some implementations, the coil assembly and cryostatic chambers are mounted within and fully enclosed by two halves 181, 183 of a pillbox-shaped magnet yoke 100. The yoke 100 provides a path for the return magnetic field flux 184 and magnetically shields the volume 186 between the pole faces 144, 146 to prevent external magnetic influences from perturbing the shape of the magnetic field within that volume. The yoke also serves to decrease the stray magnetic field in the vicinity of the accelerator. In other implementations, the coil assembly and cryostatic chambers are mounted within and fully enclosed by a non-magnetic enclosure, and the path for return magnetic field flux is implemented using an active return system, an example of which is described above.

Figure 27:
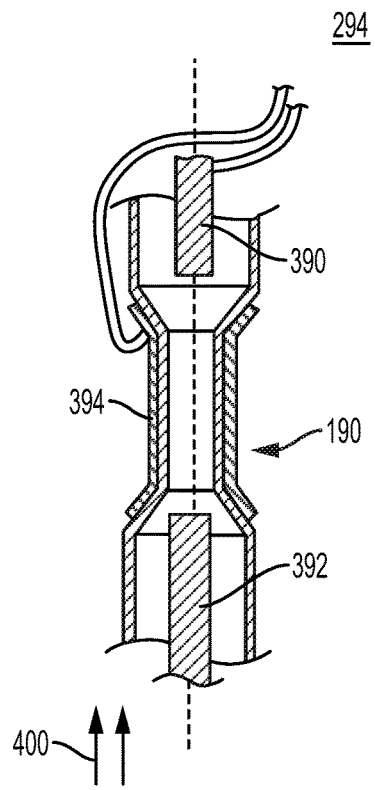
FIG. 27 is a cross-sectional view of an example ion source for use in the synchrocyclotron.

As shown in FIGS. 1 and 27, the synchrocyclotron includes a particle source 190 of a Penning ion gauge geometry located near the geometric center 192 of the magnet structure 182. The particle source may be as described below, or the particle source may be of the type described in U.S. patent application Ser. No. 11/948,662 (U.S. Pat. No. 8,581,523) incorporated herein by reference.

Particle source 190 is fed from a supply 399 of hydrogen through a gas line 393 and tube 394 that delivers gaseous hydrogen. Electric cables 294 carry an electric current from a current source to stimulate electron discharge from cathodes 392, 390 that are aligned with the magnetic field 400.

In this example, the discharged electrons ionize the gas exiting through a small hole from tube 394 to create a supply of positive ions (protons) for acceleration by one semicircular (dee-shaped) radio-frequency plate that spans half of the space enclosed by the magnet structure and one dummy dee plate. In the case of an interrupted particle source (an example of which is described in U.S. patent application Ser. No. 11/948,662), all (or a substantial part, e.g., a majority) of the tube containing plasma is removed at the acceleration region.

Figure 28:
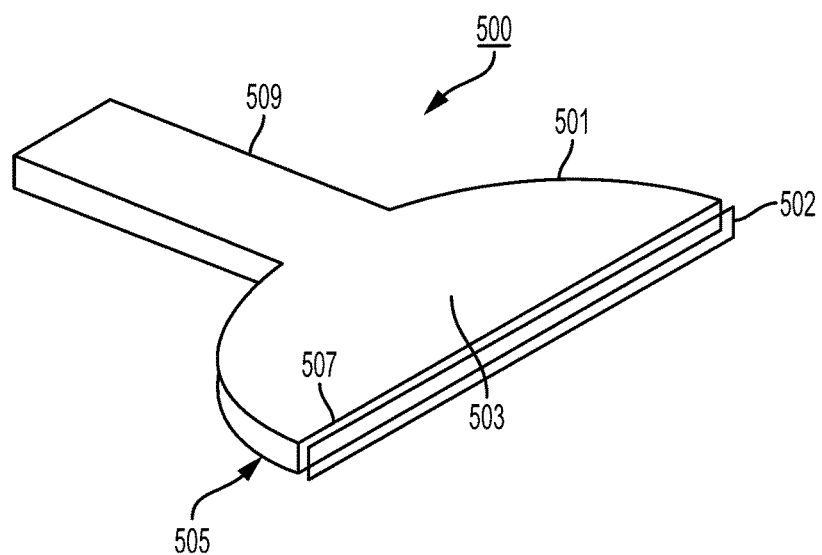
FIG. 28 is a perspective view of an example dee plate and an example dummy dee for use in the synchrocyclotron.

As shown in FIG. 28, the dee plate 500 is a hollow metal structure that has two semicircular surfaces 503, 505 that enclose a space 507 in which the protons are accelerated during half of their rotation around the space enclosed by the magnet structure. A duct 509 opening into the space 507 extends through the enclosure (e.g., the yoke or pole piece(s)) to an external location from which a vacuum pump can be attached to evacuate the space 507 and the rest of the space within a vacuum chamber in which the acceleration takes place. The dummy dee 502 comprises a rectangular metal ring that is spaced near to the exposed rim of the dee plate. The dummy dee is grounded to the vacuum chamber and magnet yoke. The dee plate 500 is driven by a radio-frequency signal that is applied at the end of a radiofrequency transmission line to impart an electric field in the space 507. The radio frequency electric field is made to vary in time as the accelerated particle beam increases in distance from the geometric center. The radio frequency electric field may be controlled in the manner described in U.S. patent application Ser. No. 11/948,359 (U.S. Pat. No. 8,933,650), entitled "Matching A Resonant Frequency Of A Resonant Cavity To A Frequency Of An Input Voltage", the contents of which are incorporated herein by reference.

For the beam emerging from the centrally located particle source to clear the particle source structure as it begins to spiral outward, a large voltage difference may be applied across the radio frequency plates. 20,000 Volts is applied across the radio frequency plates. In some versions from 8,000 to 20,000 Volts may be applied across the radio frequency plates. To reduce the power required to drive this large voltage, the magnet structure is arranged to reduce the capacitance between the radio frequency plates and ground. This may be done by forming holes with sufficient clearance from the radio frequency structures through the outer yoke and the cryostat housing and making sufficient space between the magnet pole faces.

The high voltage alternating potential that drives the dee plate has a frequency that is swept downward during the accelerating cycle to account for the increasing relativistic mass of the protons and the decreasing magnetic field. The dummy dee does not require a hollow semi-cylindrical structure as it is at ground potential along with the vacuum chamber walls. Other plate arrangements could be used such as more than one pair of accelerating electrodes driven with different electrical phases or multiples of the fundamental frequency. The RF structure can be tuned to keep the Q high during the required frequency sweep by using, for example, a rotating capacitor having intermeshing rotating and stationary blades. During each meshing of the blades, the capacitance increases, thus lowering the resonant frequency of the RF structure. The blades can be shaped to create a precise frequency sweep required. A drive motor for the rotating condenser can be phase locked to the RF generator for precise control. One bunch of particles may be accelerated during each meshing of the blades of the rotating condenser.

The vacuum chamber in which the acceleration occurs is a generally cylindrical container that is thinner in the center and thicker at the rim. The vacuum chamber encloses the RF plates and the particle source and is evacuated by a vacuum pump. Maintaining a high vacuum reduces the chances that accelerating ions are not lost to collisions with gas molecules and enables the RF voltage to be kept at a higher level without arcing to ground.

Protons (or other ions) traverse a generally spiral orbital path beginning at the particle source. In half of each loop of the spiral path, the protons gain energy as they pass through the RF electric field. As the protons gain energy, the radius of the central orbit of each successive loop of their spiral path is larger than the prior loop until the loop radius reaches the maximum radius of the pole face. At that location a magnetic and electric field perturbation directs protons into an area where the magnetic field rapidly decreases, and the protons depart the area of the high magnetic field and are directed through an evacuated tube, referred to herein as the extraction channel, to exit the synchrocyclotron. A magnetic regenerator may be used to change the magnetic field perturbation to direct the protons. The protons exiting will tend to disperse as they enter an area of markedly decreased magnetic field that exists in the room around the synchrocyclotron. Beam shaping elements 607, 609 in the extraction channel 138 (FIG. 25) redirect the protons so that they stay in a straight beam of limited spatial extent.

As the beam exits the extraction channel it is passed through a beam formation system 525 (FIG. 25), which may include a scanning system of the type described herein. Beam formation system 525 may be used in conjunction with an inner gantry that controls application of the beam.

Stray magnetic fields exiting from the synchrocyclotron may be limited by both a magnet yoke (which also serves as a shield) and a separate magnetic shield 514 (e.g., FIG. 1). The separate magnetic shield includes of a layer 517 of ferromagnetic material (e.g., steel or iron) that encloses the pillbox yoke, separated by a space 516. This configuration that includes a sandwich of a yoke, a space, and a shield achieves adequate shielding for a given leakage magnetic field at lower weight. As described above, in some implementations, an active return system may be used in place of, or to augment, the operation of the magnetic yoke and shield.

Referring to FIG. 23, the gantry allows the synchrocyclotron to be rotated about a horizontal rotational axis 432. The truss structure 416 has two generally parallel spans 480, 482. The synchrocyclotron is cradled between the spans about midway between the legs. The gantry is balanced for rotation about the bearings using counterweights 622, 624 mounted on ends of the legs opposite the truss.

The gantry is driven to rotate by an electric motor mounted to one or both of the gantry legs and connected to the bearing housings by drive gears. The rotational position of the gantry is derived from signals provided by shaft angle encoders incorporated into the gantry drive motors and the drive gears.

At the location at which the ion beam exits the synchrocyclotron, the beam formation system 525 acts on the ion beam to give it properties suitable for patient treatment. For example, the beam may be spread and its depth of penetration varied to provide uniform radiation across a given target volume. The beam formation system may include active scanning elements as described herein.

All of the active systems of the synchrocyclotron (the current driven superconducting coils, the RF-driven plates, the vacuum pumps for the vacuum acceleration chamber and for the superconducting coil cooling chamber, the current driven particle source, the hydrogen gas source, and the RF plate coolers, for example), may be controlled by appropriate synchrocyclotron control electronics (not shown), which may include, e.g., one or more processing devices executing instructions from memory to effect control.

Figure 29:
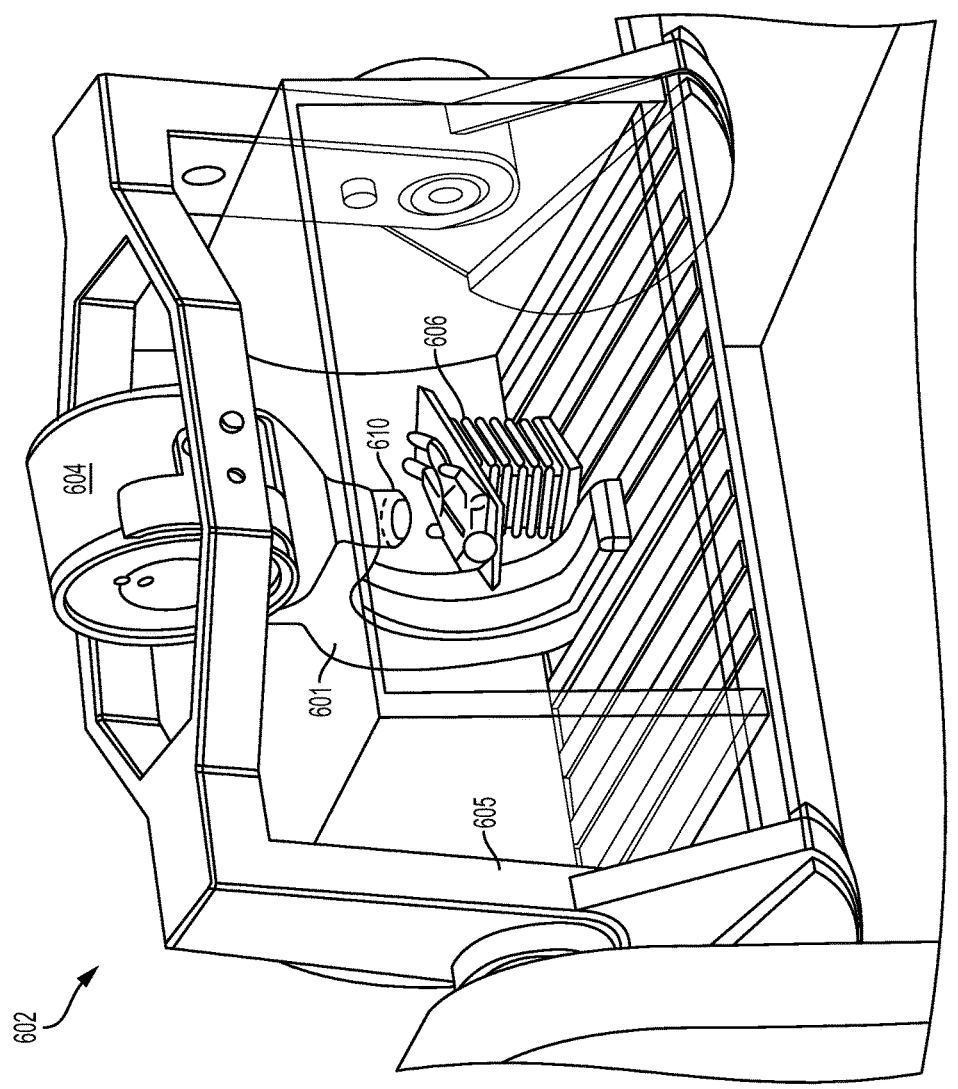
FIG. 29 shows a patient positioned within an example inner gantry of the example particle therapy system in a treatment room.

As explained above, referring to system 602 of FIG. 29, a beam-producing particle accelerator, in this case synchrocyclotron 604 (which may include any and all features described herein), may be mounted on rotating gantry 605. Rotating gantry 605 is of the type described herein, and can angularly rotate around patient support 606. This feature enables synchrocyclotron 604 to provide a particle beam essentially directly to the patient from various angles. For example, as in FIG. 29, if synchrocyclotron 604 is above patient support 606, the particle beam may be directed downwards toward the patient. Alternatively, if synchrocyclotron 604 is below patient support 606, the particle beam may be directed upwards toward the patient. The particle beam is applied essentially directly to the patient in the sense that an intermediary beam routing mechanism is not required. A routing mechanism, in this context, is different from a shaping or sizing mechanism in that a shaping or sizing mechanism does not re-route the beam, but rather sizes and/or shapes the beam while maintaining the same general trajectory of the beam.

Figure 30:
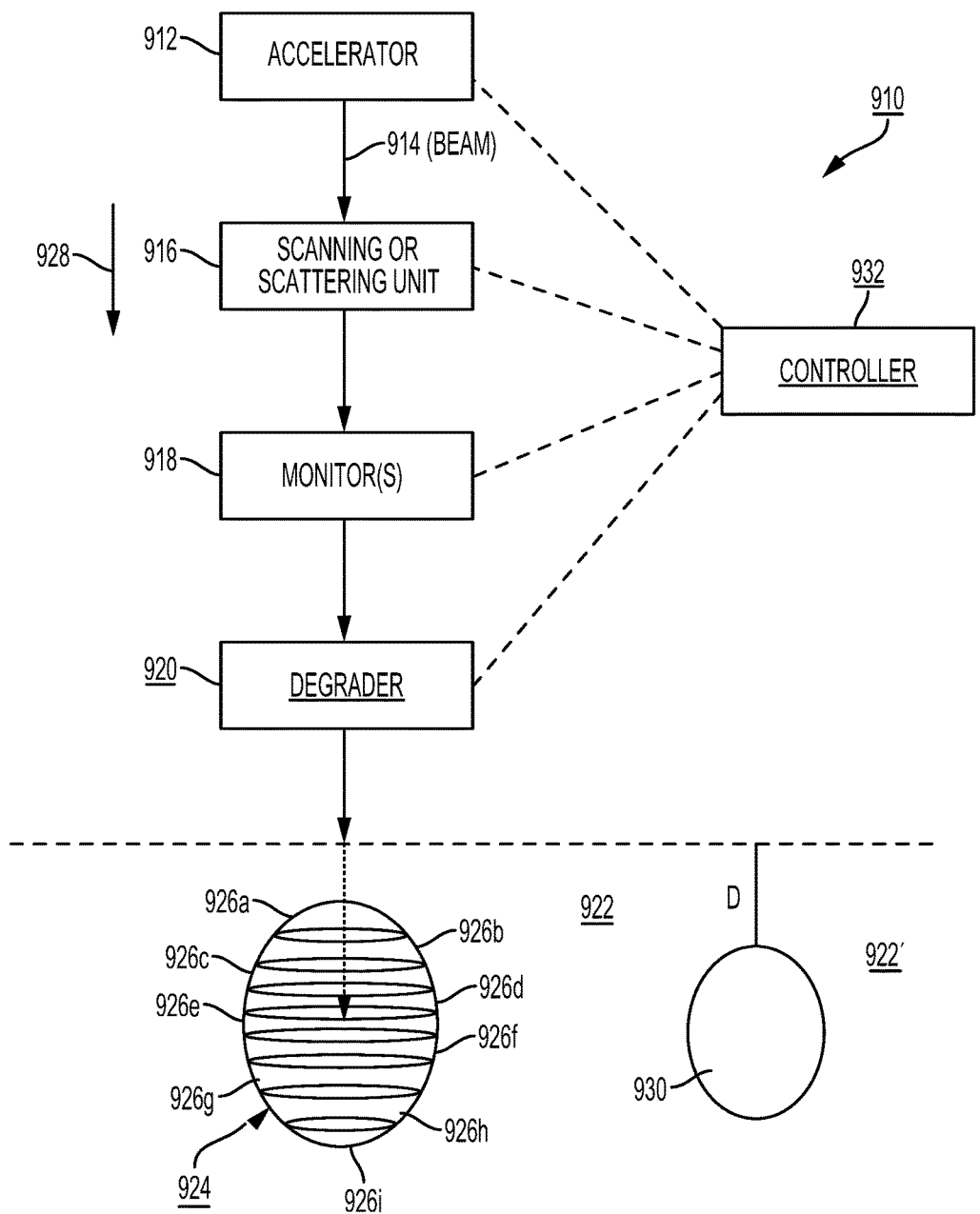
FIG. 30 is a conceptual view of an example particle therapy system that may use a variable-energy particle accelerator.

The particle accelerator used in the example particle therapy systems and example scanning systems described herein may be a variable-energy particle accelerator, an example of which is described below The energy of an extracted particle beam (the particle beam output from the accelerator) can affect the use of the particle beam during treatment. In some machines, the energy of the particle beam (or particles in the particle beam) does not increase after extraction. However, the energy may be reduced based on treatment needs after the extraction and before the treatment. Referring to FIG. 30, an example treatment system 910 includes an accelerator 912, e.g., a synchrocyclotron, from which a particle (e.g., proton) beam 914 having a variable energy is extracted to irradiate a target volume 924 of a body 922. Optionally, one or more additional devices, such as a scanning unit 916 or a scattering unit 916, one or more monitoring units 918, and an energy degrader 920, are placed along the irradiation direction 928. The devices intercept the cross-section of the extracted beam 914 and alter one or more properties of the extracted beam for the treatment.

A target volume to be irradiated (an irradiation target) by a particle beam for treatment typically has a three-dimensional configuration. In some examples, to carry-out the treatment, the target volume is divided into layers along the irradiation direction of the particle beam so that the irradiation can be done on a layer-by-layer basis. For certain types of particles, such as protons, the penetration depth (or which layer the beam reaches) within the target volume is largely determined by the energy of the particle beam. A particle beam of a given energy does not reach substantially beyond a corresponding penetration depth for that energy. To move the beam irradiation from one layer to another layer of the target volume, the energy of the particle beam is changed.

In the example shown in FIG. 30, the target volume 924 is divided into nine layers 926a-926i along the irradiation direction 928. In an example process, the irradiation starts from the deepest layer 926i, one layer at a time, gradually to the shallower layers and finishes with the shallowest layer 926a. Before application to the body 922, the energy of the particle beam 914 is controlled to be at a level to allow the particle beam to stop at a desired layer, e.g., the layer 926d, without substantially penetrating further into the body or the target volume, e.g., the layers 926e-926i or deeper into the body. In some examples, the desired energy of the particle beam 914 decreases as the treatment layer becomes shallower relative to the particle acceleration. In some examples, the beam energy difference for treating adjacent layers of the target volume 924 is about 3 MeV to about 100 MeV, e.g., about 10 MeV to about 80 MeV, although other differences may also be possible, depending on, e.g., the thickness of the layers and the properties of the beam.

The energy variation for treating different layers of the target volume 924 can be performed at the accelerator 912 (e.g., the accelerator can vary the energy) so that, in some implementations, no additional energy variation is required after the particle beam is extracted from the accelerator 912. So, the optional energy degrader 920 in the treatment system 10 may be eliminated from the system. In some implementations, the accelerator 912 can output particle beams having an energy that varies between about 100 MeV and about 300 MeV, e.g., between about 115 MeV and about 250 MeV. The variation can be continuous or non-continuous, e.g., one step at a time. In some implementations, the variation, continuous or non-continuous, can take place at a relatively high rate, e.g., up to about 50 MeV per second or up to about 20 MeV per second. Non-continuous variation can take place one step at a time with a step size of about 10 MeV to about 90 MeV.

When irradiation is complete in one layer, the accelerator 912 can vary the energy of the particle beam for irradiating a next layer, e.g., within several seconds or within less than one second. In some implementations, the treatment of the target volume 924 can be continued without substantial interruption or even without any interruption. In some situations, the step size of the non-continuous energy variation is selected to correspond to the energy difference needed for irradiating two adjacent layers of the target volume 924. For example, the step size can be the same as, or a fraction of, the energy difference.

In some implementations, the accelerator 912 and the degrader 920 collectively vary the energy of the beam 914. For example, the accelerator 912 provides a coarse adjustment and the degrader 920 provides a fine adjustment or vice versa. In this example, the accelerator 912 can output the particle beam that varies energy with a variation step of about 10-80 MeV, and the degrader 920 adjusts (e.g., reduces) the energy of the beam at a variation step of about 2-10 MeV.

The reduced use (or absence) of the energy degrader, such as a range modulator, may help to maintain properties and quality of the output beam from the accelerator, e.g., beam intensity. The control of the particle beam can be performed at the accelerator. Side effects, e.g., from neutrons generated when the particle beam passes the degrader 920 can be reduced or eliminated.

The energy of the particle beam 914 may be adjusted to treat another target volume 930 in another body or body part 922' after completing treatment in target volume 924. The target volumes 924, 930 may be in the same body (or patient), or in different patients. It is possible that the depth D of the target volume 930 from a surface of body 922' is different from that of the target volume 924. Although some energy adjustment may be performed by the degrader 920, the degrader 912 may only reduce the beam energy and not increase the beam energy.

In this regard, in some cases, the beam energy required for treating target volume 930 is greater than the beam energy required to treat target volume 924. In such cases, the accelerator 912 may increase the output beam energy after treating the target volume 924 and before treating the target volume 930. In other cases, the beam energy required for treating target volume 930 is less than the beam energy required to treat target volume 924. Although the degrader 920 can reduce the energy, the accelerator 912 can be adjusted to output a lower beam energy to reduce or eliminate the use of the degrader 920. The division of the target volumes 924, 930 into layers can be different or the same. The target volume 930 can be treated similarly on a layer by layer basis to the treatment of the target volume 924.

The treatment of the different target volumes 924, 930 on the same patient may be substantially continuous, e.g., with the stop time between the two volumes being no longer than about 30 minutes or less, e.g., 25 minutes or less, 20 minutes or less, 15 minutes or less, 10 minutes or less, 5 minutes or less, or 1 minute or less. As explained herein, the accelerator 912 can be mounted on a movable gantry and the movement of the gantry can move the accelerator to aim at different target volumes. In some situations, the accelerator 912 can complete the energy adjustment of the output beam 914 during the time the treatment system makes adjustment (such as moving the gantry) after completing the treatment of the target volume 924 and before starting treating the target volume 930. After the alignment of the accelerator and the target volume 930, the treatment can begin with the adjusted, desired beam energy. Beam energy adjustment for different patients can also be completed relatively efficiently. In some examples, all adjustments, including increasing/reducing beam energy and/or moving the gantry are done within about 30 minutes, e.g., within about 25 minutes, within about 20 minutes, within about 15 minutes, within about 10 minutes or within about 5 minutes.

In the same layer of a target volume, an irradiation dose may be applied by moving the beam across the two-dimensional surface of the layer (which is sometimes called scanning beam) using a scanning unit 916. Alternatively, the layer can be irradiated by passing the extracted beam through one or more scatterers of the scattering unit 16 (which is sometimes called scattering beam).

Beam properties, such as energy and intensity, can be selected before a treatment or can be adjusted during the treatment by controlling the accelerator 912 and/or other devices, such as the scanning unit/scatterer(s) 916, the degrader 920, and others not shown in the figures. In example implementations, system 910 includes a controller 932, such as a computer, in communication with one or more devices in the system. Control can be based on results of the monitoring performed by the one or more monitors 918, e.g., monitoring of the beam intensity, dose, beam location in the target volume, etc. Although the monitors 918 are shown to be between the device 916 and the degrader 920, one or more monitors can be placed at other appropriate locations along the beam irradiation path. Controller 932 can also store a treatment plan for one or more target volumes (for the same patient and/or different patients). The treatment plan can be determined before the treatment starts and can include parameters, such as the shape of the target volume, the number of irradiation layers, the irradiation dose for each layer, the number of times each layer is irradiated, etc. The adjustment of a beam property within the system 910 can be performed based on the treatment plan. Additional adjustment can be made during the treatment, e.g., when deviation from the treatment plan is detected.

In some implementations, the accelerator 912 is configured to vary the energy of the output particle beam by varying the magnetic field in which the particle beam is accelerated. In an example implementation, one or more sets of coils receives variable electrical current to produce a variable magnetic field in the cavity. In some examples, one set of coils receives a fixed electrical current, while one or more other sets of coils receives a variable current so that the total current received by the coil sets varies. In some implementations, all sets of coils are superconducting. In other implementations, some sets of coils, such as the set for the fixed electrical current, are superconducting, while other sets of coils, such as the one or more sets for the variable current, are non-superconducting. In some examples, all sets of coils are non-superconducting.

Generally, the magnitude of the magnetic field is scalable with the magnitude of the electrical current. Adjusting the total electric current of the coils in a predetermined range can generate a magnetic field that varies in a corresponding, predetermined range. In some examples, a continuous adjustment of the electrical current can lead to a continuous variation of the magnetic field and a continuous variation of the output beam energy. Alternatively, when the electrical current applied to the coils is adjusted in a non-continuous, step-wise manner, the magnetic field and the output beam energy also varies accordingly in a non-continuous (step-wise) manner. The scaling of the magnetic field to the current can allow the variation of the beam energy to be carried out relatively precisely, although sometimes minor adjustment other than the input current may be performed.

In some implementations, to output particle beams having a variable energy, the accelerator 912 is configured to apply RF voltages that sweep over different ranges of frequencies, with each range corresponding to a different output beam energy. For example, if the accelerator 912 is configured to produce three different output beam energies, the RF voltage is capable of sweeping over three different ranges of frequencies. In another example, corresponding to continuous beam energy variations, the RF voltage sweeps over frequency ranges that continuously change. The different frequency ranges may have different lower frequency and/or upper frequency boundaries.

The extraction channel may be configured to accommodate the range of different energies produced by the variable-energy particle accelerator. For example the extraction channel may be large enough to support the highest and lowest energies produced by the particle accelerator. That is, the extraction channel may be sized or otherwise configured to receive and to transmit particles within that range of energies. Particle beams having different energies can be extracted from the accelerator 912 without altering the features of the regenerator that is used for extracting particle beams having a single energy. In other implementations, to accommodate the variable particle energy, the regenerator can be moved to disturb (e.g., change) different particle orbits in the manner described above and/or iron rods (magnetic shims) can be added or removed to change the magnetic field bump provided by the regenerator. More specifically, different particle energies will typically be at different particle orbits within the cavity. By moving the regenerator, it is possible to intercept a particle orbit at a specified energy and thereby provide the correct perturbation of that orbit so that particles at the specified energy reach the extraction channel. In some implementations, movement of the regenerator (and/or addition/removal of magnetic shims) is performed in real-time to match real-time changes in the particle beam energy output by the accelerator. In other implementations, particle energy is adjusted on a per-treatment basis, and movement of the regenerator (and/or addition/removal of magnetic shims) is performed in advance of the treatment. In either case, movement of the regenerator (and/or addition/removal of magnetic shims) may be computer controlled. For example, a computer may control one or more motors that effect movement of the regenerator and/or magnetic shims.

In some implementations, the regenerator is implemented using one or more magnetic shims that are controllable to move to the appropriate location(s).

As an example, table 1 shows three example energy levels at which example accelerator 912 can output particle beams. The corresponding parameters for producing the three energy levels are also listed. In this regard, the magnet current refers to the total electrical current applied to the one or more coil sets in the accelerator 912; the maximum and minimum frequencies define the ranges in which the RF voltage sweeps; and "r" is the radial distance of a location to a center of the cavity in which the particles are accelerated.

TABLE 1

Examples of beam energies and respective parameters.

| Beam Energy (MeV) | Magnet Current (Amps) | Maximum Frequency (MHz) | Minimum Frequency (MHz) | Magnetic Field at r = 0 mm (Tesla) | Magnetic Field at r = 298 mm (Tesla) |
|---|---|---|---|---|---|
| 250 | 1990 | 132 | 99 | 8.7 | 8.2 |
| 235 | 1920 | 128 | 97 | 8.4 | 8.0 |
| 211 | 1760 | 120 | 93 | 7.9 | 7.5 |

Details that may be included in an example particle accelerator that produces charged particles having variable energies are described below. The accelerator can be a synchrocyclotron and the particles may be protons. The particles may be output as pulsed beams. The energy of the beam output from the particle accelerator can be varied during the treatment of one target volume in a patient, or between treatments of different target volumes of the same patient or different patients. In some implementations, settings of the accelerator are changed to vary the beam energy when no beam (or particles) is output from the accelerator. The energy variation can be continuous or non-continuous over a desired range.

Referring to the example shown in FIG. 1, the particle accelerator (e.g., a synchrocyclotron), which may be a variable-energy particle accelerator like accelerator 912 described above, may be configured to output particle beams that have a variable energy. The range of the variable energy can have an upper boundary that is about 200 MeV to about 300 MeV or higher, e.g., 200 MeV, about 205 MeV, about 210 MeV, about 215 MeV, about 220 MeV, about 225 MeV, about 230 MeV, about 235 MeV, about 240 MeV, about 245 MeV, about 250 MeV, about 255 MeV, about 260 MeV, about 265 MeV, about 270 MeV, about 275 MeV, about 280 MeV, about 285 MeV, about 290 MeV, about 295 MeV, or about 300 MeV or higher. The range can also have a lower boundary that is about 100 MeV or lower to about 200 MeV, e.g., about 100 MeV or lower, about 105 MeV, about 110 MeV, about 115 MeV, about 120 MeV, about 125 MeV, about 130 MeV, about 135 MeV, about 140 MeV, about 145 MeV, about 150 MeV, about 155 MeV, about 160 MeV, about 165 MeV, about 170 MeV, about 175 MeV, about 180 MeV, about 185 MeV, about 190 MeV, about 195 MeV, about 200 MeV.

In some examples, the variation is non-continuous and the variation step can have a size of about 10 MeV or lower, about 15 MeV, about 20 MeV, about 25 MeV, about 30 MeV, about 35 MeV, about 40 MeV, about 45 MeV, about 50 MeV, about 55 MeV, about 60 MeV, about 65 MeV, about 70 MeV, about 75 MeV, or about 80 MeV or higher. Varying the energy by one step size can take no more than 30 minutes, e.g., about 25 minutes or less, about 20 minutes or less, about 15 minutes or less, about 10 minutes or less, about 5 minutes or less, about 1 minute or less, or about 30 seconds or less. In other examples, the variation is continuous and the accelerator can adjust the energy of the particle beam at a relatively high rate, e.g., up to about 50 MeV per second, up to about 45 MeV per second, up to about 40 MeV per second, up to about 35 MeV per second, up to about 30 MeV per second, up to about 25 MeV per second, up to about 20 MeV per second, up to about 15 MeV per second, or up to about 10 MeV per second. The accelerator can be configured to adjust the particle energy both continuously and non-continuously. For example, a combination of the continuous and non-continuous variation can be used in a treatment of one target volume or in treatments of different target volumes. Flexible treatment planning and flexible treatment can be achieved.

A particle accelerator that outputs a particle beam having a variable energy can provide accuracy in irradiation treatment and reduce the number of additional devices (other than the accelerator) used for the treatment. For example, the use of degraders for changing the energy of an output particle beam may be reduced or eliminated for all or part of the treatment. The properties of the particle beam, such as intensity, focus, etc. can be controlled at the particle accelerator and the particle beam can reach the target volume without substantial disturbance from the additional devices. The relatively high variation rate of the beam energy can reduce treatment time and allow for efficient use of the treatment system.

Figure 33:
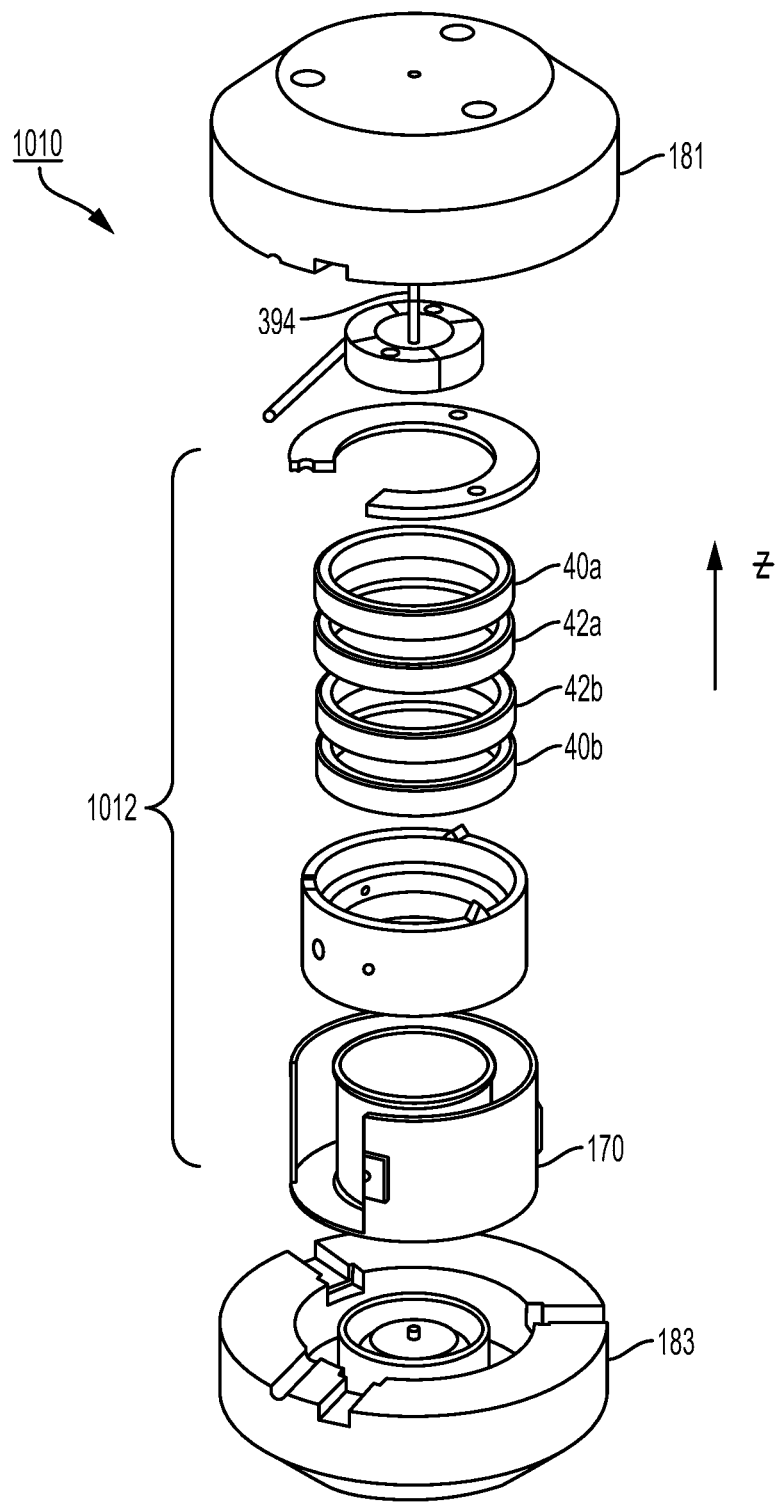
FIG. 33 is a perspective, exploded view of an example magnet system that may be used in a variable-energy particle accelerator.

In some implementations, the accelerator, such as the synchrocyclotron of FIG. 1, accelerates particles or particle beams to variable energy levels by varying the magnetic field in the accelerator, which can be achieved by varying the electrical current applied to coils for generating the magnetic field. As explained above, an example synchrocyclotron (e.g., FIG. 1) includes a magnet system that contains a particle source, a radiofrequency drive system, and a beam extraction system. FIG. 33 shows an example of a magnet system 1010 that may be used in a variable-energy accelerator. In this example implementation, the magnetic field established by the magnet system 1012 can vary by about 5% to about 35% of a maximum value of the magnetic field that two sets of coils 40a and 40b, and 42a and 42b are capable of generating. The magnetic field established by the magnet system has a shape appropriate to maintain focus of a contained proton beam using a combination of the two sets of coils and a pair of shaped ferromagnetic (e.g., low carbon steel) structures, examples of which are provided above.

Each set of coils may be a split pair of annular coils to receive electrical current. In some situations, both sets of coils are superconducting. In other situations, only one set of the coils is superconducting and the other set is non-superconducting or normal conducting (also discussed further below). It is also possible that both sets of coils are non-superconducting. Suitable superconducting materials for use in the coils include niobium-3 tin (Nb3Sn) and/or niobium-titanium. Other normal conducting materials can include copper. Examples of the coil set constructions are described further below.

The two sets of coils can be electrically connected serially or in parallel. In some implementations, the total electrical current received by the two sets of coils can include about 2 million ampere turns to about 10 million ampere turns, e.g., about 2.5 to about 7.5 million ampere turns or about 3.75 million ampere turns to about 5 million ampere turns. In some examples, one set of coils is configured to receive a fixed (or constant) portion of the total variable electrical current, while the other set of coils is configured to receive a variable portion of the total electrical current. The total electrical current of the two coil sets varies with the variation of the current in one coil set. In other situations, the electrical current applied to both sets of coils can vary. The variable total current in the two sets of coils can generate a magnetic field having a variable magnitude, which in turn varies the acceleration pathways of the particles and produces particles having variable energies.

Generally, the magnitude of the magnetic field generated by the coil(s) is scalable to the magnitude of the total electrical current applied to the coil(s). Based on the scalability, in some implementations, linear variation of the magnetic field strength can be achieved by linearly changing the total current of the coil sets. The total current can be adjusted at a relatively high rate that leads to a relatively high-rate adjustment of the magnetic field and the beam energy.

In the example reflected in Table 1 above, the ratio between values of the current and the magnetic field at the geometric center of the coil rings is: 1990:8.7 (approximately 228.7:1); 1920:8.4 (approximately 228.6:1); 1760: 7.9 (approximately 222.8:1). Accordingly, adjusting the magnitude of the total current applied to a superconducting coil(s) can proportionally (based on the ratio) adjust the magnitude of the magnetic field.

Figure 31:
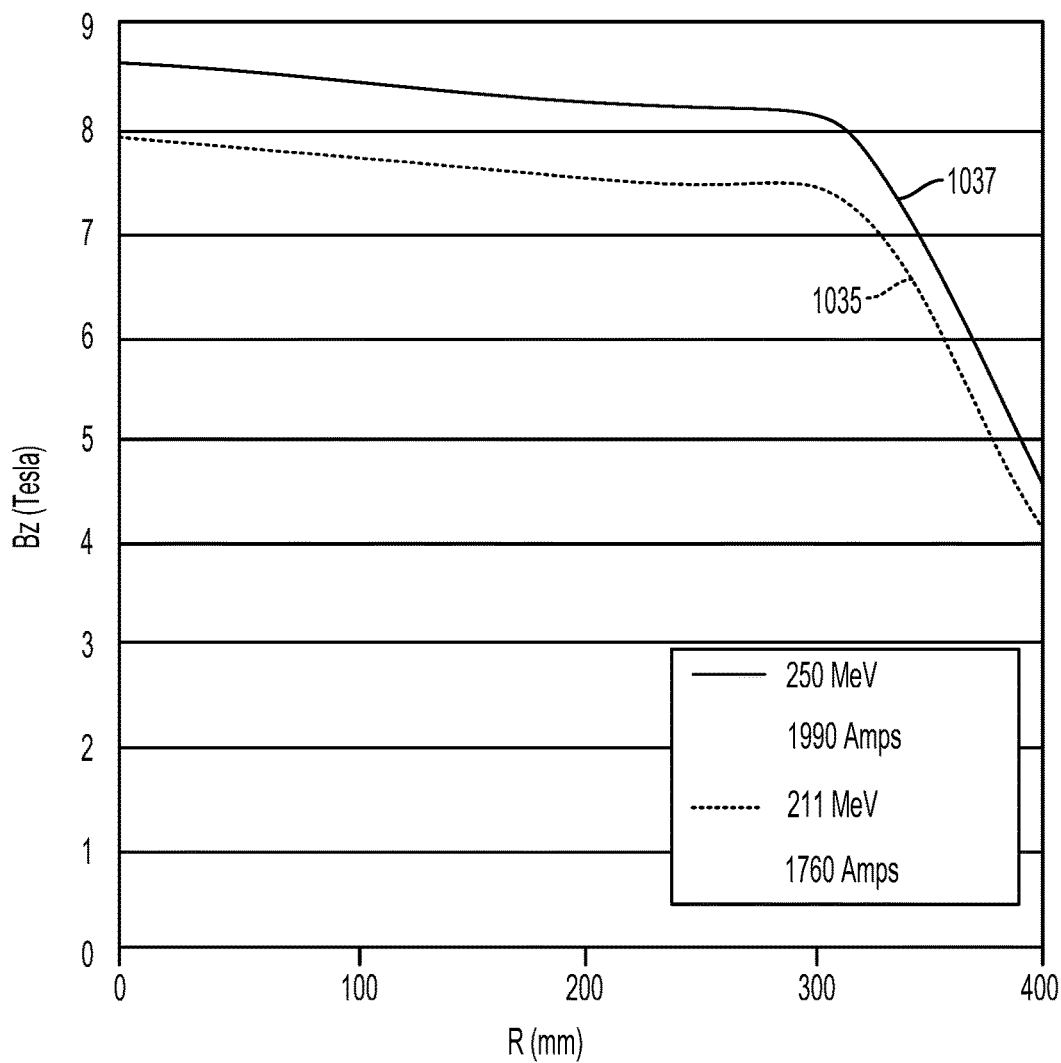
FIG. 31 is an example graph showing energy and current for variations in magnetic field and distance in a particle accelerator.

The scalability of the magnetic field to the total electrical current in the example of Table 1 is also shown in the plot of FIG. 31, where Bz is the magnetic field along the Z direction; and R is the radial distance measured from a geometric center of the coil rings along a direction perpendicular to the Z direction. The magnetic field has the highest value at the geometric center, and decreases as the distance R increases. The curves 1035, 1037 represent the magnetic field generated by the same coil sets receiving different total electrical current: 1760 Amperes and 1990 Amperes, respectively. The corresponding energies of the extracted particles are 211 MeV and 250 MeV, respectively. The two curves 1035, 1037 have substantially the same shape and the different parts of the curves 1035, 1037 are substantially parallel. As a result, either the curve 1035 or the curve 1037 can be linearly shifted to substantially match the other curve, indicating that the magnetic field is scalable to the total electrical current applied to the coil sets.

In some implementations, the scalability of the magnetic field to the total electrical current may not be perfect. For example, the ratio between the magnetic field and the current calculated based on the example shown in table 1 is not constant. Also, as shown in FIG. 31, the linear shift of one curve may not perfectly match the other curve. In some implementations, the total current is applied to the coil sets under the assumption of perfect scalability. The target magnetic field (under the assumption of perfect scalability) can be generated by additionally altering the features, e.g., geometry, of the coils to counteract the imperfection in the scalability. As one example, ferromagnetic (e.g., iron) rods (magnetic shims) can be inserted or removed from one or both of the magnetic structures (e.g., yokes, pole pieces, and the like). The features of the coils can be altered at a relatively high rate so that the rate of the magnetic field adjustment is not substantially affected as compared to the situation in which the scalability is perfect and only the electrical current needs to be adjusted. In the example of iron rods, the rods can be added or removed at the time scale of seconds or minutes, e.g., within 5 minutes, within 1 minute, less than 30 seconds, or less than 1 second.

In some implementations, settings of the accelerator, such as the current applied to the coil sets, can be chosen based on the substantial scalability of the magnetic field to the total electrical current in the coil sets.

Generally, to produce the total current that varies within a desired range, any appropriate combination of current applied to the two coil sets can be used. In an example, the coil set 42a, 42b can be configured to receive a fixed electrical current corresponding to a lower boundary of a desired range of the magnetic field. In the example shown in table 1, the fixed electrical current is 1760 Amperes. In addition, the coil set 40a, 40b can be configured to receive a variable electrical current having an upper boundary corresponding to a difference between an upper boundary and a lower boundary of the desired range of the magnetic field. In the example shown in table 1, the coil set 40a, 40b is configured to receive electrical current that varies between 0 Ampere and 230 Amperes.

In another example, the coil set 42a, 42b can be configured to receive a fixed electrical current corresponding to an upper boundary of a desired range of the magnetic field. In the example shown in table 1, the fixed current is 1990 Amperes. In addition, the coil set 40a, 40b can be configured to receive a variable electrical current having an upper boundary corresponding to a difference between a lower boundary and an upper boundary of the desired range of the magnetic field. In the example shown in table 1, the coil set 40a, 40b is configured to receive electrical current that varies between −230 Ampere and 0 Ampere.

The total variable magnetic field generated by the variable total current for accelerating the particles can have a maximum magnitude greater than 4 Tesla, e.g., greater than 5 Tesla, greater than 6 Tesla, greater than 7 Tesla, greater than 8 Tesla, greater than 9 Tesla, or greater than 10 Tesla, and up to about 20 Tesla or higher, e.g., up to about 18 Tesla, up to about 15 Tesla, or up to about 12 Tesla. In some implementations, variation of the total current in the coil sets can vary the magnetic field by about 0.2 Tesla to about 4.2 Tesla or more, e.g., about 0.2 Tesla to about 1.4 Tesla or about 0.6 Tesla to about 4.2 Tesla. In some situations, the amount of variation of the magnetic field can be proportional to the maximum magnitude.

Figure 32:
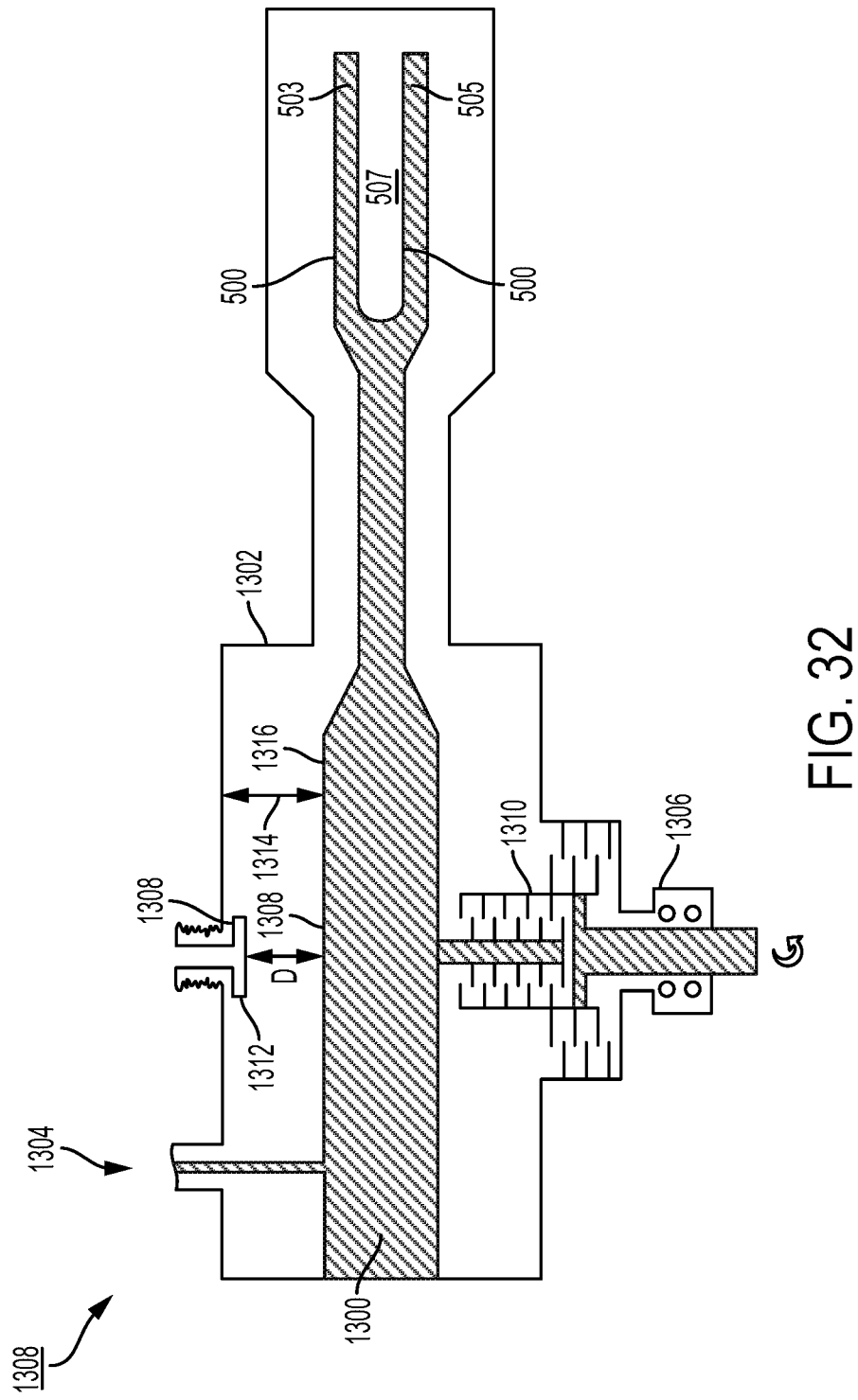
FIG. 32 is a side view of an example structure for sweeping voltage on a dee plate over a frequency range for each energy level of a particle beam, and for varying the frequency range when the particle beam energy is varied.

FIG. 32 shows an example RF structure for sweeping the voltage on the dee plate 500 over an RF frequency range for each energy level of the particle beam, and for varying the frequency range when the particle beam energy is varied. The semicircular surfaces 503, 505 of the dee plate 500 are connected to an inner conductor 1300 and housed in an outer conductor 1302. The high voltage is applied to the dee plate 500 from a power source (not shown, e.g., an oscillating voltage input) through a power coupling device 1304 that couples the power source to the inner conductor. In some implementations, the coupling device 1304 is positioned on the inner conductor 1300 to provide power transfer from the power source to the dee plate 500. In addition, the dee plate 500 is coupled to variable reactive elements 1306, 1308 to perform the RF frequency sweep for each particle energy level, and to change the RF frequency range for different particle energy levels.

The variable reactive element 1306 can be a rotating capacitor that has multiple blades 1310 rotatable by a motor (not shown). By meshing or unmeshing the blades 1310 during each cycle of RF sweeping, the capacitance of the RF structure changes, which in turn changes the resonant frequency of the RF structure. In some implementations, during each quarter cycle of the motor, the blades 1310 mesh with the each other. The capacitance of the RF structure increases and the resonant frequency decreases. The process reverses as the blades 1310 unmesh. As a result, the power required to generate the high voltage applied to the dee plate 103 and necessary to accelerate the beam can be reduced by a large factor. In some implementations, the shape of the blades 1310 is machined to form the required dependence of resonant frequency on time.

The RF frequency generation is synchronized with the blade rotation by sensing the phase of the RF voltage in the resonator, keeping the alternating voltage on the dee plates close to the resonant frequency of the RF cavity. (The dummy dee is grounded and is not shown in FIG. 32).

The variable reactive element 1308 can be a capacitor formed by a plate 1312 and a surface 1316 of the inner conductor 1300. The plate 1312 is movable along a direction 1314 towards or away from the surface 1316. The capacitance of the capacitor changes as the distance D between the plate 1312 and the surface 1316 changes. For each frequency range to be swept for one particle energy, the distance D is at a set value, and to change the frequency range, the plate 1312 is moved corresponding to the change in the energy of the output beam.

In some implementations, the inner and outer conductors 1300, 1302 are formed of a metallic material, such as copper, aluminum, or silver. The blades 1310 and the plate 1312 can also be formed of the same or different metallic materials as the conductors 1300, 1302. The coupling device 1304 can be an electrical conductor. The variable reactive elements 1306, 1308 can have other forms and can couple to the dee plate in other ways to perform the RF frequency sweep and the frequency range alteration. In some implementations, a single variable reactive element can be configured to perform the functions of both the variable reactive elements 1306, 1308. In other implementations, more than two variable reactive elements can be used.

Figure 34:
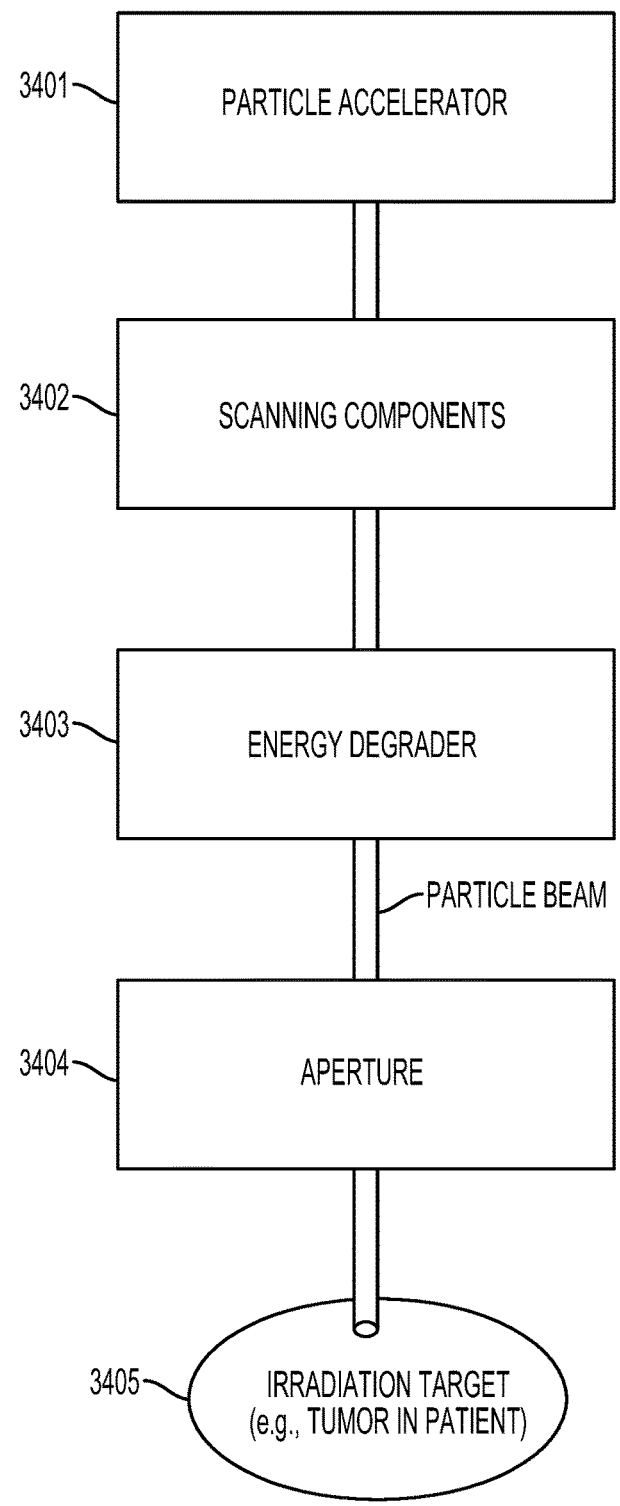
FIG. 34 is a block diagram showing an example particle therapy system that includes a switching energy degrader.

Referring back to FIG. 3 and also to FIG. 34, at the output of extraction channel of a particle accelerator 3401 (which may have configuration shown in FIGS. 1, 2) is a scanner comprised of scanning components 3402, such as a scanning magnet. As described with respect to FIG. 3, in an example operation, the scanning magnet is controllable in one or more (e.g., at least two) dimensions (e.g., Cartesian XY dimensions) to direct the particle beam across a part (e.g., a cross-section) of an irradiation target. An ion chamber detects the dosage of the beam and feeds-back that information to a control system to adjust beam movement. An energy degrader is controllable to move one or more elements—e.g., plates—into, and out of, the path of the particle beam to change the energy of the particle beam and therefore the depth (the Z direction) to which the particle beam will penetrate the irradiation target. For example, the energy degrader may include one or more computer-controlled motors, that drive a plate or multiple plates in sequence into the beam field, and retract the plate or plates from the beam field. In some implementations, the beam field corresponds the maximum lateral extent that the particle beam may move in specified directions, e.g., in a Cartesian XY plane above an irradiation target as shown, for example, in FIG. 19.

As described herein, scanning of the particle beam does not wait for plates to be moved into place, but rather scanning of the particle beam may be performed during plate movement. Although scanning may be performed during plate movement, scanning may also be performed when plates are stationary or not present. For example, in some cases, to reach a deepest layer of a target, no plate need be moved into the path of the particle beam. And, in some cases, all plates may be positioned and stationary while scanning takes place. In some implementations, the energy degrader may have a configuration and operation as described with respect to FIGS. 36 to 49, which are described below Referring to FIG. 34, an energy degrader 3403, which may have the configuration and operation of FIGS. 36 to 49, is located between particle accelerator 3401 and irradiation target 3405 (e.g., a tumor in the patient). For example, energy degrader 3403 may be located on a nozzle 610 of inner gantry 601 (FIG. 29), and may be controlled by a computer system that also controls operation of other components of the particle therapy system. Operation of energy degrader 3403 may be coordinated with, and controlled with, operation of the scanning components, the particle accelerator, and the inner and outer gantries described herein to implement the particle therapy treatment described herein, and variations thereof.

In some implementations, beam passage through the energy degrader may result in further beam divergence. Accordingly, an aperture 3404 may be positioned between the energy degrader and the irradiation target. The aperture may be controllable to further shape the beam, as described herein.

In an example, each plate of the energy degrader located in the particle beam path absorbs an amount of energy in the particle beam. Accordingly, the more plates that are placed in the path of the particle beam, the less energy the beam has, and the less deep the beam will penetrate into the irradiation target. Conversely, the fewer plates that are placed in front of the particle beam, the more energy the beam has (since less energy is absorbed by the plate(s)), and the more deep the beam will penetrate into the irradiation target. Thus, for a given plate of the energy degrader, the energy of the particle beam incident on that plate exceeds the energy of the particle beam following passage through the plate. In some implementations, the plates may be made of one or more of the following example materials: polycarbonate, carbon, beryllium, or other material having a low atomic number. Other materials, however, may be used in place of, or in addition to, these example materials. As described herein, a treatment plan may dictate the configuration of the energy degrader at any particular time during treatment, and feedback from the ionization chamber may be used for positioning and position correction of the particle beam.

Figure 49:
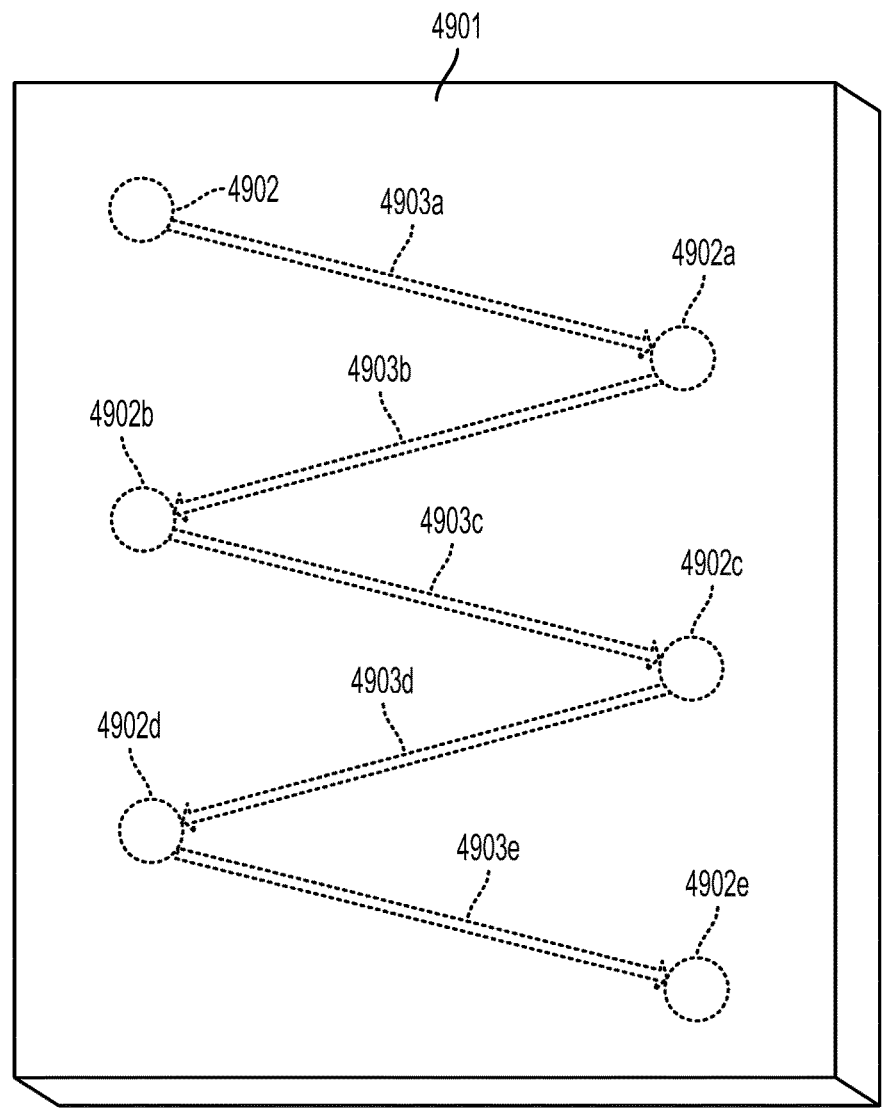
FIG. 49 is a top perspective view of a plate illustrating two-dimensional scanning of the plate.

The energy degrader may be a high-speed energy-switching range shifter. In an example, an energy degrader of this type includes one or more elements, e.g., one or more plates, that move during movement of the particle beam during scanning. For example, the plates(s) may move from a starting position towards an ending position and, while the plate(s) move, the particle beam is moved in one or more dimensions across the surface of the plate(s). For example, the particle beam may be moved in one dimension, in two dimensions, or in three dimensions across the surface of the plate(s) and, ultimately, across the irradiation target. For example, FIG. 49 shows a top perspective view example plate 4901. Spot 4902 of particle beam is scanned in an example two-dimensional path labeled 4903a, 4903b, 4903c, 4903d, and 4903e. Example future positions of spot 4902 during scanning are labeled 4902a, 4902b, 4902c, 4902d, and 4902e, although it is noted that spot will appear at all locations along the two-dimensional path.

The speed of the beam's movement in the movement direction may be the same as, slower than, or faster than, the speed of movement of the plate(s) in the movement direction (so long as the beam remains on a plate surface). In some implementations, if the beam moves faster than a plate, then the beam may stop to wait for the plate. As described herein, concurrent movement of plates and the particle beam can decrease the treatment time relative to some known energy degraders.

Figure 36:
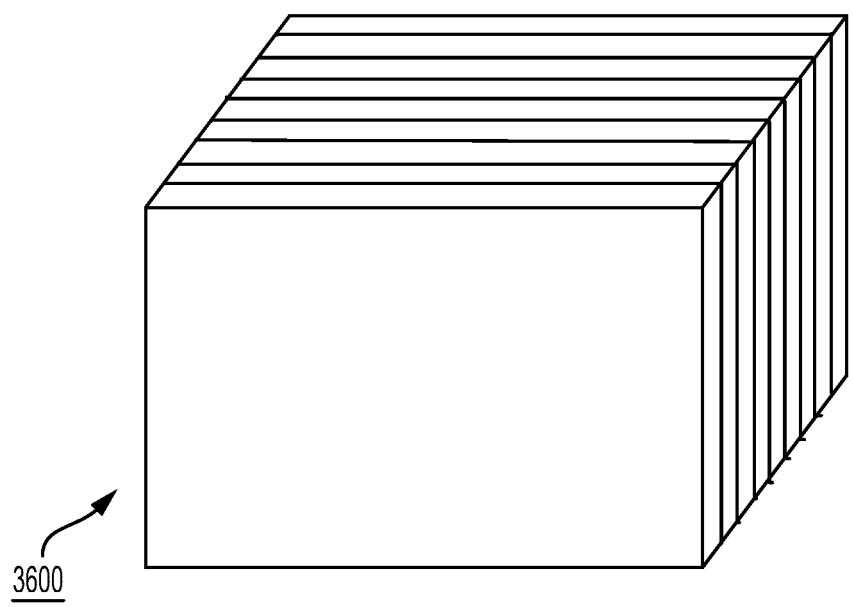
FIG. 36 is perspective view of example plates of a switching energy degrader that have the same thickness.

In some implementations, each of the plates has a uniform thickness, as shown in FIG. 36. That is, in such implementations, there is little or no thickness variation across each plate. In some implementations, the plates of the energy degrader may each have the same thickness, defined as a "step size". In this context, a step size refers to the distance between two layers of a target to be treated. That is, the thickness may correspond, e.g., to the beam energy required to hit individual layers of the irradiation target. In some implementations, no plate is used to reach the deepest layer of an irradiation target. For example, the energy degrader may be configured so that no plates are in the path of the particle beam, and so that the particle beam simply passes, without energy change, to the irradiation target. Then, plates are added to reach other, shallower layers. That is, to reach more shallow layers of the irradiation target, plates are moved into the beam field/treatment area and into the path of the particle beam.

Figure 35:
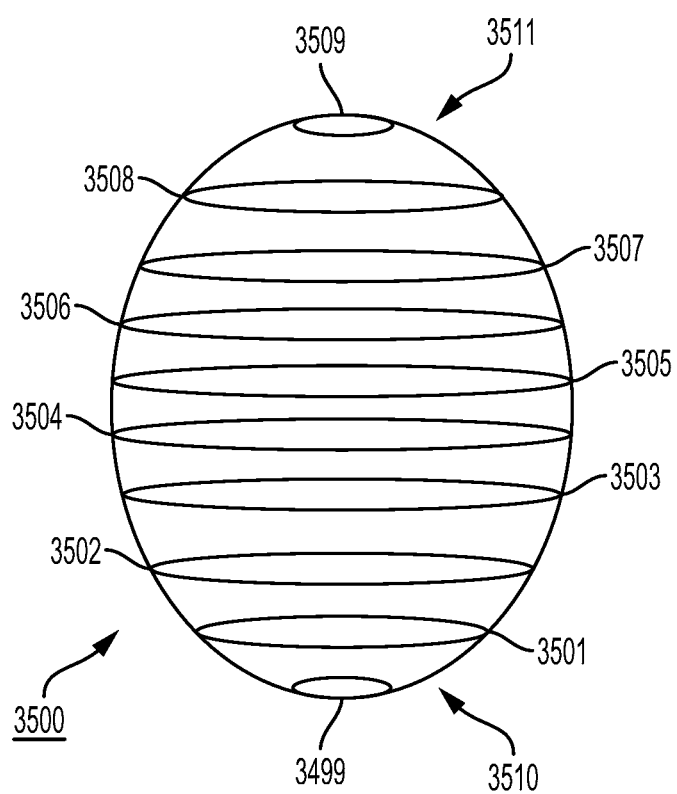
FIG. 35 is a perspective view of an example irradiation target, including layers thereof to be treated by particle therapy.

By way of example, referring to FIG. 35, an example irradiation target 3500 may be divided into ten layers 3499, 3501, 3502, 3503, 3504, 3505, 3506, 3507, 3508, and 3509 (also referred to as steps), each of which is to be treated by scanning the particle beam across that layer. Layer 3499 is at the deep end 3510 of the target and requires the most energy to hit, whereas layer 3509 is at the shallow end 3511 of the target and requires the least energy to hit. Accordingly, in this example implementation, no plates are moved into the path of the particle beam to hit layer 3499. That is, the particle beam passes, without energy change, through the energy degrader. Thereafter, in an example operation, using plates having a thickness that corresponds to a single step (e.g., an energy level of the layer), a single plate may be moved into the beam path to change the energy of the beam so that the beam hits layer 3501, two plates may be moved into the beam path to change the energy of the beam so that the beam hits layer 3502, three plates may be moved into the beam path to change the energy of the beam so that the beam hits hit layer 3503, and so forth until all layers are treated. As described herein, the particle beam moves across the plate(s) (and thus, ultimately, across the corresponding layers) as the plate(s) move across the beam field, thereby treating the irradiation target during time that was heretofore not used for treatment.

Figure 37:
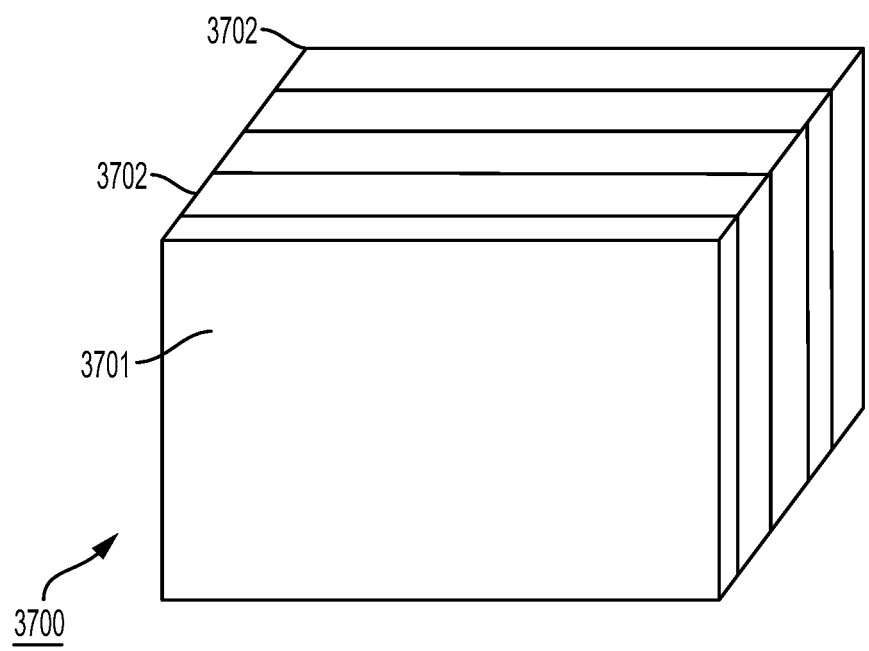
FIG. 37 is perspective view of example plates of a switching energy degrader that have different thicknesses.

In some implementations, different plates within the energy degrader may have different thicknesses. For example, in some implementations, the energy degrader may contain a first plate having a first thickness and multiple additional plates each having a second thickness that is different than the first thickness, as shown in FIG. 37. In an example, the first plate may have a thickness that corresponds to the beam energy required to hit an individual layer of the irradiation target (e.g., a single step size). The additional plates may each be thicker than the first plate. For example, each additional plate may have a thickness that is two step sizes or twice as thick as the first plate to allow combinations of first and other plates to produce beam energies required to hit every layer within the irradiation target. Referring to FIG. 35, in an example implementation, target 3500 may be treated as follows using the first plate and the additional plates. To treat layer 3499, all plates may be moved out of the beam path. To treat layer 3501, the first plate may be moved into the beam path. To treat layer 3502, the first plate may be retracted from the beam path and an additional plate (having twice the thickness of the first plate) may be moved into the beam path. To treat layer 3503, both the first plate having a single step thickness and an additional plate having the two-step thickness may be moved into the beam path. To treat layer 3504, the first plate may be removed from the beam path and two additional plates, each having a two-step thickness, may be placed into the beam path. This process, which includes introducing zero, one, or more second plates and the first plate for odd-numbered layers, excluding the deepest layer 3499 (e.g., layers 3501, 3503, 3505, 3507, and 3509 in this example) and retracting the first plate for even-numbered layers (e.g., layers 3502, 3504, 3506, and 3508 in this example), may be performed until all layers of the target have been treated. As described herein, the particle beam moves across the plate(s) (and, ultimately, across corresponding layers of the irradiation target) as the plate(s) move across the beam field, thereby treating the irradiation target during time that was heretofore not used for treatment.

In some implementations, the individual plates may have different thicknesses than those described herein. For example, the plates may have more than two different thicknesses, and may be sequenced appropriately to hit all layers of a radiation target. For example, the energy degrader may contain a first plate having a single step size, and additional plates that are thicker than the first plate. For example, some additional plates may be two step sizes thick, while others are three step sizes thick, four step sizes thick, eight step sizes thick, and so forth. Referring, for example, to FIG. 35, target 3500 may be treated as follows using the first plate and the additional plates. To treat layer 3499, all plates may be moved out of the beam path. To treat layer 3501, the first plate may be moved into the beam path. To treat layer 3502, the first plate may be removed from the beam path and a second additional plate (having twice the thickness of the first plate) may be moved into the beam path. To treat layer 3503, the first plate and the second plate may be removed from the beam path and a third additional plate (having three times the thickness of the first plate) may be moved into the beam path. To treat layer 3504, the third additional plate (having a three-step thickness) may be left in the beam path and the first plate (having a one-step thickness) may be moved into the beam path. To treat layer 3505, the third additional plate may be left in the beam path, the first plate may be removed from the beam path, and the second additional plate (having a two-step thickness) may be moved into the beam path. This process, which includes moving different plates into the beam path different times based on the energy level desired, may be performed until all layers of the target have been treated. As described herein, the particle beam moves across the plate(s) as the plate(s) move across the beam field, thereby treating the irradiation target during time that was heretofore not used for treatment.

In some implementations, the layers may, but need not, be treated in depth-wise order. In this regard, referring to FIG. 35, the plates of the energy degrader may be sequenced so that layer 3499 is treated first, followed by layer 3501, followed by layer 3502, followed by layer 3503, and so forth until all layers are treated in order, or so that layer 3509 is treated first, followed by layer 3508, followed by layer 3507, and so forth until all layers are treated in order. In some implementations, however, the plates of the energy degrader may be sequenced so that the layers are not treated in depth-wise order, e.g., so that layer 3503 is treated first, followed by layer 3508, followed by layer 3501, and then followed by other layers until all layers are treated. The order in which layers are treated may be determined by a treatment plan, which may be based, at least in part, on the configuration of the energy degrader.

In some implementations, the use of fewer plates may reduce the number of moving parts in the energy degrader, thereby making the energy degrader less prone to mechanical malfunction. Fewer plates may also reduce the size of the energy degrader allowing the energy degrader to be located relatively close to a patient undergoing treatment. Movement of plates into, or out of, the beam path can noisy. Use of plates having different thicknesses may reduce the number of plates that need to be moved into the beam path, which may reduce noise during treatment in some cases.

FIG. 36 shows an example energy degrader 3600 having multiple plates, each of which corresponds to a single step.

FIG. 37 shows an example energy degrader 3700 also having multiple plates, with one plate 3701 corresponding to a single step and with the multiple other plates 3702 each corresponding to two steps (in other words, in this example, plate 3701 is half the thickness of each of plates 3702). Energy degrader 3700 may require movement of fewer plates than energy degrader 3600 in order to hit all layers of a target and, therefore, may be less noisy, smaller, and less susceptible to mechanical malfunction in some cases. In some implementations, energy degrader 3700 may include multiple single-step plates like plate 3701, and multiple thicker plates like plates 3702. In some implementations, energy degrader 3700 may include a single thicker plate like plate 3702, and multiple single-step plates like plate 3701.

In the example energy degraders described herein, individual plates are movable into, and out of, the path of the particle beam, and may continue their movement as the particle beam is moved during scanning. More specifically, in some known energy degraders, plates are positioned prior to scanning of the particle beam. After positioning, scanning is performed, and then halted as the plates are repositioned. Treatment time may be prolonged in systems such as these. By moving the particle beam during movement of its plates, as described herein, the example energy degrader may reduce treatment time relative to the treatment time resulting from use of known systems. This is because both the particle beam and the plates move at the same time. Thus, time that was previously used to move plates prior to patient treatment can be used for actual treatment.

In some implementations, the same computer system that controls the energy degrader also controls movement of the particle beam during scanning. In some implementations, different computer systems control operations of the energy degrader and movement of the particle beam. In either case, operations of the energy degrader and/or the scanner may be coordinated so that the particle beam passes through an appropriate number of plate(s) for the treatment layer desired while those plate(s) are in motion across at least part of the beam field. In some implementations, operation of the energy degrader also includes passing the particle beam through plates whose motion has stopped, as also described herein.

Figure 38:
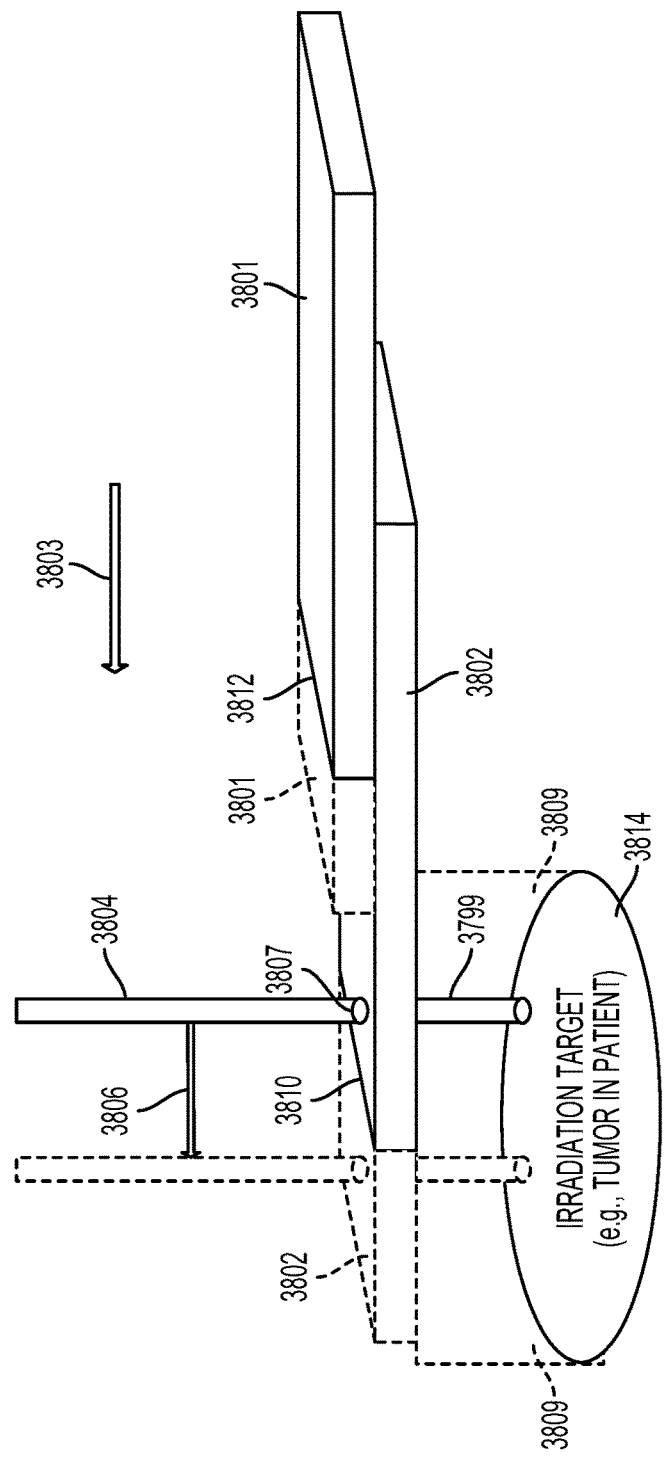
FIG. 38 is a perspective view showing plates of an example energy degrader moving separately during scanning in a forward direction.

Referring to FIG. 38, in an example operation, plates 3801, 3802 of an energy degrader are controllable to move in a same direction (in this example, the direction of arrow 3803), and at the same time, during movement of particle beam 3804 during scanning. In the example of FIG. 38, movement of particle beam 3804 during movement of the plates is represented by arrow 3806. In the example of FIG. 38 and the other figures presented subsequently, the particle beam at a future location, following movement, is represented in dashed lines. In the example of FIG. 38 and the other figures presented subsequently, a plate of the energy degrader at a future location, following movement, is represented in dashed lines. Only a portion of the plate at the future location may be represented (as is the case in FIG. 38), since current and future locations of the plate may overlap and the current plate location is represented in solid lines.

In an example operation, the particle beam 3804 passes through one or more of the plates (e.g., at least part) of the energy degrader while corresponding plates are in motion. For example, FIG. 38 shows first plate 3801 and second plate 3802, both of which are part of an example energy degrader. First plate 3801 and second plate 3802 are controllable to move in the direction of arrow 3803. In this example, the particle beam is orthogonal to the plates, although that need not be the case in some implementations. For example, the particle beam may be non-orthogonal to the plates as is the case with intensity-modulated proton therapy described with respect to FIG. 18. The particle beam is represented by a spot 3807 on a plate (here, plate 3802) on which the particle beam is incident.

In an example operation, plate 3802 begins moving towards/into the beam field 3809 in the direction of arrow 3803. Scanning may begin at any appropriate time after plate 3802 is within the beam field. When scanning begins will be determined by a treatment plan, which identifies the location of a radiation target relative to the plates of the energy degrader. As described herein, scanning may begin within the beam field prior to any plates being in the beam field. For example, in some implementations, to scan a deepest layer in a target, no beam energy change is required and, therefore, no plates are in the path of the beam. However, the plates may begin moving towards, and into, the beam field at any appropriate time before or after scanning begins, including as the deepest layer is being scanned, plates may be moved into the beam field but trail the beam path.

Figure 39:
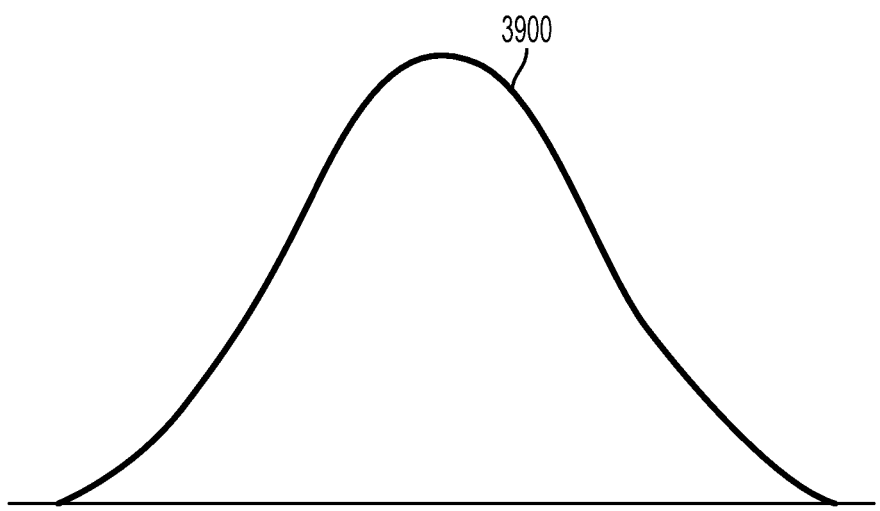
FIG. 39 is a graph showing the Gaussian distribution of a particle beam spot.

In some implementations, movement of the particle beam across plate 3802 is limited to movement outside of a predefined distance from an edge 3810 of plate 3802. For example, the energy degrader and/or the scanning system may be controlled so that the particle beam does not pass near to edge 3810. This is because, as shown in FIG. 39, a spot incident on plate 3802 has a Gaussian distribution 3900 of particles. Accordingly, applying the spot near to (e.g., within a distance of) an edge 3810 of plate 3802 may cause some particles to pass, unimpeded, to the patient unintentionally. Accordingly, operation of the scanning system and/or energy degrader may be controlled so that spots are applied away from a least one, and in some cases all, edges of plates. In some implementations, the minimum distance between the spot and the edge of a plate is in the range of $2\sigma$ to $2.5\sigma$, where $\sigma$ is one standard deviation of the Gaussian curve representing the distribution of particles in a spot. However, the implementations described herein are not limited to distances in the range of $2\sigma$ to $2.5\sigma$.

Referring back to FIG. 38, particle beam movement across plate 3802 produces a reduced-energy particle beam 3799 that is applied to the irradiation target 3814. That is, the particle beam passes through plate 3802, thereby changing (e.g., reducing) the energy of the particle beam to enable the particle beam to hit a corresponding energy layer (step) of the irradiation target. In this example, at some point in time after motion of plate 3802 begins, and while plate 3802 is in motion and movement of the particle beam continues, plate 3801 also starts to move, in this example, in the direction of arrow 3803. During its motion, plate 3801 partly overlaps and trails plate 3802, and both plates continue to move concurrently for at least some period of time. In some implementations, edge 3810 of plate 3802 may move least a $2\sigma$ to $2.5\sigma$ distance relative to the edge 3812 of plate 3801 before plate 3801 starts moving; however, in other implementations, different criteria may be used. In some implementations, there is not a trailing plate. For example, in FIG. 38, plate 3801 may not begin moving until plate 3802 has reached its ending position or until plate 3802 has been moved to its ending position and then retracted to its starting position (e.g., plate 3801 may not trail plate 3802).

Figure 38A:
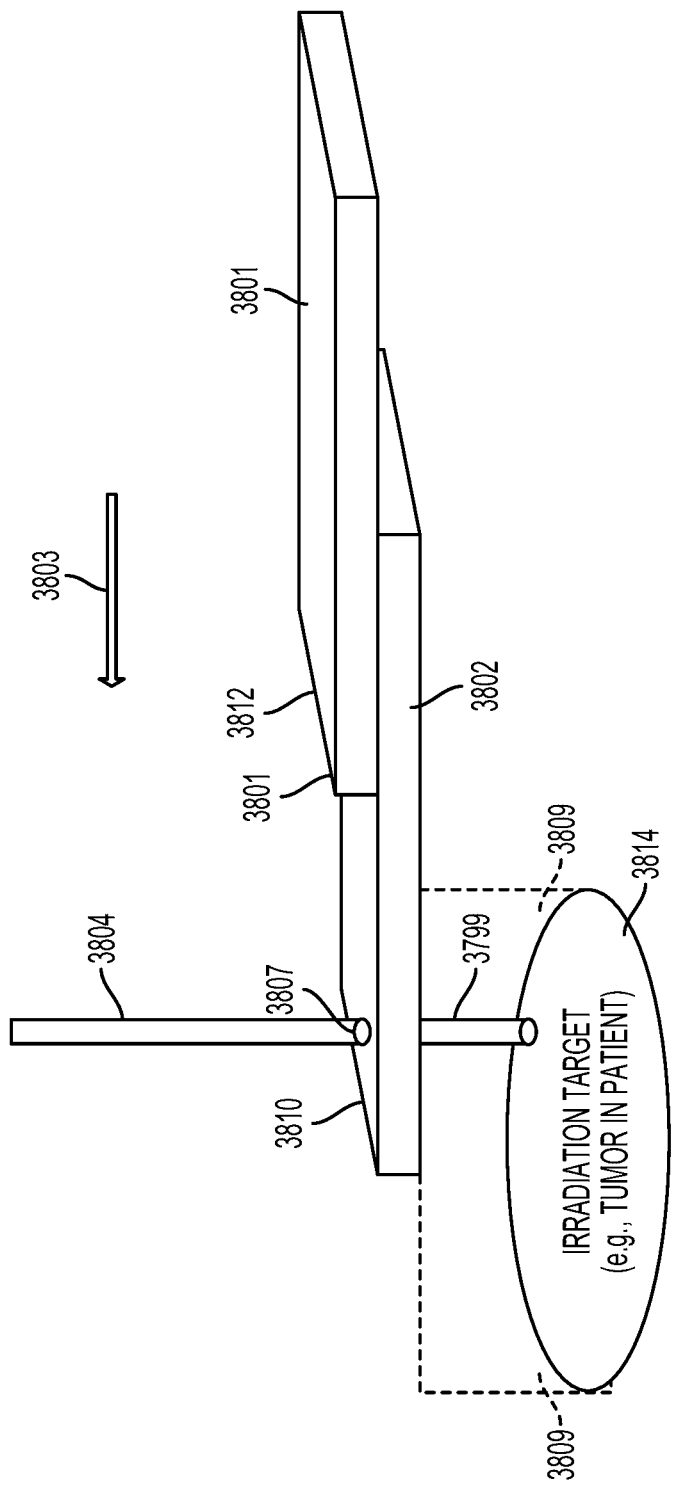
FIG. 38A is a perspective view showing plates of an example energy degrader at a first position during scanning in a forward direction.
Figure 38B:
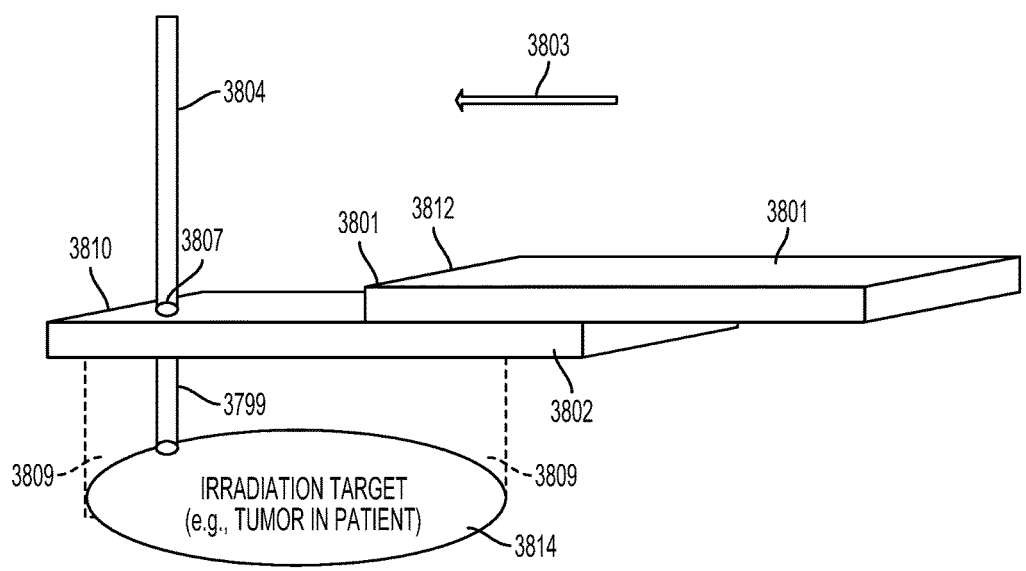
FIG. 38B is a perspective view showing plates of an example energy degrader at a second position during scanning in a forward direction.

FIGS. 38A and 38B depict the plates of FIG. 38 without dashed lines at different points during the scanning of irradiation target 3814.

At some time, particle beam movement across plate 3802 will be completed—for example, the entire layer corresponding to the step of plate 3802 may be scanned. Thereafter, scanning for the next layer of the irradiation target may begin. In this context, "next" does not necessarily mean a next layer in depth sequence as shown in FIG. 35, but rather a next layer to be scanned according to a treatment plan. As explained above, that next layer need not be a layer that is in depth-wise sequence relative to the previously-scanned layer. The next layer may be reached, in this example, by moving the particle beam across, and through, both plates 3801 and 3802. Because plate 3801 has already begun moving, plate 3801 may be in place, or closer in place than would otherwise be the case had plate 3801 not begun movement, to begin scanning operations for the next layer.

Figure 40:
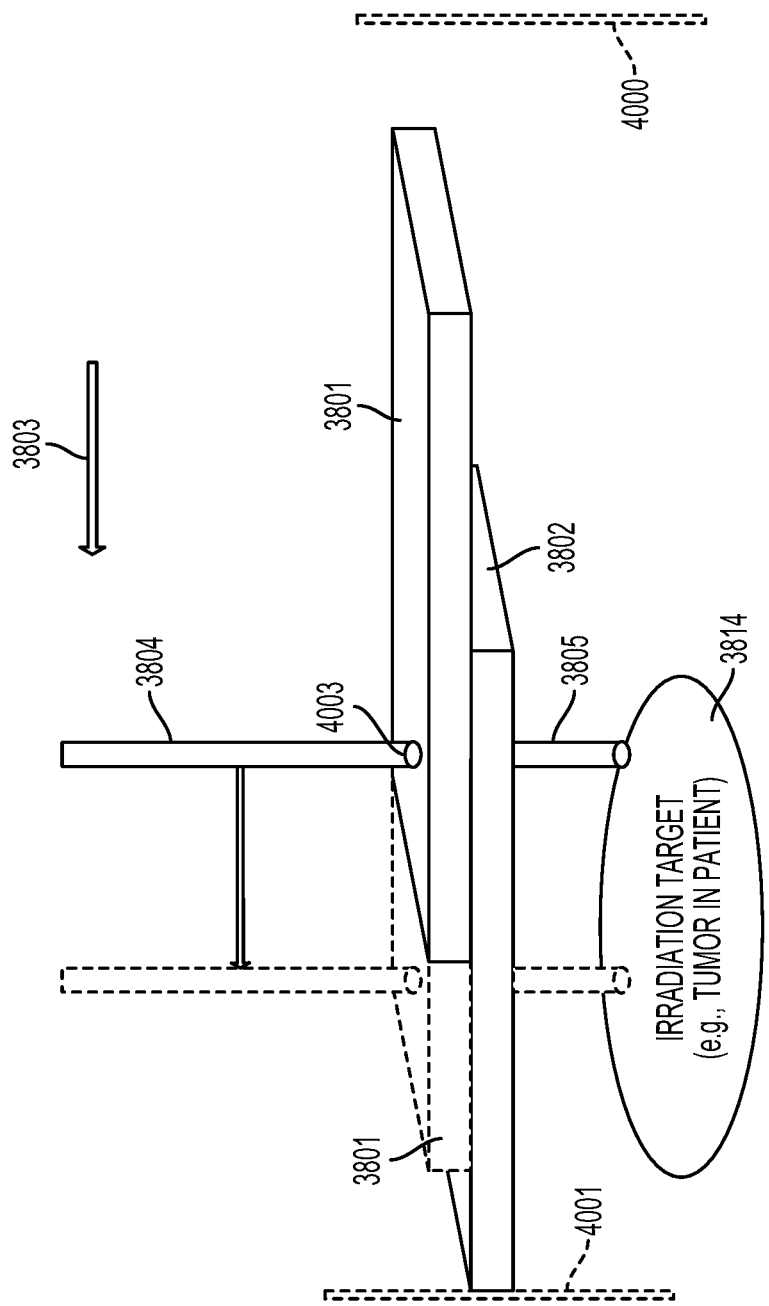
FIG. 40 is a perspective view showing plates of an example energy degrader moving separately during scanning in a forward direction.
Figure 41:
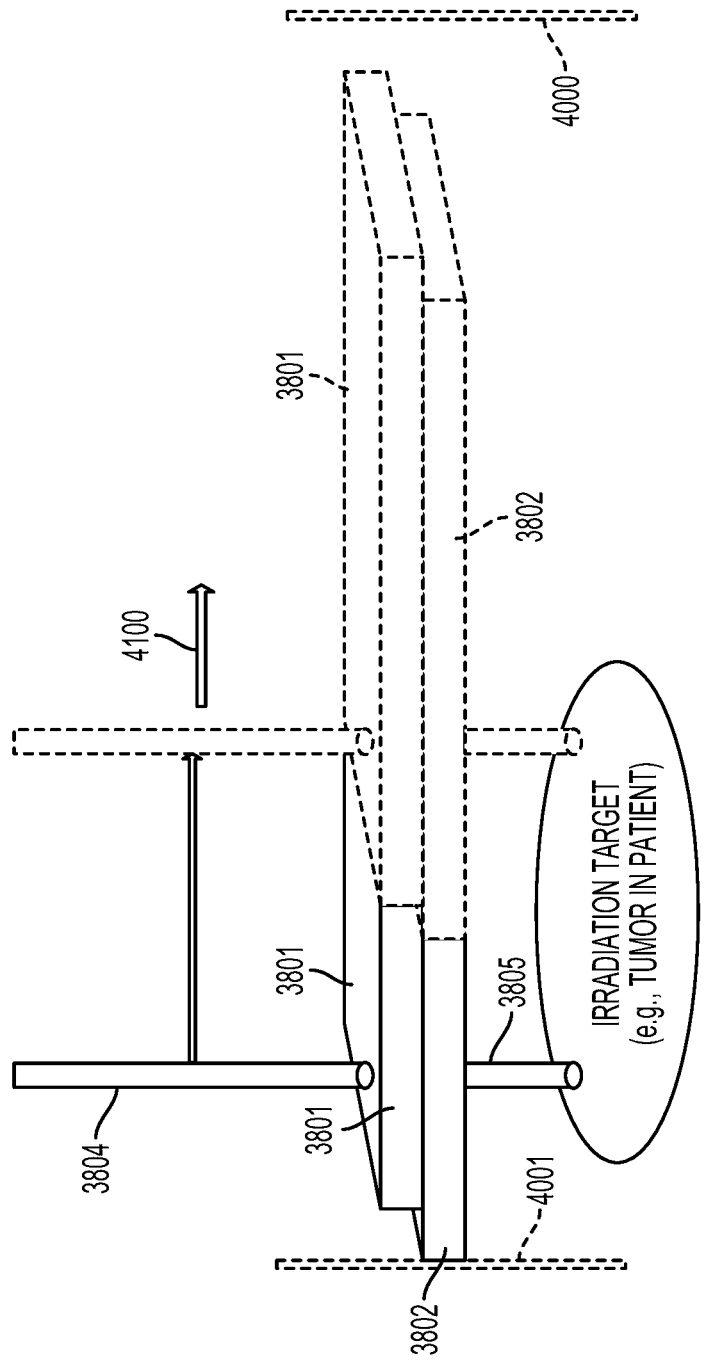
FIG. 41 is a perspective view showing plates of an example energy degrader moving together during scanning in a reverse direction.
Figure 42:
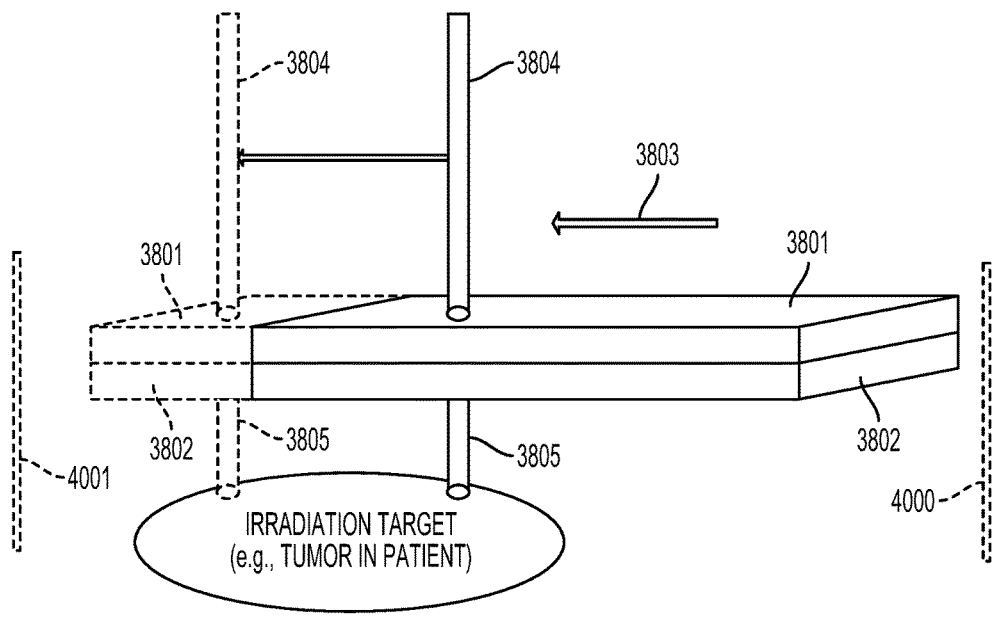
FIG. 42 is a perspective view showing plates of an example energy degrader moving together during scanning in a forward direction.

Referring to the examples of FIGS. 40 and 41, the particle beam may next be moved across combined plates 3801 and 3802 from a point towards the starting position (reverse direction) or from a point towards the ending position (forward direction). In this regard, in an example operation, each plate of the energy degrader moves from a starting position 4000 to an ending position 4001. In some implementations, the scanning system may begin scanning the particle beam through the combined plates at a point near to the starting position and proceed towards a point near to the ending position (with the respective points being determined based on the treatment plan). This is referred to as scanning in the forward direction. In some implementations, the scanning system may begin scanning the particle beam at a point near to the ending position and proceed towards a point near to the starting position (again, with the respective points being determined based on the treatment plan). This is referred to as scanning in the reverse direction. The scanning direction may be specified in the treatment plan, and may be based on any appropriate factors, such as the location of the plates, the state of the beam, and so forth.

By way of example, scanning may be performed in the forward direction (e.g., towards the ending position) and then in the reverse direction (e.g., towards the starting position) if the plates are appropriately positioned. However, in some cases, such as that shown in FIG. 40, after plate 3802 is scanned, e.g., the plate has reached the end position 4001, a trailing plate 3801 may not yet be in an appropriate position to scan through both plates in the reverse direction. In some cases, it may take more time to wait for the trailing plate 3801 to reach the appropriate position for reverse scanning than to reposition the beam near to the starting position to scan towards the ending position. Accordingly, in such cases, the particle beam is repositioned at an appropriate point 4003 towards the starting position 4000, and scanning through both plates proceeds in the forward direction of arrow 3803 while plate 3801 continues to move towards the end position 4001 (plate 3802 has stopped movement at this point). Again, because plate 3801 is already in place across the beam field, there is no need to wait for that plate to be appropriately positioned for scanning through both plates to begin. Furthermore, while scanning proceeds, plate 3801 continues to move towards the ending position 4001 in the direction of arrow 3803. Plate 3802 may be stationary at this point.

In some cases, as shown in FIG. 41, after plate 3802 is scanned, the trailing plate 3801 may be in an appropriate position, or such a position may be reachable in an appropriate time, to scan through both plates in the reverse direction (the direction of arrow 4100). Accordingly, in these cases, the scanning may proceed in the reverse direction and plate 3801 may reverse its movement direction. As the particle beam is scanned towards the starting position, one or both of plates 3801 and/or 3802 may be retracted, that is, moved toward the starting position so that a different configuration of plates can be moved into the beam field for a next scan. In the example shown in FIG. 41, both plates are retracted; however, that need not be the case.

Figure 43:
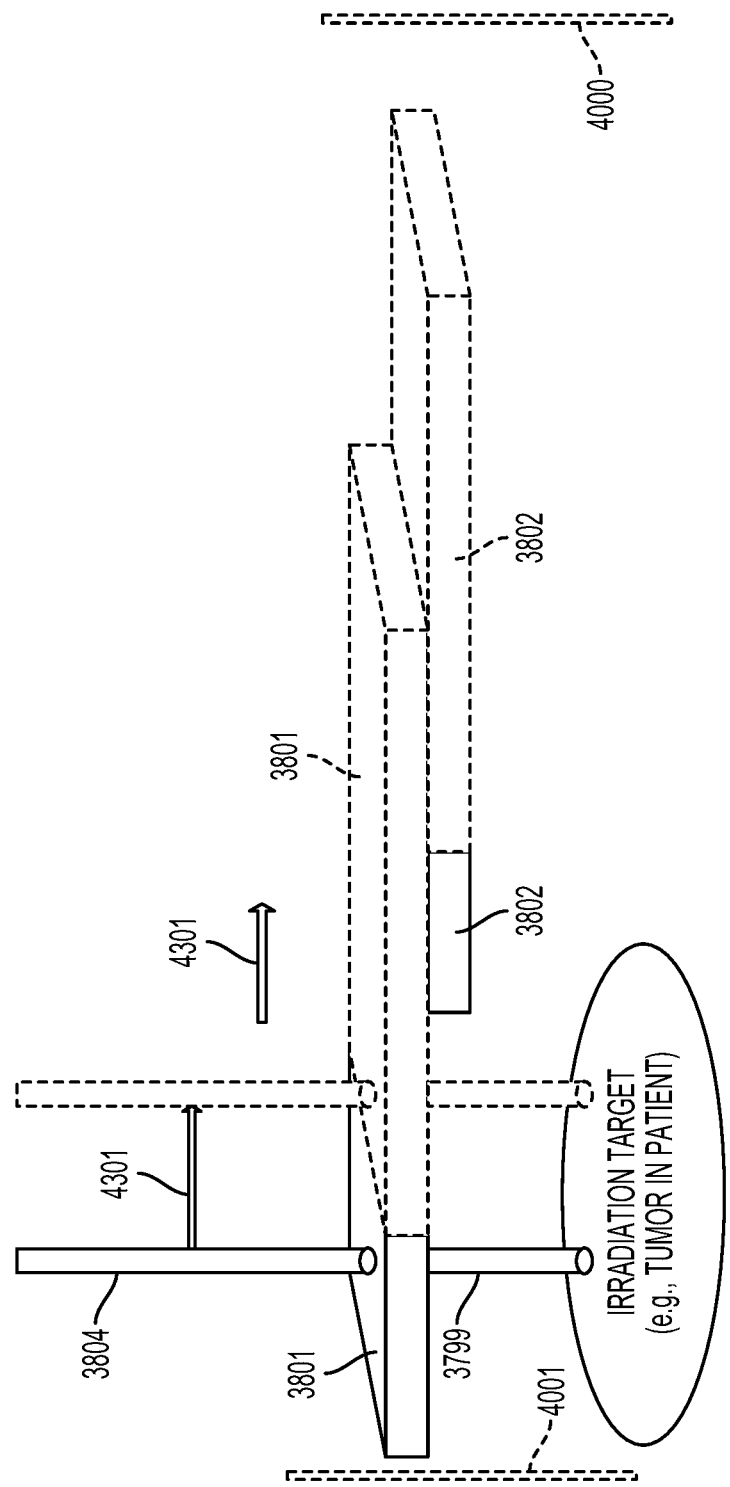
FIG. 43 is a perspective view showing plates of an example energy degrader moving separately during scanning in a reverse direction.
Figure 44:
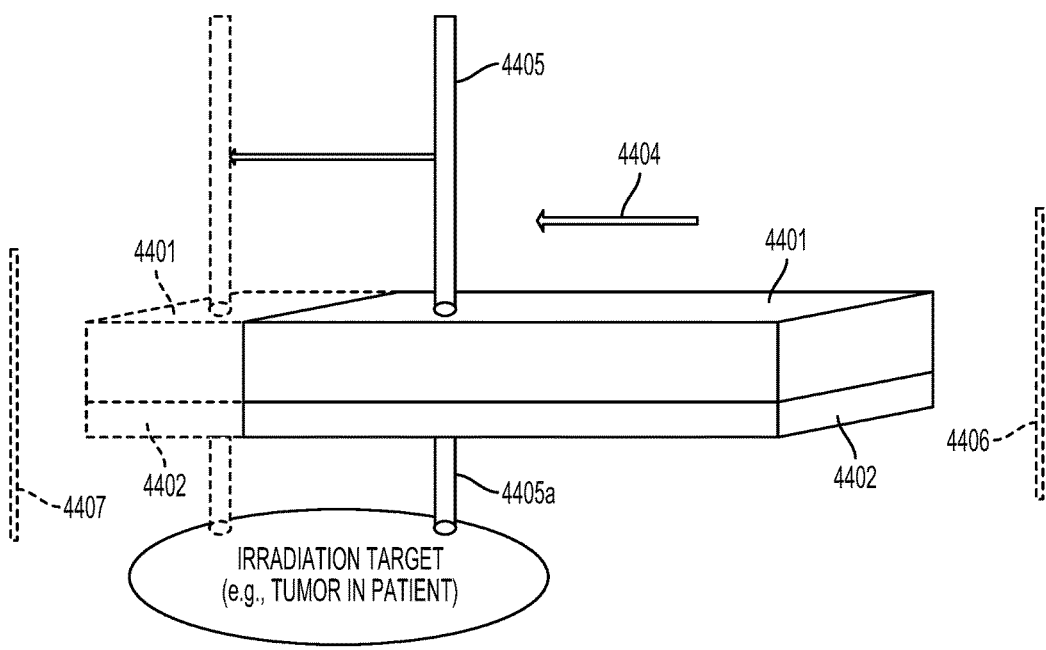
FIG. 44 is a perspective view showing plates of an example energy degrader moving together during scanning in a forward direction.

In the examples of FIGS. 40 and 41, a deeper layer in the target is scanned first by moving a single plate 3802 into the beam path and a more shallow layer is target is scanned next by moving another plate 3801 into the beam path so that the beam passes through both plates 3801 and 3802. In some implementations, two or more plates may first be moved into the beam path (thereby treating more shallow layer(s)), and subsequently plate(s) may be retracted during scanning. For example, referring to FIG. 42, in an example operation, two (or more) plates 3801, 3802 may begin motion concurrently from their starting position 4000 towards their ending position 4001 in the particle beam field. During movement of the plates, the particle beam may be moved across the plates in the forward direction (represented by arrow 3803), thereby causing the particle beam to pass through both plates 3801 and 3802 to produce a particle beam 3805 having an appropriate energy. Referring to FIG. 43, after the plates reach the ending position 4001, the particle beam may be scanned in the reverse direction (represented by arrow 4301) as a plate, such as plate 3802, is first retracted towards the staring position 4000. That is, plate 3802 is retracted first so that the particle beam moves across only plate 3801, as shown. Plate 3801 may also be retracted as the particle beam moves across plate 3801, as shown. The scanning components and energy degrader may be controlled so that the particle beam follows, but does not pass through, plate 3802 during its movement in the direction of arrow 4301, thereby causing the particle beam to pass through plate 3801 only to produce a particle beam 3799 having an appropriate energy.

Any appropriate number (e.g., one, two, or more) plates may be moved across the beam field while the particle beam is scanned across the irradiation target in either the forward or reverse direction, as described herein. The number and sequence of plates, and the scanning direction, may be specified in the treatment plan, as appropriate. In addition, as described herein, different plates may have different thicknesses. Plate thickness may affect how plates are moved.

Figure 45:
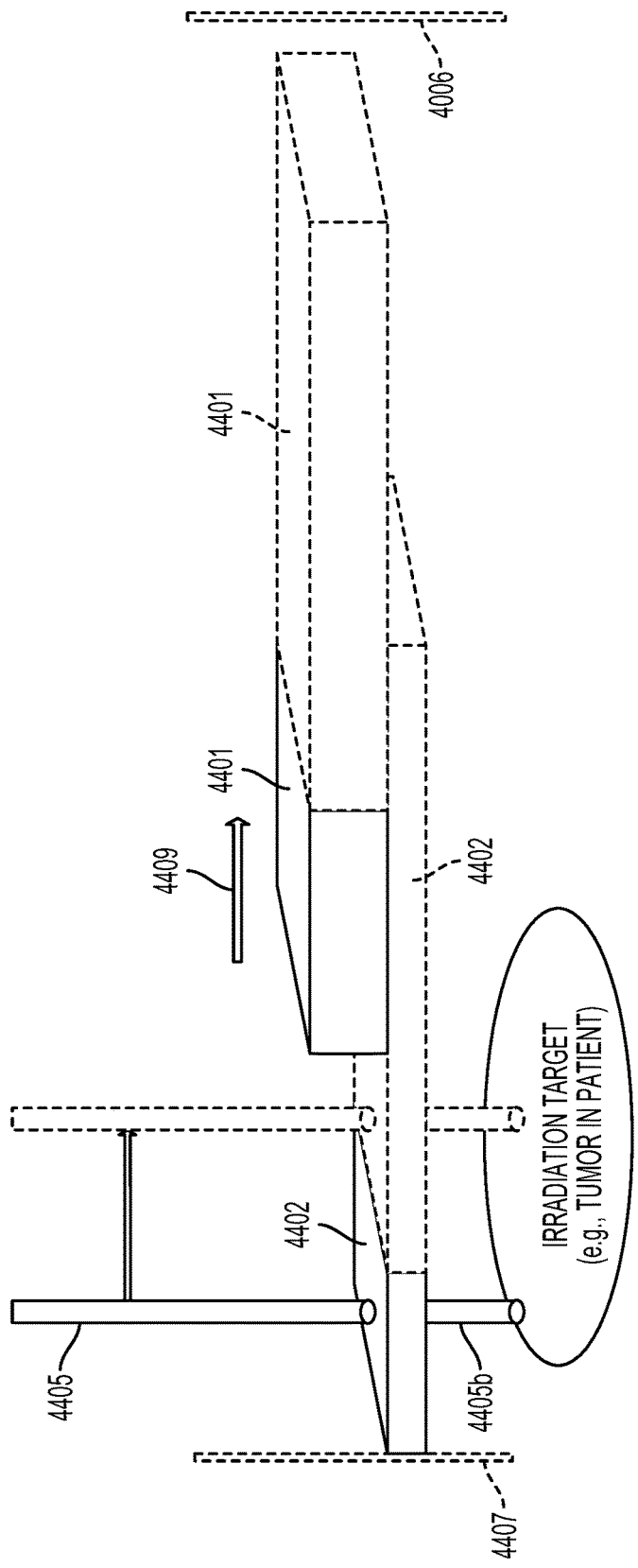
FIG. 45 is a perspective view showing plates of an example energy degrader moving separately during scanning in a reverse direction.
Figure 46:
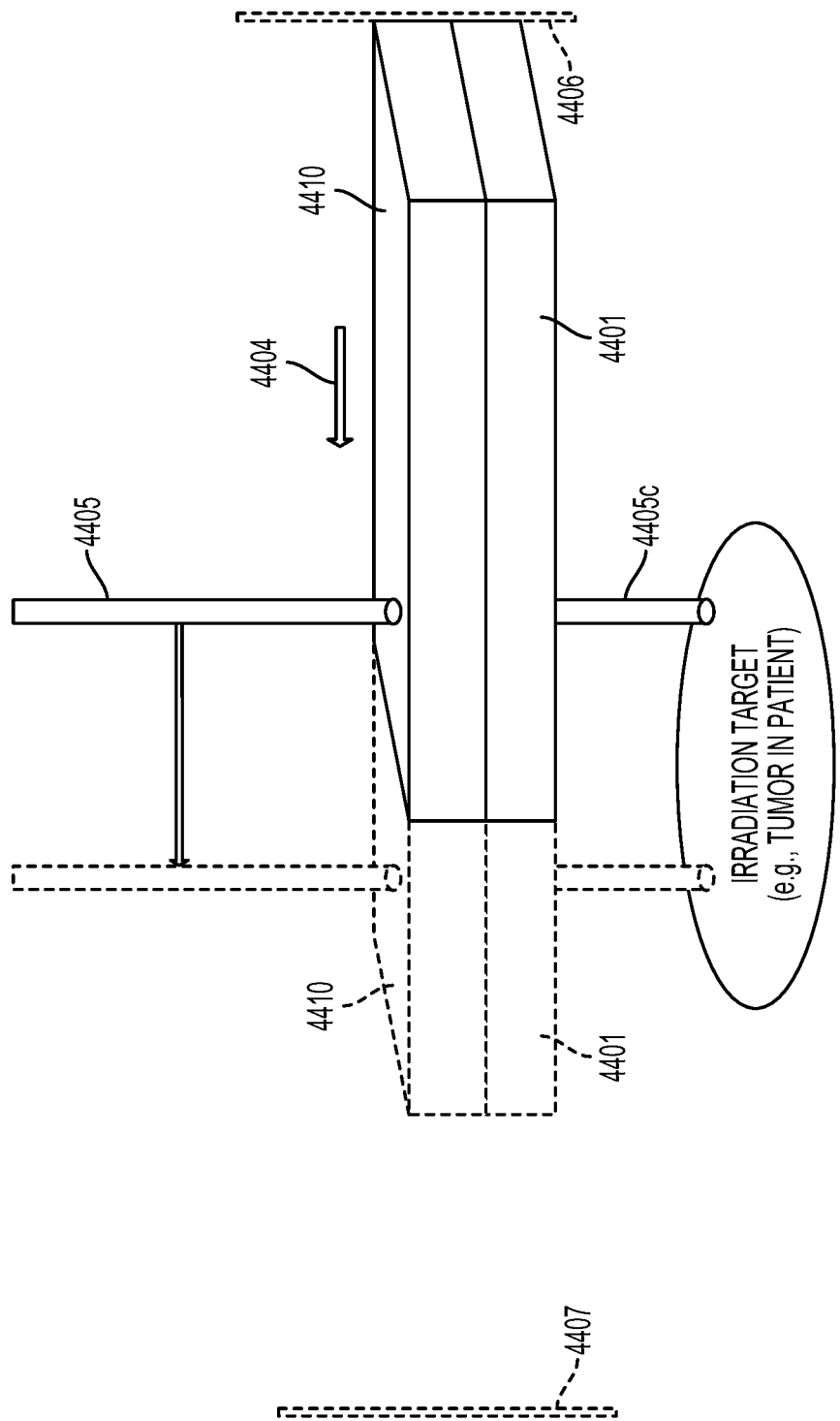
FIG. 46 is a perspective view showing plates of an example energy degrader moving together during scanning in a forward direction.

Movement of the plates may be sequenced so that the particle beam is not turned-off during treatment or so that the particle beam turn-off time has been reduced. For example, the speed of scanning the particle beam, the thicknesses of the plates, and movement of the plates may be selected so that reverse-direction scanning immediately or quickly follows forward direction scanning during treatment. For example, referring to FIGS. 44 to 46, an example energy degrader includes a single thickness ("1×") plate 4402 and a double thickness ("2×") plate 4401 that may be moved into the treatment field at the same time in forward direction 4404 and that the particle beam 4405 may pass through both together as the particle beam is scanned in the forward direction 4404 during plate movement to produce reduced-energy particle beam 4405a. Referring to FIG. 45, after both plates reach their ending position 4407, 2× plate 4401 may be retracted first (moved in the reverse direction 4409), while the particle beam is scanned in the reverse direction and passes through the 1× plate 4402 only to produce reduced energy particle beam 4405b. While the particle beam is scanned in the reverse direction, the 1× plate 4402 may also be moved in the reverse direction, as shown. As explained above, the particle beam will be scanned across the beam field and through one or more plates at appropriate distances from the edge of each plate. Referring to FIG. 46, after the particle beam scan reaches the starting position and plate 4402 is fully retracted, another 2× plate 4410 may be moved into position and both 2× plates 4401 and 4410 may be moved in the forward direction of arrow 4404 as the particle beam is scanned in the forward direction to produce reduced-energy particle beam 4405c. Sequencing of various plates may continue, as appropriate, until all layers of the target are treated.

Figure 47:
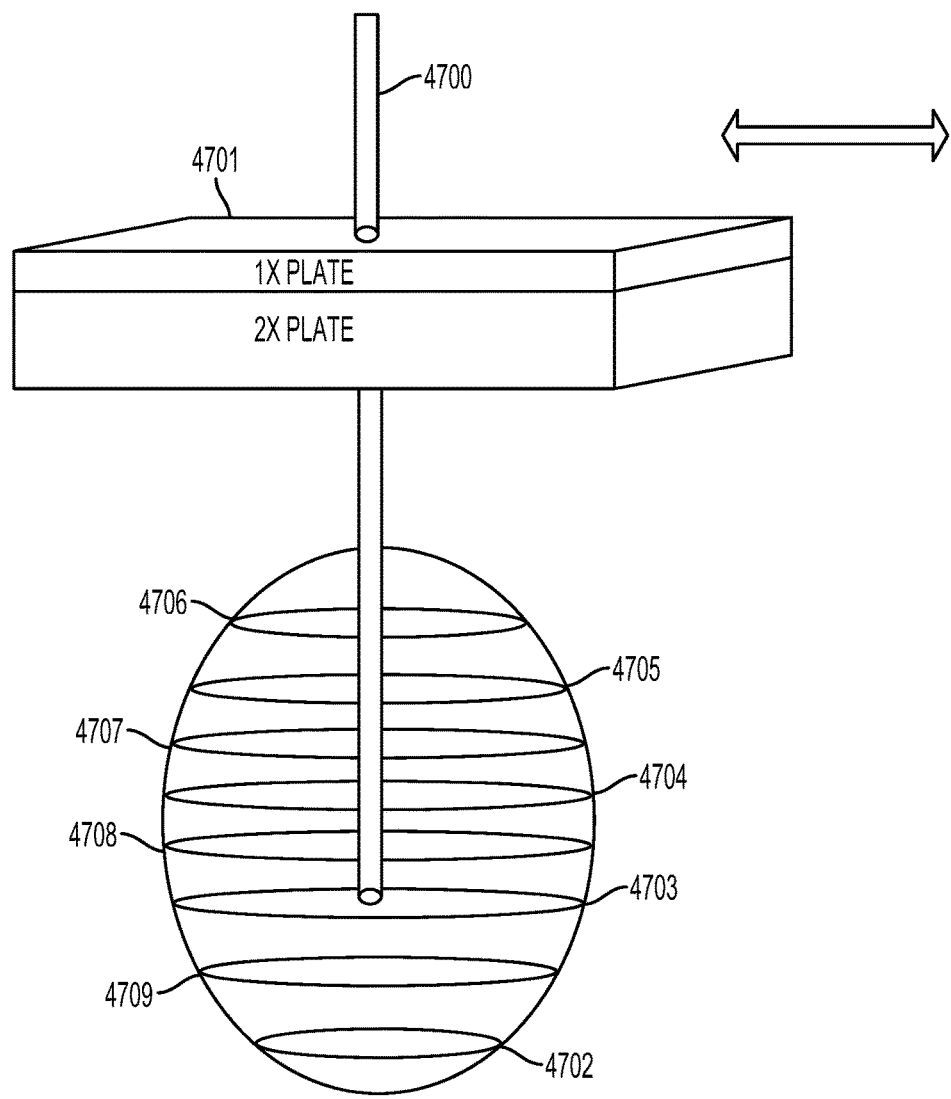
FIG. 47 is a perspective view showing plates combined, and moving during scanning, to hit a layer within an irradiation target.

As noted above, example implementations of the energy degrader may contain multiple plates, each having a thickness of 2×, and a single plate or multiple plates having a thickness of 1×. In implementations such as these, the plates are sequenced so as to treat each layer of the target. For example, as shown in FIG. 47, together with zero, one, or multiple 2× plates, a 1× plate 4701 can be moved into the beam field for every odd layer 4702 to 4705 to be treated by beam 4700, and moved out of the beam field for every even layer 4706 to 4709 to be treated. As explained herein, layers in the target may be treated out of order or not, depending upon the treatment plan.

In some implementations, as noted, all of the plates may have the same thickness. So, for example an initial, single plate may be moved into, and through, the beam field, and the particle beam scanned across the beam field during movement of the plate in order to produce a particle beam having the energy level sufficient to reach an appropriate layer. A second plate may begin motion before or after the first plate reached its ending position, and the particle beam may be scanned across the beam field and through the second plate beginning from near to its starting position following its motion while leaving the first plate in position. During scanning, the beam passes through both the first and second plates, thereby changing its energy accordingly. A third plate may begin motion before or after the second plate reaches its ending position, and the particle beam may be scanned across the beam field and through the third plate beginning from near to its starting position following its motion while leaving the first plate and the second plate in position (their ending positions). During scanning of the particle beam, the beam passes through the first, second, and third plates, thereby changing its energy accordingly. This process may be repeated using as many plates as needed to scan all layers of the irradiation target. In this example, scanning may be performed in the forward direction. In some implementations, the scanning process may be performed in the reverse direction. For example, all plates may be moved initially from the starting position to the ending position, and scanned in the forward direction during movement. Thereafter, individual plates may be retracted, with the particle beam being scanned through the remaining plates, e.g., in the reverse direction, thereby producing particle beams that hit successively deeper layers of the irradiation target. This process may be repeated until all, or an appropriate number, of plates have been retracted.

Figure 48:
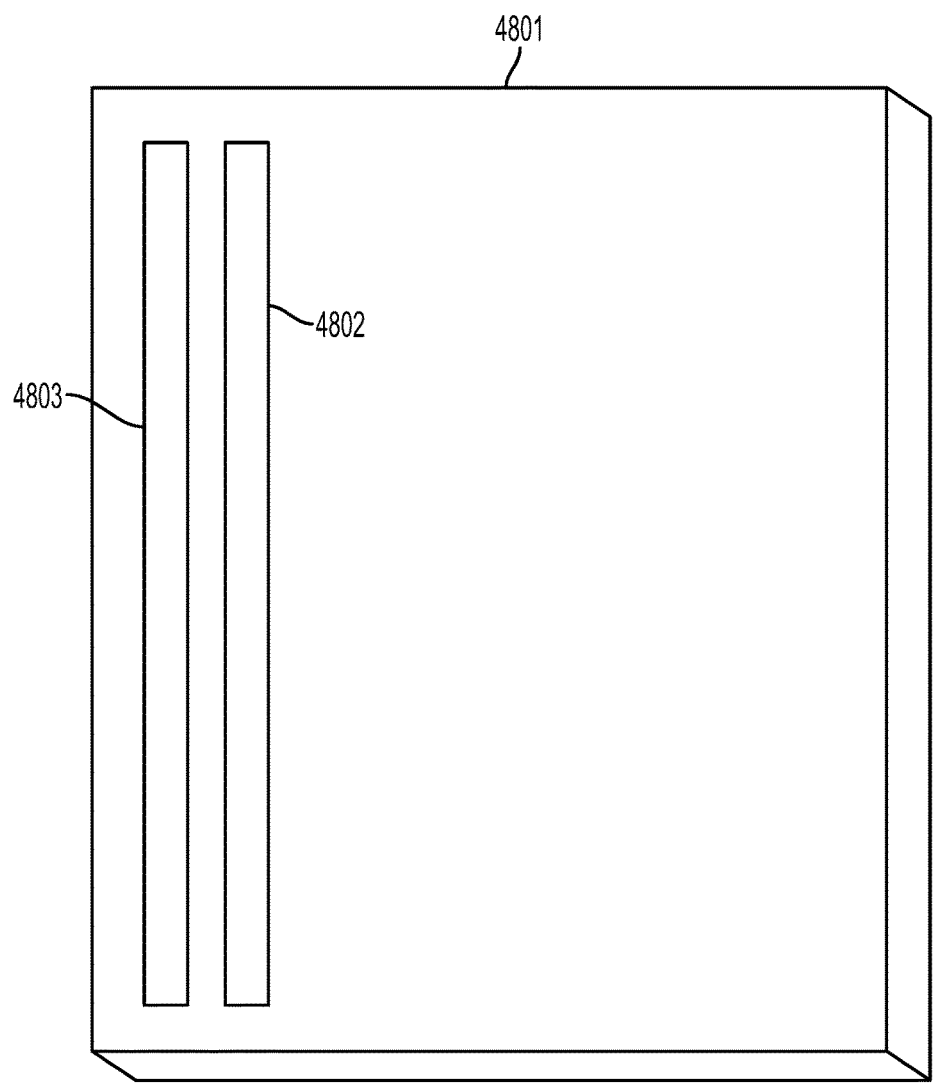
FIG. 48 is a top perspective view of a plate containing sensors.

As noted, control over scanning and the energy degrader may be implemented using one or more computing systems. In an example implementation, each plate of the energy degrader includes one or more sensors that are configured to identify a location of the plate relative to the beam field. Referring to FIG. 48, in some implementations, each plate 4801 includes two sensors 4802, 4803.

In some implementations, as shown in FIG. 48, the sensors are strip sensors located on the same side of each plate; however, in other implementations, the number, configuration, and placement of the sensors may be different than that shown in FIG. 48 or described herein. In an example operation, the sensors are independent, e.g., the output of one sensor is not dependent upon the output of the other sensor. Independent sensors provide redundancy, and confirmation that the determined location of the plate is accurate. Each sensor detects the position of the plate on which the sensors are located relative to, and within, the beam field, and relays that position to the computing system(s) that controls operation of the scanning system. The feedback from the sensors may be continuous during plate motion. In some implementations, the sensors output voltage that is proportional to plate positions; however, other types of sensors may be used, e.g., ones that detect motor motion in relation to plate position. The particle therapy control system uses this information to determine where to place the beam, and where and when to begin scanning. The computing system(s) may also control movement of the plates into and out of the beam field. Control may be based on the treatment plan and may be coordinated with control of the scanning system.

In some implementations, the speed of movement of the plates may be the same regardless of plate thickness, direction of movement (e.g., starting to ending position or ending to starting position), or position relative to any other plate. In some implementations, the speed of movement of plates may be controlled and may vary. For example, in some implementations, the speed of a trailing plate may be different (e.g., greater than) the speed of a plate being scanned during motion. This may be, e.g., to enable the trailing plate to reach an appropriate location at a set time. In some implementations, plate position may be determined, or augmented, based on knowledge of the plate's speed, its initial position, and the time at which it began motion. For example, expected plate position may be calculated based on knowledge of the plate's speed, its initial position, and the time at which it began motion. In some implementations, because the plates are moved in coordination with movement of the beam during scanning, the plates need only move as fast as the beam is moved. In some cases, this coordinated movement of the beam and plates may reduce noise and mechanical wear on the energy degrader relative known degraders that move the plates as fast as possible.

As noted above, particles in the beam have a Gaussian distribution. In some implementations, passage through one or more plates may result in further beam divergence. For example, referring to FIG. 34, an aperture 3404 may be positioned between the energy degrader and the irradiation target (e.g., the patient). The aperture trims spots located near the edges of the irradiation target, e.g., blocks a portion of the particle beam to provide a sharp edge to the beam and to protect surrounding (non-treated) tissue from the particle beam. For example, beam-blocking material of the aperture may be placed between a part of the beam and healthy tissue to block the application of the beam to healthy tissue. In some implementations, the aperture is controllable dynamically to change shape and thereby adapt to the shape of the radiation target. Examples of apertures that may be used are described in U.S. patent application Ser. No. 14/937,048 filed on Nov. 10, 2015 and titled "Adaptive Aperture", which is incorporated herein by reference. Examples of structures that may operate to block a portion of the particle beam to provide a sharp edge to the beam and to protect surrounding (non-treated) tissue from the particle beam are also referred to as collimators herein, and may be used in the implementation of FIG. 34.

The elements used in the energy degrader and operation thereof described herein are not limited to plates. Rather, any appropriate structure may be used to affect the energy of the particle beam. In implementations that employ plates or similar structures, each plate or structure need not be of uniform thickness, e.g., there may be at least some thickness variation across one or more individual plates. If such plates are of an appropriate size (e.g., sufficiently small), such plates may be moved across the beam field so that the beam passes through one or more plates and through different portions of those plates having different thicknesses in order to treat different layers of the target.

The control of the gantry, the patient support, the active beam shaping elements (including, for example, the aperture, the energy degrader, and the scanning), and the synchrocyclotron to perform a therapy session is achieved by appropriate therapy control electronics (not shown).

Control of the particle therapy system described herein and its various features may be implemented using hardware or a combination of hardware and software. For example, a system like the ones described herein may include various controllers and/or processing devices located at various points. A central computer may coordinate operation among the various controllers or processing devices. The central computer, controllers, and processing devices may execute various software routines to effect control and coordination of testing and calibration.

System operation can be controlled, at least in part, using one or more computer program products, e.g., one or more computer program tangibly embodied in one or more non-transitory machine-readable media, for execution by, or to control the operation of, one or more data processing apparatus, e.g., a programmable processor, a computer, multiple computers, and/or programmable logic components.

A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a network.

Actions associated with implementing all or part of the operations of the particle therapy system described herein can be performed by one or more programmable processors executing one or more computer programs to perform the functions described herein. All or part of the operations can be implemented using special purpose logic circuitry, e.g., an FPGA (field programmable gate array) and/or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only storage area or a random access storage area or both. Elements of a computer (including a server) include one or more processors for executing instructions and one or more storage area devices for storing instructions and data. Generally, a computer will also include, or be operatively coupled to receive data from, or transfer data to, or both, one or more machine-readable storage media, such as mass PCBs for storing data, e.g., magnetic, magneto-optical disks, or optical disks. Non-transitory machine-readable storage media suitable for embodying computer program instructions and data include all forms of non-volatile storage area, including by way of example, semiconductor storage area devices, e.g., EPROM, EEPROM, and flash storage area devices; magnetic disks, e.g., internal hard disks or removable disks; magneto-optical disks; and CD-ROM and DVD-ROM disks.

Any "electrical connection" as used herein may imply a direct physical connection or a connection that includes intervening components but that nevertheless allows electrical signals to flow between connected components. Any "connection" involving electrical circuitry mentioned herein that allows signal(s) to pass, unless stated otherwise, is an electrical connection and not necessarily a direct physical connection regardless of whether the word "electrical" is used to modify "connection".

Any two more of the foregoing implementations may be used in an appropriate combination in an appropriate particle accelerator (e.g., a synchrocyclotron). Likewise, individual features of any two more of the foregoing implementations may be used in an appropriate combination.

Elements of different implementations described herein may be combined to form other implementations not specifically set forth above. Elements may be left out of the processes, systems, apparatus, etc., described herein without adversely affecting their operation. Various separate elements may be combined into one or more individual elements to perform the functions described herein.

The example implementations described herein are not limited to use with a particle therapy system or to use with the example particle therapy systems described herein. Rather, the example implementations can be used in any appropriate system that directs accelerated particles to an output.

Other implementations not specifically described herein are also within the scope of the following claims.

What is claimed is:

1. A particle therapy system comprising:
   a particle accelerator to output a particle beam;
   a scanning magnet to move the particle beam;
   a control system; and
   an energy degrader comprising multiple plates, the multiple plates being controllable by the control system to change an energy of the particle beam by passing the particle beam through one or more of the multiple plates to an irradiation target, the multiple plates comprising:
      a first plate that is controllable by the control system to move across at least part a beam field in a first direction while the particle beam is incident on a surface of the first plate in the beam field and while the particle beam is moved by the scanning magnet across the surface of the first plate, where movement of the particle beam across the surface of the first plate is at least partly in the first direction, and
      a second plate that is controllable by the control system to move across the at least part of the beam field while the particle beam is moved across the surface of the first plate, the second plate being controllable to trail or to lead the first plate in the first direction such that the particle beam does not pass through the second plate during at least part of movement of the first plate and the second plate.

2. The particle therapy system of claim 1, wherein the second plate is controllable by the control system to trail the first plate during movement.

3. The particle therapy system of claim 1, further comprising:
   a scanning system that is controllable by the control system to move the particle beam in multiple dimensions relative to the irradiation target, the scanning magnet being part of the scanning system;
   wherein at least one of the energy degrader or the scanning system is controllable by the control system so that, during at least part of the movement of the first plate and the second plate, the particle beam passes through the first plate but not the second plate.

4. The particle therapy system of claim 1, further comprising:
a scanning system that is controllable by the control system to move the particle beam in multiple dimensions relative to the irradiation target, the scanning magnet being part of the scanning system;
wherein at least one of the energy degrader or the scanning system is controllable by the control system so that, during at least part of the movement of the first plate and the second plate, the particle beam passes through both the first plate and the second plate.

5. The particle therapy system of claim 1, further comprising:
a scanning system that is controllable by the control system to move the particle beam in multiple dimensions relative to the irradiation target, the scanning magnet being part of the scanning system;
wherein movement of the particle beam across a plate among the multiple plates is limited to movement outside of a predefined distance from an edge of the plate.

6. The particle therapy system of claim 1, wherein, during movement of the first plate and the second plate, the first plate and the second plate move between a starting position and an ending position; and
wherein the scanning magnet is controllable by the control system to move the particle beam at least partly in a direction of the ending position such that the particle beam passes through only the first plate during the at least part of the movement between the starting position and the ending position.

7. The particle therapy system of claim 1, wherein, during movement of the first plate and the second plate, the first plate and the second plate move between a starting position and an ending position; and
wherein the scanning magnet is controllable by the control system to move the particle beam at least partly in a direction of the starting position such that the particle beam passes through only the first plate during the at least part of the movement between the starting position and the ending position.

8. The particle therapy system of claim 1, wherein the multiple plates comprise one or more first plates including the first plate and one or more second plates including the second plate, the one or more first plates and the one or more second plates being controllable by the control system to move relative to the particle beam, each of one or more first plates having a thickness that is less than thicknesses of the one or more second plates.

9. The particle therapy system of claim 8, wherein the first plate has a thickness that is a fraction of a thickness of each of the one or more second plates.

10. The particle therapy system of claim 9, wherein the first plate has a thickness that is half of a thickness of each of the one or more second plates.

11. The particle therapy system of claim 1, wherein control over movement of the multiple plates by the control system comprises sequencing movement of the multiple plates so that each of multiple layers of the irradiation target is subjected to the particle beam.

12. The particle therapy system of claim 11, wherein control over movement of the multiple plates by the control system comprises sequencing movement of the multiple plates so that the multiple layers of the irradiation target are treated with the particle beam non-sequentially.

13. The particle therapy system of claim 1, wherein control over movement of the multiple plates by the control system comprises sequencing movement of the multiple plates so that an energy of the particle beam corresponds to a location of each of multiple layers of the irradiation target.

14. The particle therapy system of claim 1, further comprising:
an aperture that is controllable by the control system to trim spots of the particle beam, the aperture being between the irradiation target and the energy degrader.

15. The particle therapy system of claim 1, wherein each of the multiple plates has a size that is less than a size of the beam field.

16. The particle therapy system of claim 1, wherein the particle accelerator comprises a synchrocyclotron that is movable relative to the irradiation target.

17. The particle therapy system of claim 16, further comprising:
a gantry on which the synchrocyclotron is mounted to move relative to the irradiation target.

18. The particle therapy system of claim 1, further comprising:
a structure to block at least part of the particle beam from reaching the irradiation target, the structure being configured to track movement of the particle beam relative to the irradiation target.

19. The particle therapy system of claim, 18, wherein the structure comprises fingers that are movable separately from movement of the structure to track movement of the particle beam.

20. The particle therapy system of claim 1, wherein a speed of movement of the first plate and the second plate is based on a speed of movement of the particle beam.

21. The particle therapy system of claim 1, wherein the particle beam is movable independently of at least one of the first plate or the second plate.

22. The particle therapy system of claim 1, further comprising:
a gantry on which particle accelerator is mounted to move relative to the irradiation target, the energy degrader also being mounted on the gantry.

23. The particle therapy system of claim 1, wherein the second plate is controllable by the control system to lead the first plate during movement.

* * * * *